US012082846B2

(12) United States Patent
Noblett et al.

(10) Patent No.: US 12,082,846 B2
(45) Date of Patent: Sep. 10, 2024

(54) EXTERNAL FIXATION STRUT

(71) Applicants: Smith & Nephew, Inc., Memphis, TN (US); Smith & Nephew Orthopaedics AG, Zug (CH); Smith & Nephew Asia Pacific Pte. Limited, Singapore (SG)

(72) Inventors: Andrew Noblett, Bartlett, TN (US); Johnny R. Mason, Bartlett, TN (US); Paul Bell, Memphis, TN (US)

(73) Assignees: Smith & Nephew, Inc.; Smith & Nephew Orthopaedics AG, Zug (CH); Smith & Nephew Asia Pacific Pte. Limited, Singapore (SG)

( * ) Notice: Subject to any disclaimer, the term of this patent is extended or adjusted under 35 U.S.C. 154(b) by 217 days.

(21) Appl. No.: 17/845,065

(22) Filed: Jun. 21, 2022

(65) Prior Publication Data

US 2022/0313317 A1 Oct. 6, 2022

Related U.S. Application Data

(63) Continuation of application No. 17/289,592, filed as application No. PCT/US2019/057339 on Oct. 22, 2019, now Pat. No. 11,395,679.

(Continued)

(51) Int. Cl.
*A61B 17/64* (2006.01)
*A61B 17/00* (2006.01)

(52) U.S. Cl.
CPC ............ *A61B 17/6475* (2013.01); *A61B 2017/00367* (2013.01)

(58) Field of Classification Search
CPC ...... A61B 17/6475; A61B 2017/00367; A61B 17/64; A61B 17/62
(Continued)

(56) References Cited

U.S. PATENT DOCUMENTS

| 5,702,389 A | 12/1997 | Taylor et al. |
| 6,030,386 A | 12/2000 | Taylor et al. |

(Continued)

FOREIGN PATENT DOCUMENTS

| WO | 01/15611 A1 | 3/2001 |
| WO | 2014/159824 A2 | 10/2014 |
| WO | 2017/139517 A1 | 8/2017 |

OTHER PUBLICATIONS

International Search Report and Written Opinion for International Application No. PCT/US2019/057339, mailed Apr. 21, 2020.

*Primary Examiner* — Nicholas J Plionis
*Assistant Examiner* — Tara Rose E Carter
(74) *Attorney, Agent, or Firm* — KDW Firm PLLC

(57) ABSTRACT

Embodiments of the invention include an external fixation system that includes at least one external fixation strut that is both acutely adjustable and precisely adjustable and related methods of adjustment. Acute adjustment may be accomplished using one or more mobile jaws that may be engaged with or disengage from a threaded rod of each external fixation strut. Precise adjustment of each external fixation strut may be accomplished after releasing a lock biased toward a locked position. When each external fixation strut's lock is released, a portion of each of the precise adjustment mechanism of each external fixation strut may be activated to increase and decrease the length of each of the at least one external fixation struts.

21 Claims, 45 Drawing Sheets

Related U.S. Application Data

(60) Provisional application No. 62/752,671, filed on Oct. 30, 2018.

(58) Field of Classification Search
USPC .................................................. 606/53–59
See application file for complete search history.

(56) References Cited

U.S. PATENT DOCUMENTS

| | | |
|---|---|---|
| 11,395,679 B2 * | 7/2022 | Noblett .............. A61B 17/6475 |
| 2003/0191466 A1 | 10/2003 | Austin et al. |
| 2009/0198234 A1 | 8/2009 | Knuchel et al. |
| 2010/0331840 A1 | 12/2010 | Ross et al. |
| 2011/0208187 A1 | 8/2011 | Wong |
| 2013/0338713 A1 | 12/2013 | Kawakami et al. |
| 2014/0135764 A1 | 5/2014 | Ross et al. |
| 2014/0276817 A1 * | 9/2014 | Murray .................. A61B 17/62 606/56 |
| 2015/0080892 A1 | 3/2015 | Lehmann et al. |
| 2018/0214181 A1 | 8/2018 | Mannanal |
| 2018/0344354 A1 | 12/2018 | Mullaney |

* cited by examiner

EXTERNAL FIXATION STRUT

CROSS-REFERENCE TO RELATED APPLICATION

This application is a continuation application of pending U.S. patent application Ser. No. 17/289,592, filed Apr. 28, 2021, entitled "External Fixation Strut," which is a United States National Phase filing of International Application No. PCT/US2019/057339, filed Oct. 22, 2019, which claims the benefit of U.S. Provisional Patent Application No. 62/752,671, filed Oct. 30, 2018, entitled "External Fixation Strut," the entire contents of which applications are hereby incorporated by reference in their entirety.

FIELD OF THE INVENTION

The present disclosure relates generally to the field of orthopedic implants, and more particularly but not exclusively relates to orthopedic external fixation devices and related methods.

BACKGROUND

External fixation devices have been successfully used in orthopedics for a long time. Hexapod systems in particular have proven to be valuable clinical tools for treating a variety of conditions. One well known hexapod system is the Taylor Spatial Frame (TSF) by Smith and Nephew. The TSF has demonstrated clinical success for decades and has inspired development of many similar systems.

In general, orthopedic hexapods may include first and second bases, which may generally be in the form of rings, fixation components, and up to six variable length struts. The fixation components are connected to each of the bases to secure the bases to the patient's bone fragments. The six struts connect the two bases to one another and allow for precise manipulation of the bases, and hence the patient's bone fragments, in six degrees of freedom.

Generally speaking, in the most basic sense, the variable length struts include a strut body, a threaded rod, and a mechanism for adjustment. In use, the threaded rod may translate relative to the strut body to change the overall length of the strut. Thus arranged, by individually adjusting each of the struts, manipulation of the relative positions of the first and second bases, and hence the patient's bone fragments coupled thereto is possible. Patients or caregivers adjust the strut lengths according to a computer-generated prescription to achieve a desired correction.

Medical device companies have been developing external fixation struts with additional telescopic bodies, various acute and precise adjustment mechanisms, and assorted joint designs.

It is with respect to these and other considerations that the present improvements may be useful.

SUMMARY

This Summary is provided to introduce a selection of concepts in a simplified form that are further described below in the Detailed Description. This Summary is not intended to identify key features or essential features of the claimed subject matter, nor is it intended as an aid in determining the scope of the claimed subject matter.

An external fixation strut is disclosed. In one example of an embodiment, the external fixation strut comprises a strut body operatively associated with a first connector, a threaded rod including threads formed thereon, the threaded rod being operatively associated with a second connector, and an acute adjustment mechanism selectively disengageable from the threads of the threaded rod. In use, the threaded rod is rotationally fixed relative to the strut body so that movement of the threaded rod relative to the strut body moves the first connector relative to the second connector. The acute adjustment mechanism comprises an actuator body, a mobile jaw that is engageable with the threads of the threaded rod, and a disengagement member configured to interact with the mobile jaw to disengage the mobile jaw from the threads of the threaded rod. In use, the disengagement member is selectively movable from a first position to a second position such that when in the second position, the disengagement member interacts with the mobile jaw to disengage the mobile jaw from the threads of the threaded rod to enable the first and second connectors to be adjusted acutely.

In some embodiments, the mobile jaw includes a threaded surface configured to engage with the threads of the threaded rod.

In some embodiments, the acute adjustment mechanism includes two substantially oppositely positioned mobile jaws configured to engage with threads of the threaded rod on substantially opposite sides of the threaded rod.

In some embodiments, the substantially oppositely positioned mobile jaws each include a threaded surface configured to engage with threads of the threaded rod.

In some embodiments, the mobile jaw is biased to engage with the threaded rod.

In some embodiments, the mobile jaw is biased to disengage from the threaded rod.

In some embodiments, the disengagement member is a button configured to interact with the mobile jaw to disengage the mobile jaw from the threads of the threaded rod when the button is moved by a user from the first position to the second position.

In some embodiments, the button includes an angled face configured to interact with one or more faces of the mobile jaw to disengage the mobile jaw from the threads of the threaded rod.

In some embodiments, the disengagement member is configured to translate toward the mobile jaw when moved from the first position to the second position to disengage the mobile jaw from the threaded rod and the disengagement member is configured to rotate about the disengagement member's axis of translation to lock the acute adjustment mechanism in a state of free movement where the mobile jaw is disengaged from the threaded rod.

In some embodiments, the disengagement member is configured to translate away from the mobile jaw when moved from the first position to the second position to enable the mobile jaw to disengage from the threaded rod.

In some embodiments, the disengagement member includes a containment device configured to prevent the mobile jaw from moving away from the threads of the threaded rod when the containment device is coupled to the acute adjustment mechanism.

In some embodiments, the containment device is arranged and configured as an ID band for identifying each respective strut.

In some embodiments, the mobile jaw is configured to translate away from the threaded rod when interacted with by the disengagement member.

In some embodiments, the mobile jaw is configured to pivot away from the threaded rod when interacted with by the disengagement member.

In some embodiments, the actuator body includes a threaded collar that couples the actuator body with the strut body.

In some embodiments, the actuator body includes channels configured to guide the movement of the mobile jaw when the mobile jaw is interacted with by the disengagement member.

In some embodiments, the actuator body includes channels configured to constrain the movement of protrusions on the mobile jaw when the mobile jaw is interacted on by the disengagement member.

In some embodiments, the mobile jaw has one or more angled faces configured to interact with the disengagement member to move the mobile jaw away from the threaded rod.

In some embodiments, the external fixation strut further comprises a rotatable sleeve that is sized to fit over the outside of the actuator body with one or more openings for access to the disengagement member.

In some embodiments, when the rotatable sleeve is rotated relative to the actuator body, access to the disengagement member is blocked.

In some embodiments, when the rotatable sleeve is rotated relative to the actuator body a portion of opening interacts with the disengagement member to disengage the mobile jaw from the threaded rod.

In some embodiments, the external fixation strut further comprises a precise adjustment mechanism comprising a lock positioned between the strut body and the actuator body; wherein the lock is movable between a first position and a second position, in the first position, the lock is arranged and configured to rotationally fix the strut body relative to the actuator body in the second position, the lock is arranged and configured to enable rotation of the actuator body relative to the strut body to move the threaded rod longitudinally relative to the strut body.

In some embodiments, the lock of the precise adjustment mechanism includes a base coupled to the strut body, a plunger biased away from the base, and a cavity formed in the actuator body, the cavity arranged and configured to receive the plunger to restrict rotational movement of the strut body relative to the actuator body.

In some embodiments, the lock of the precise adjustment mechanism includes a pivot coupled to the actuator body, the pivot being biased toward the strut body and being arranged and configured to fit in a notch formed in the strut body to restrict rotational movement of the strut body relative to the actuator body when a portion of the pivot is positioned in the notch in the strut body.

In some embodiments, the actuator body includes openings for receiving projections of a band to prevent disengagement of the mobile jaw from the threaded rod.

In some embodiments, the external fixation strut further comprises a band, wherein the band is arranged and configured to cover the disengagement member when the band is positioned on the acute adjustment mechanism to prevent access to the disengagement member.

In some embodiments, the first and second connectors are first and second U-joints, respectively, the first and second U-joints including first and second devises, a central body having a plurality of threaded openings, and a plurality of set screws arranged and configured to couple the central body to the first and second joint devises.

In some embodiments, the external fixation strut further comprises a tracer pin operatively coupled to the threaded rod and a locking sleeve operatively coupled to the strut body, the locking sleeve including an opening arranged and configured to receive the tracer pin, the locking sleeve being arranged and configured to prevent movement of the track pin and thus to prevent adjustment of the external fixation strut.

An alternate embodiment of an external fixation strut may include a strut body, a threaded rod substantially rotationally fixed relative to the strut body, an acute adjustment mechanism, and an optional precise adjustment mechanism comprising a lock between the strut body and the actuator body. The acute adjustment mechanism may be selectively disengageable from threads of the threaded rod and include an actuator body, a mobile jaw that is engageable with the threads of the threaded rod, and a disengagement member configured to interact with the mobile jaw to disengage the mobile jaw from the threads of the threaded rod. The lock may be biased to fix the strut body with the actuator body rotationally, but may be activated to allow for rotation of the actuator body relative to the strut body to move the threaded rod longitudinally relative to the strut body.

Another embodiment of an external fixation system may include an upper base, a lower base, and at least two struts coupled between the upper base and the lower base. At least one of the struts includes a strut body, a threaded rod substantially rotationally fixed relative to the strut body, and an acute adjustment mechanism selectively disengageable from the threads of the threaded rod. The acute adjustment mechanism may include an actuator body, a mobile jaw that is engageable with the threads of the threaded rod, and a disengagement member configured to interact with the mobile jaw to disengage the mobile jaw from the threads of the threaded rod. At least one of the struts may optionally include a precise adjustment mechanism comprising a lock between the strut body and the actuator body. The lock may be biased to fix the strut body with the actuator body rotationally, but may be activated to allow for rotation of the actuator body relative to the strut body to move the threaded rod longitudinally relative to the strut body.

Still another embodiment is directed to a method of adjusting an external fixation strut. The method may include disengaging an acute adjustment mechanism of the external fixation strut from threads of a threaded rod of the external fixation strut, wherein the acute adjustment mechanism is biased toward an engaged state, and wherein the threaded rod is substantially rotationally fixed relative to a strut body of the external fixation strut, and moving the acute adjustment mechanism relative to the threaded rod to a position closer to a final adjustment position. The method may also include engaging the acute adjustment mechanism of the external fixation strut to the threads of the threaded rod by removing force against the bias toward an engaged state, releasing a lock of a precise adjustment mechanism that is configured to lock between the strut body and the acute adjustment mechanism, and with the lock of the precise adjustment mechanism in a released state, rotating the acute adjustment mechanism relative to the strut body to move the threaded rod longitudinally relative to the strut body.

Yet another embodiment is directed to a method of adjusting an external fixation strut. The method may include disengaging an acute adjustment mechanism of the external fixation strut from threads of a threaded rod of the external fixation strut, wherein the acute adjustment mechanism is biased toward a disengaged state, and wherein the threaded rod is substantially rotationally fixed relative to a strut body of the external fixation strut. The method may include moving the acute adjustment mechanism relative to the threaded rod to a position closer to a final adjustment position, engaging the acute adjustment mechanism of the external fixation strut to the threads of the threaded rod by applying force against the bias toward a disengaged state, and releasing a lock of a precise adjustment mechanism that is configured to lock between the strut body and the acute adjustment mechanism. With the lock of the precise adjustment mechanism in a released state, the acute adjustment mechanism may be rotated relative to the strut body to move the threaded rod longitudinally relative to the strut body.

Embodiments of the present disclosure provide numerous advantages. By incorporating an acute adjustment mechanism including one or more mobile jaws and a disengagement member, the external fixation strut facilitates gross adjustment of the length of the strut for acute adjustment and simplified installation and removal. In addition, the embodiments disclosed within the present disclosure describe a new strut design which focuses on safety with features impeding accidental adjustment of the acute and precise adjustment mechanisms. The embodiment of the present disclosure also focus on efficiency with components configured to preserve the maximum amount of working length on the threaded rod.

Further features and advantages of at least some of the embodiments of the present invention, as well as the structure and operation of various embodiments of the present invention, are described in detail below with reference to the accompanying drawings

DETAILED DESCRIPTION

Figure 1A:
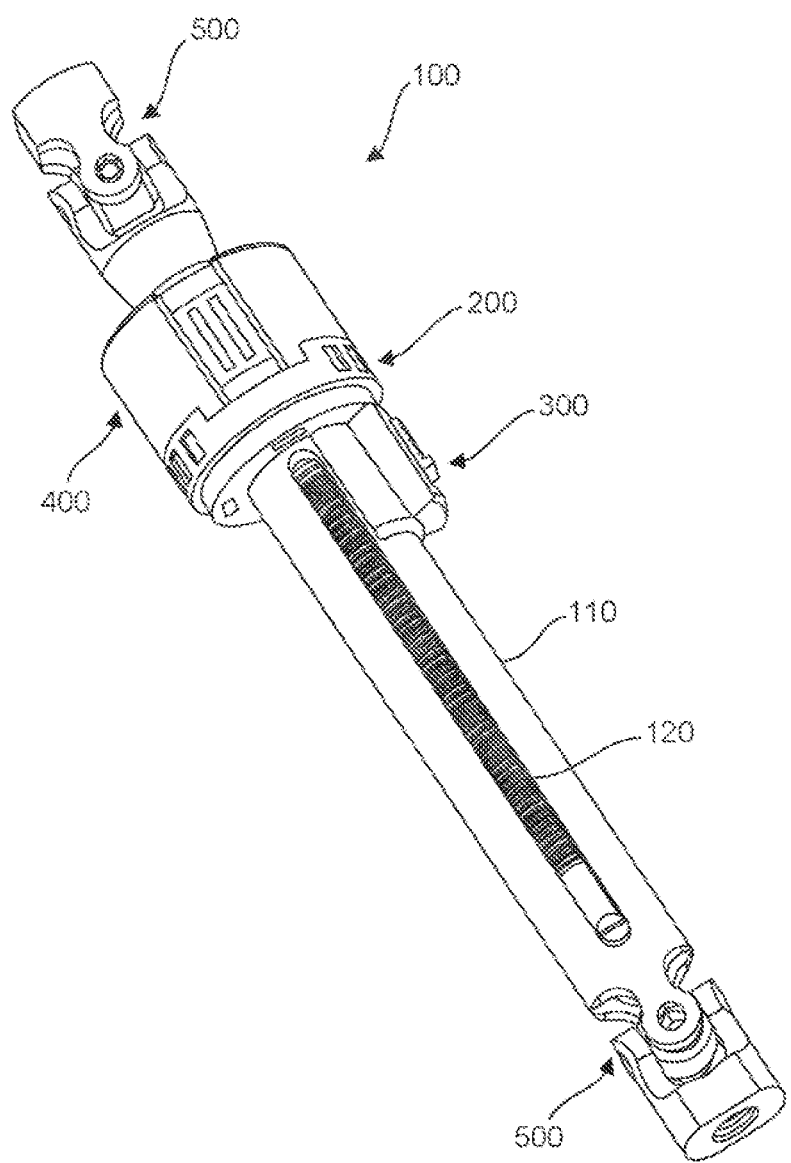
FIG. 1A illustrates a perspective view of an example of an embodiment of an external fixation strut in accordance with principles of the present disclosure.

For the purposes of promoting an understanding of the principles of the present disclosure, reference will now be made to the embodiments illustrated in the figures and specific language will be used to describe the same. The external fixation struts of the present disclosure may, however, be embodied in many different forms and should not be construed as being limited to the embodiments set forth herein. Rather, these embodiments are provided so that this disclosure will convey certain aspects of the external fixation struts to those skilled in the art. As such, it will be understood that no limitation of the scope of the present disclosure is hereby intended. Any alterations and further modifications in the described embodiments, and any further applications of the principles of the present disclosure as described herein are contemplated as would normally occur to one skilled in the art to which the disclosure relates. In the drawings, like numbers refer to like elements throughout unless otherwise noted.

Referring to FIGS. 1A-10, in one example of an embodiment, an external fixation strut 100 is disclosed. As shown in the example embodiment, the external fixation strut 100 may include a strut body 110, a threaded rod 120 substantially rotationally fixed relative to the strut body 110 so that movement of the threaded rod 120 axially translates or moves the threaded rod 120 relative to the strut body 110 (e.g., movement of the threaded rod 120 is limited to translation relative to the strut body 110), an acute adjustment mechanism 200 selectively disengageable from threads of the threaded rod 120, and a precise adjustment mechanism 300.

In one example of an embodiment, the acute adjustment mechanism 200 includes an actuator body 210 that includes a threaded collar 250, a spring-loaded mobile jaw 220 including associated biasing springs 214, and one or more disengagement members 230 that are configured to interact with the mobile jaw 220. As shown, the actuator body 210 may include apertures 216 to receive at least a portion of the disengagement members 230. The disengagement members 230 may be in the form of one or more buttons, but other embodiments are envisioned including, for example, one or more wedges, screws, cams, or any other mechanism now known or hereafter developed.

In the illustrated embodiment, the external fixation strut 100 may also include a rotating sleeve 240. In use, the rotating sleeve 240 is arranged and configured to fit over the outside of the actuator body 210. The rotating sleeve 240 may include openings 260 to provide access to the disengagement members 230 for reasons that will be described in greater detail below.

The threaded collar 250 is arranged and configured to couple the actuator body 210 to the strut body 110. In one example of an embodiment, the actuator body 210 may include one or more channels 212 (FIG. 5B) to guide the path of the mobile jaws 220 and the associated springs 214. In use, the associated springs 214 bias the mobile jaws 220 against the threaded rod 120 and toward the disengagement members 230. For example, the mobile jaws 220 have faces 222 that interact with surfaces 232 of the disengagement members 230 so that when the disengagement members 230 are pressed inward, the mobile jaws 220 move (e.g., separate and disengage) from the threaded rod 120 so that the strut length of the external fixation strut 100 can be adjusted acutely. In use, the acute adjustment mechanism 200 facilitates gross adjustment. For example, when installing an external fixation system, a surgeon may initially implant the external fixation system with the acute adjustment mechanism 200 disengaged from the threaded rod 120 (e.g., the mobile jaws 220 may be disengaged from the threaded rod 120). Thus arranged, the surgeon can correct the patient's deformity acutely (making gross corrections in the operating room). Once the surgeon has completed placing, positioning, implanting, etc. the external fixation system, the acute adjustment mechanism 200 may be moved to the activated, coupled, etc. position so that the acute adjustment mechanism 200 engages the threaded rod 120 (e.g., mobile jaws 220 engage the threaded rod 120) to lock, fix, etc. the position of the external fixation struts. Thereafter, the struts can be adjusted in small increments using the precise adjustment mechanism 300, for example, by the patient in connection with daily adjustments needed to comply with the prescription.

In one example of an embodiment, as shown, the precise adjustment mechanism 300 includes a body 310, a plunger 320, and a spring 330. The spring 330 biases the plunger 320 to an extended position beyond an outer edge 312 of the body 310 and into a cavity 252 of the threaded collar 250. The body 310 cannot turn as long as a portion of the plunger 320 is in the cavity 252 of the threaded collar 250.

In one example of an embodiment, as shown, the external fixation strut 100 may also include bands 400, as will be described herein. In addition, and/or alternatively, the external fixation strut 100 may also include and one or more connectors 500 to couple the external fixation strut 100 to one or more bases, as will be described in greater detail below. In use, the connectors 500 may be in the form of a Universal joint (U-joint) as shown, alternatively however any other now known or hereafter developed connector can be used such as, for example, ball joints, threaded ends, etc.

Figure 3A:
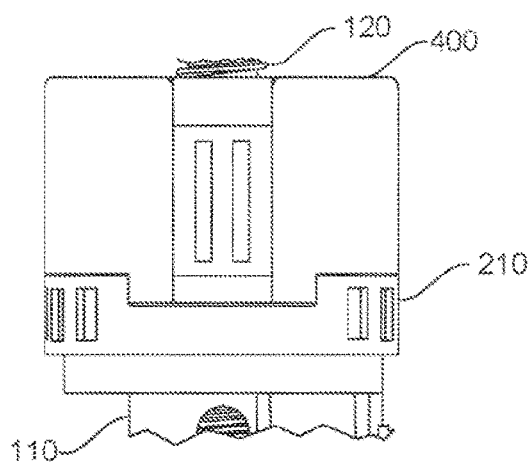
FIG. 3A illustrates a detailed, front elevation view of an example of an embodiment of an acute adjustment mechanism that can be used in combination with the external fixation strut shown in FIG. 1A.
Figure 3B:
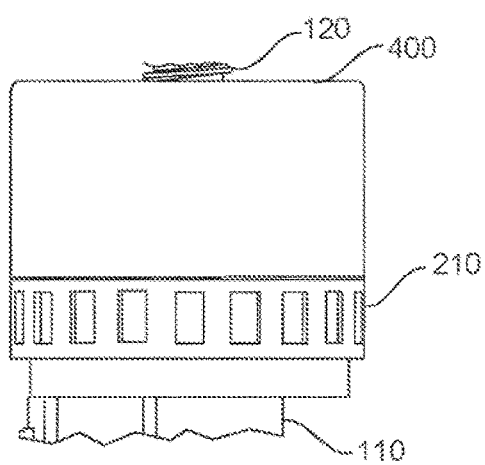
FIG. 3B illustrates a detailed, back elevation view of the acute adjustment mechanism shown in FIG. 3A.
Figure 3C:
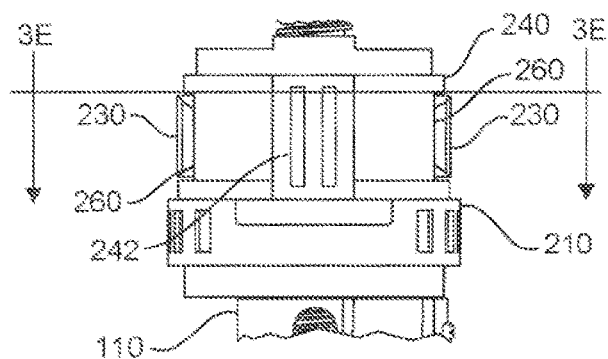
FIG. 3C illustrates a front elevation view of the acute adjustment mechanism shown in FIG. 3A, the acute adjustment mechanism shown with a band removed to illustrate a rotating sleeve.
Figure 3D:
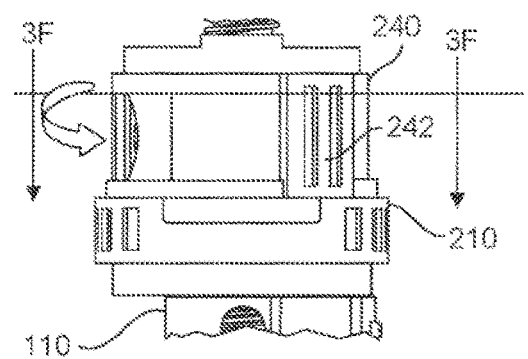
FIG. 3D illustrates a front elevation view of the acute adjustment mechanism shown in FIG. 3C with the rotating sleeve rotated counterclockwise.
Figure 3E:
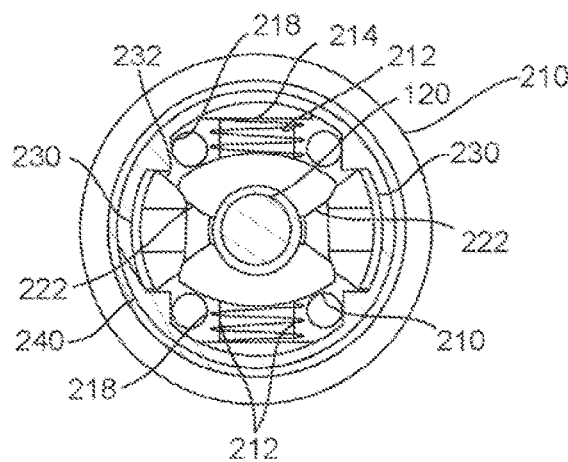
FIG. 3E illustrates a cross-sectional view of the acute adjustment mechanism shown in FIG. 3C, the acute adjustment mechanism including threads engaged with a threaded rod.
Figure 3F:
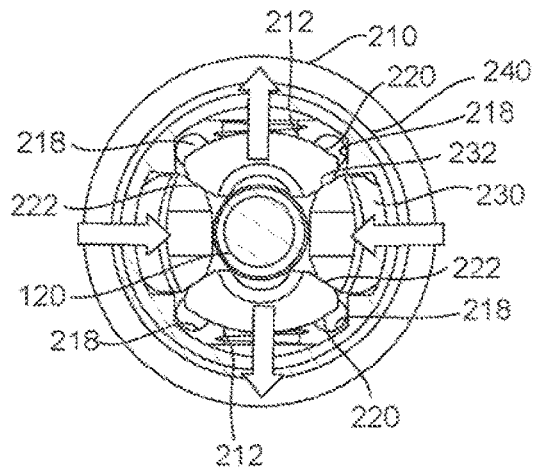
FIG. 3F illustrates a cross-sectional view of the acute adjustment mechanism shown in FIG. 3D, the acute adjustment mechanism shown with its threads disengaged from the threaded rod.
Figure 5A:
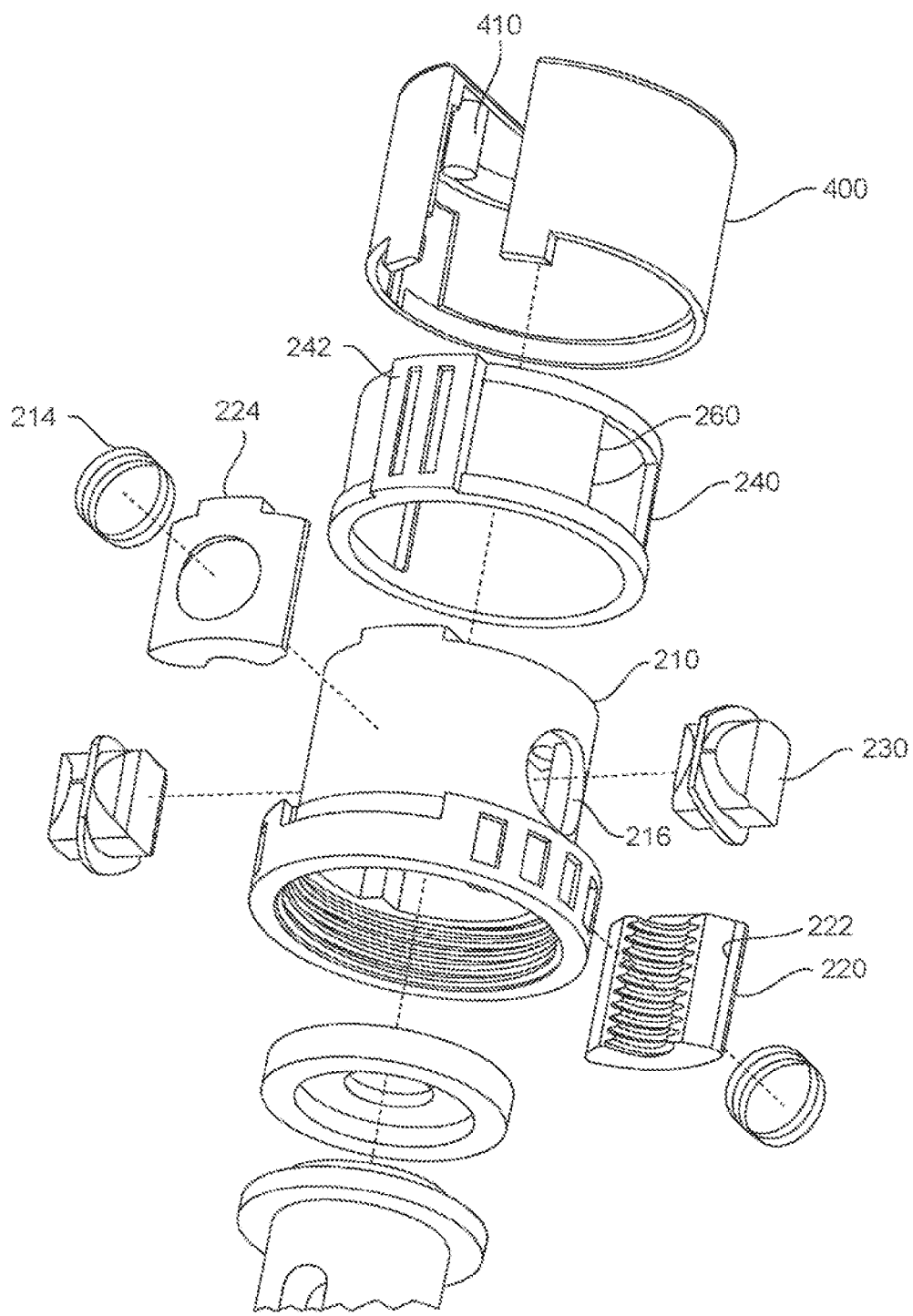
FIG. 5A illustrates an exploded, perspective view of an example of an embodiment of the acute adjustment mechanism that may be used in combination with the external fixation strut shown in FIG. 1A.
Figure 5B:
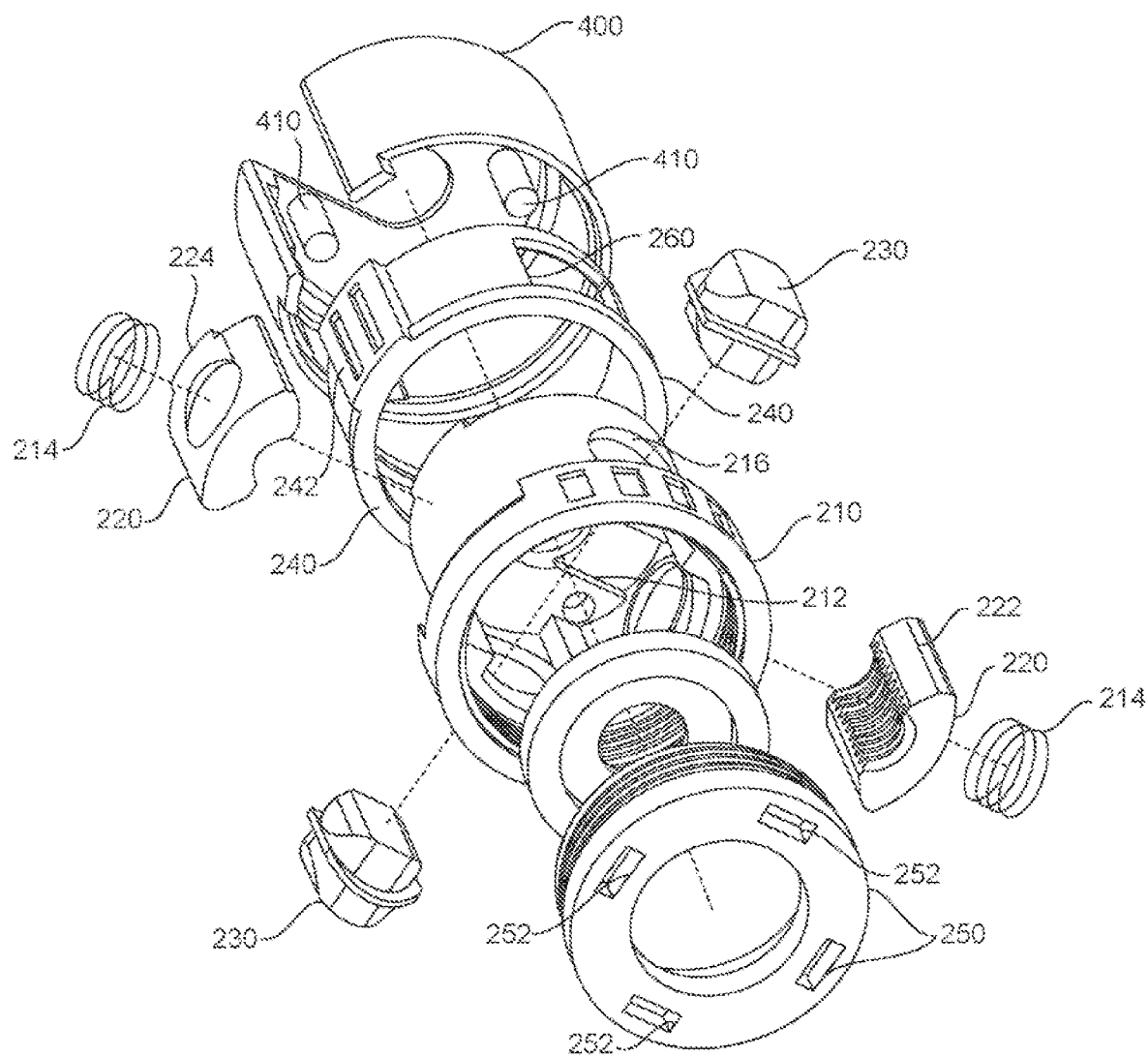
FIG. 5B illustrates an alternate, exploded, perspective view of the acute adjustment mechanism shown in FIG. 5A.

Referring to FIGS. 3A-3F and 5A-5B, the acute adjustment mechanism 200 will be described in greater detail. The channels 212 formed in the actuator body 210 that guide the path of the mobile jaws 220 and their springs 214 are illustrated in FIGS. 3E, 3F, and 5B. In the illustrated embodiment, the acute adjustment mechanism 200 includes first and second mobile jaws 220. In use, the first and second mobile jaws 220 are biased to couple with the threads of the threaded rod 120 by the springs 214. The mobile jaws 220 shown include threaded portions that interact with the threaded rod 120, but in other embodiments, mobile jaws may include other structure for interacting with the threaded rod including, for example, knurling, a softer material, or any other structure or material that is capable of interacting with the threads of the threaded rod 120. In use, the mobile jaws 220 may also be arranged and configured to interact with the disengagement members 230. For example, the mobile jaws 220 may include faces 222 that interact with surfaces 232 of the disengagement members 230. Apertures 216 (FIGS. 5A and 5B) formed in the sides of the actuator body 210 may constrain the two opposing disengagement members 230. In use, the disengagement members 230 are designed so that they can be pressed from outside of the actuator body 210 toward the threaded rod 120 so that when the disengagement members 230 are pressed inward, the mobile jaws 220 disengage from the threaded rod 120 enabling the strut length of the external fixation struts 100 to be adjusted acutely. For example, in one embodiment, the geometry of the disengagement members 230 inside of the actuator body 210 may be shaped like a wedge, although other suitable configurations are envisioned. The faces 232 of this wedge interact with the faces 222 of the mobile jaws 220 so that when the disengagement members 230 are pressed inward, the mobile jaws 220 move (e.g., separate and disengage) from the threaded rod 120 (FIG. 3F) enabling the threads formed on the mobile jaws 220 to be disengaged from the threads formed on the threaded rod 120 and thus enable the strut length to be adjusted acutely.

The mobile jaws 220 may be constrained within the actuator body 210 by the channel 212 formed in the actuator body 210 (FIGS. 3E, 3F, and 5B) so that translation toward and away from the threaded rod 120 is accomplished without any rotation. As previously mentioned, the external fixation strut 100 may also include a rotating sleeve 240 that fits over the outside of the actuator body 210 with openings 260 for providing access to the disengagement members 230. In use, rotating the sleeve 240 depresses the disengagement members 230 and locks the disengagement members 230 in the depressed position. Thus arranged, the rotating sleeve 240 allows for multiple struts to be adjusted acutely at once because the user is not required to keep the disengagement members 230 depressed by hand.

Figure 2:
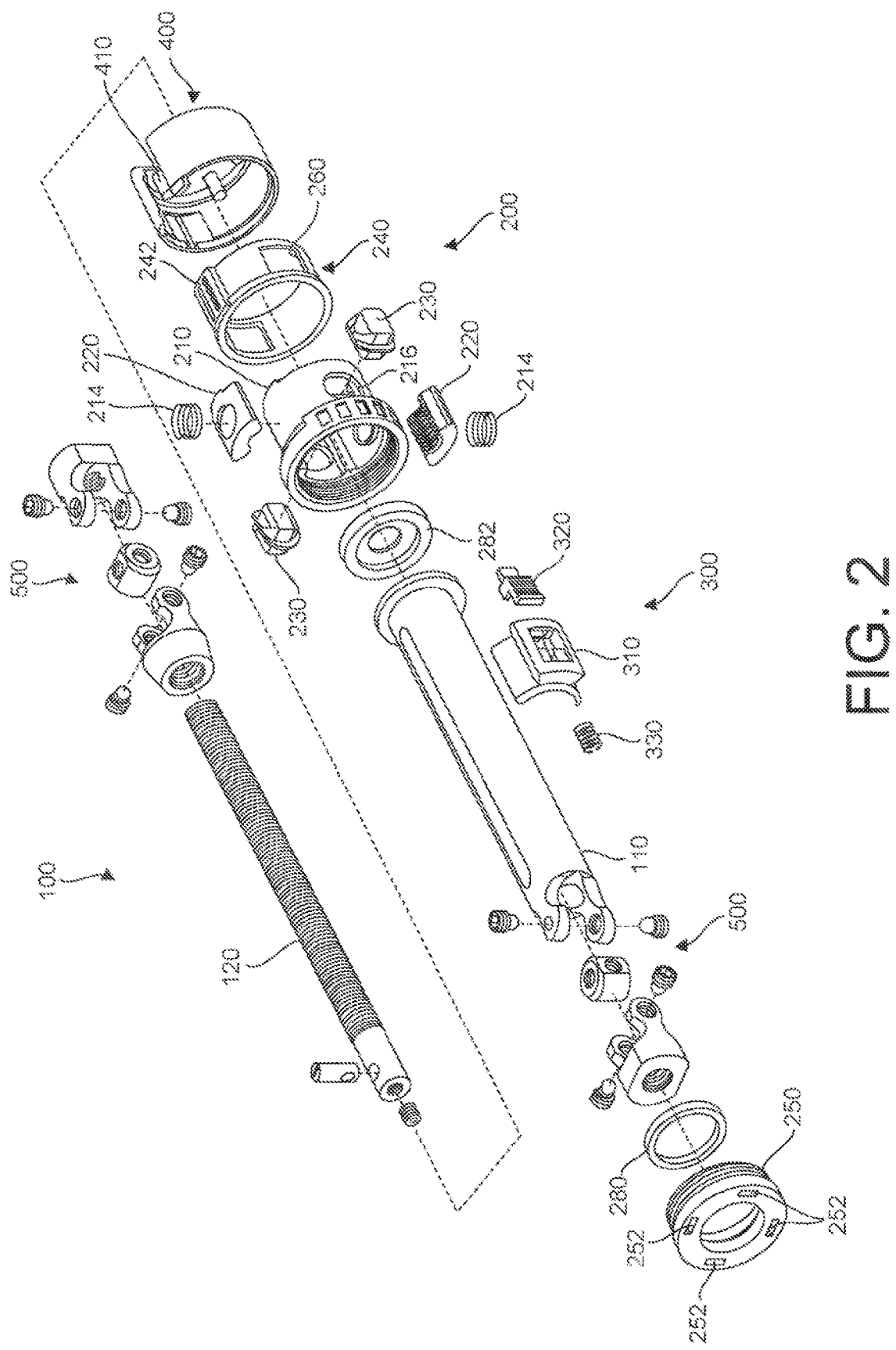
FIG. 2 illustrates an exploded, perspective view of the external fixation strut shown in FIG. 1A.

As previously mentioned, the external fixation strut 100 may also include a threaded collar 250. In use, the threaded collar 250 connects the actuator body 210 to the strut body 110. The threaded collar 250 may be slid up the base of the strut body 110 and threaded into the base of the actuator body 210. As shown, the acute adjustment mechanism 200 may also include a first washer 280 and a second washer 282 (FIG. 2). Washers 280, 282 may be positioned between the threaded collar 250 and the strut body 110, and between the strut body 110 and the actuator body 210. The washers 280, 282 act as spacers and reduce friction. The washer 282 between the strut body 110 and the actuator body 210 may also further constrain the mobile jaws 220 and disengagement members 230. The mobile jaws 220 may be constrained within the acute adjustment mechanism 200 by the channels 212. The channels 212 inside the actuator body 210 may correspond to (substantially match) a rectangular protrusion 224 (FIGS. 5A and 5B) on the top of the mobile jaws 220. In use, this constrains the mobile jaws 220 to translation toward and away from the threaded rod 120 and prevents the mobile jaws 220 from rotating out of position. Alternatively, the mobile jaws of some embodiments may have posts on the jaws that align with holes on the actuator body and the rotating sleeve.

Figure 4:
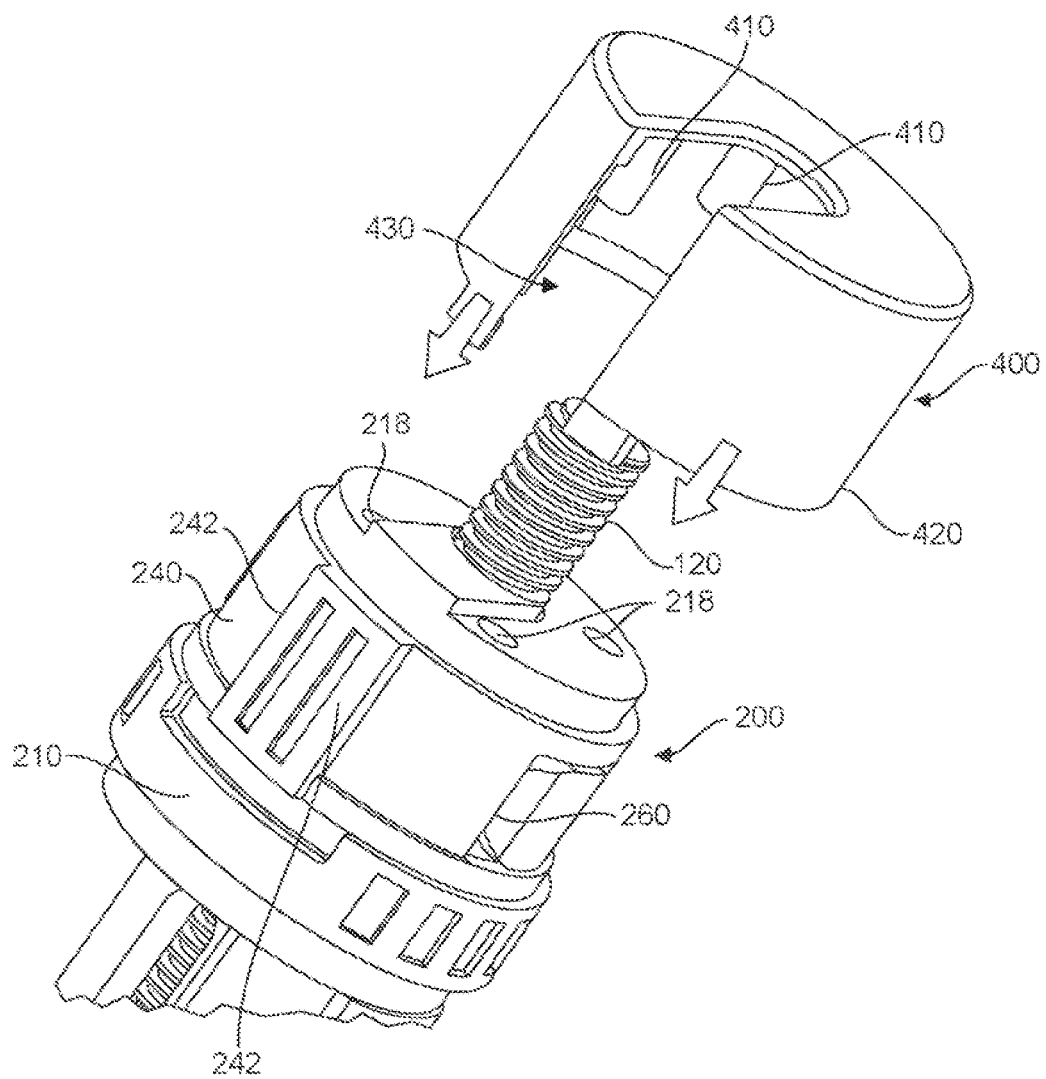
FIG. 4 illustrates an exploded, perspective view of an example of an embodiment of a band for use with the external fixation strut shown in FIG. 1A.

Referring to FIG. 4, as previously mentioned, the external fixation strut 100 may also include a band 400. In some embodiments, the bands 400 may be arranged and configured as an identification (ID) band for identifying each particular strut in the external fixation system. As such, the bands 400 may be provided to numerically identify strut assemblies so that each strut assembly may be distinguished for a prescription. In use, the bands 400 are coupled to the external fixation struts 100. For example, as shown, in one example of an embodiment, the band 400 may be slid down over the top of the actuator body 210 by the action arrows in FIG. 4. Pegs, projections, etc. 410 on the band 400 are sized and configured to be received by holes 218 formed in the actuator body 210. In use, the pegs, projections, etc. 410 prevent the mobile jaws 220 from disengaging from the threaded rod 120 when the band 400 is coupled to the actuator body 210. In the illustrated embodiment, the band 400 has a body 420 which covers the disengagement members 230 so that the buttons are not accessible when the band 400 is positioned over the actuator body 210. In some embodiments, the body 420 may include a space, a slot, a channel, or the like 430 to receive a tab, a projection, or the like 242 (FIGS. 5A and 5B) of the rotating sleeve 240.

The band 400 provides a safety feature and reduces the risk of inadvertent acute adjustment of the strut assembly by inhibiting access to the disengagement members 230 (e.g., inhibits accidental pressing of the buttons). Holes, pegs, and geometric features on the band, actuator body, and rotating sleeve may also or alternatively be used to provide easy placement of the band in the proper orientation. Acute adjustment generally takes place clinically during application of the external fixation frame or during strut changeouts. The bands 400 may be helpful to avoid inadvertent acute adjustment when a patient is adjusting struts using precise adjustment mechanisms to comply with an adjustment prescription such as, for example, when adjusting the struts at home utilizing a precise adjustment mechanism to comply with the prescription.

Figure 1B:
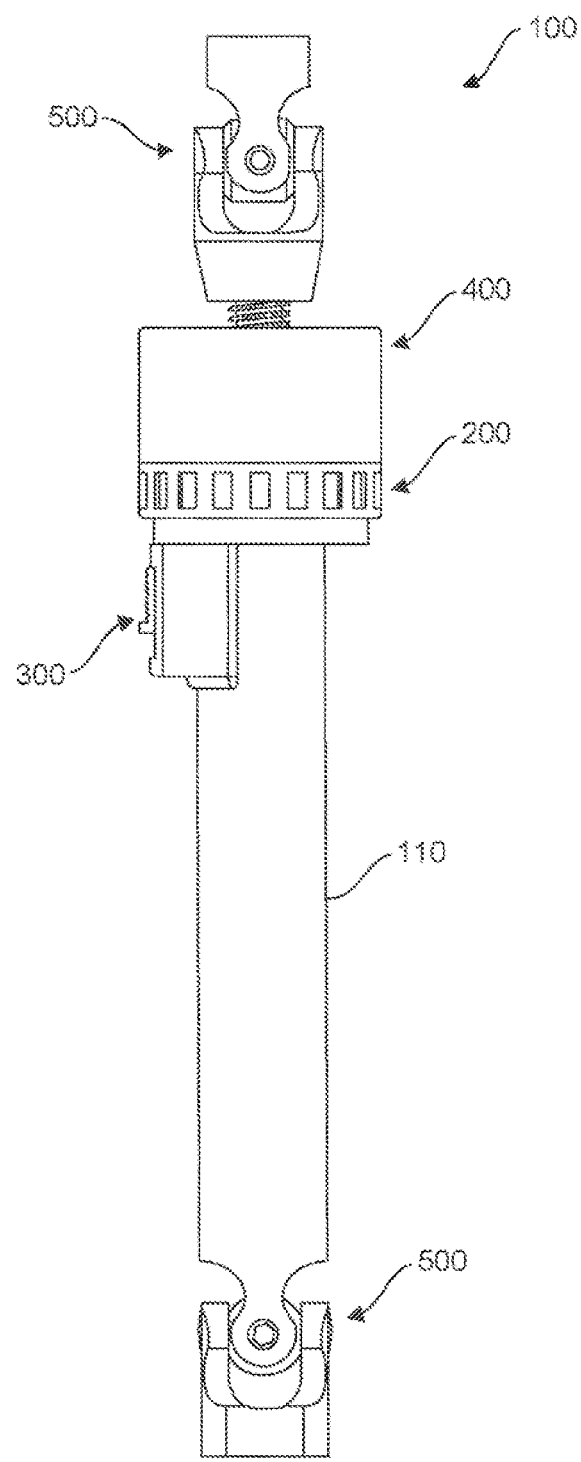
FIG. 1B illustrates a back elevation view of the external fixation strut shown in FIG. 1A.
Figure 1C:
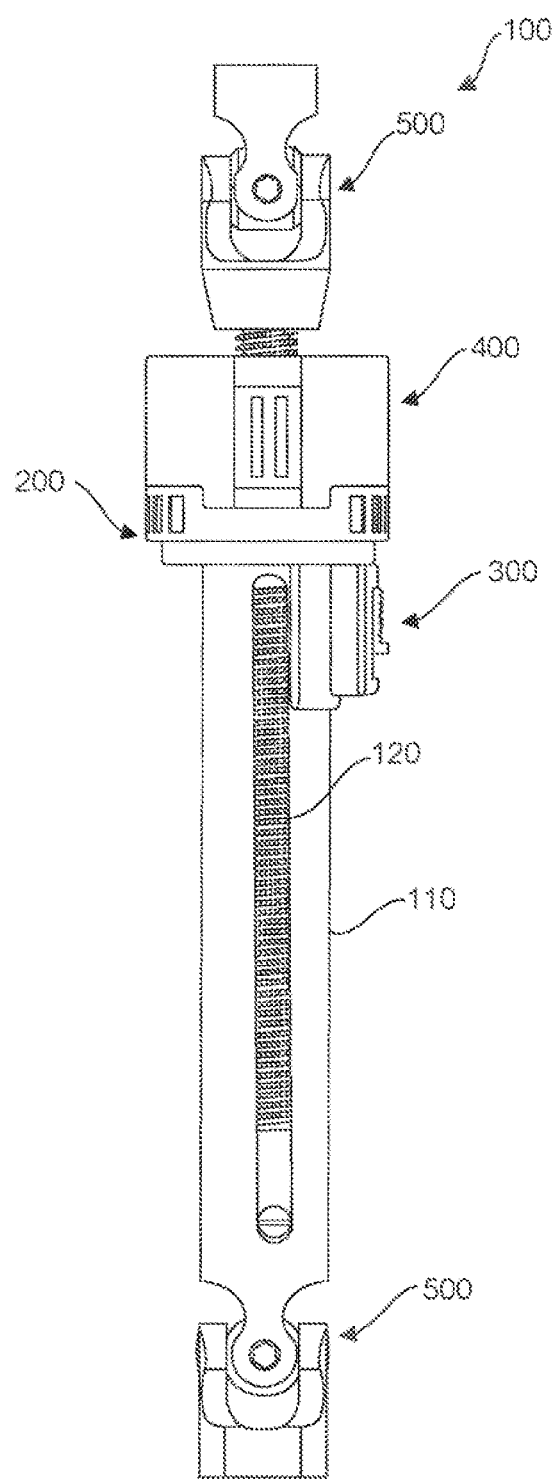
FIG. 1C illustrates a front elevation view of the external fixation strut shown in FIG. 1A.
Figure 6A:
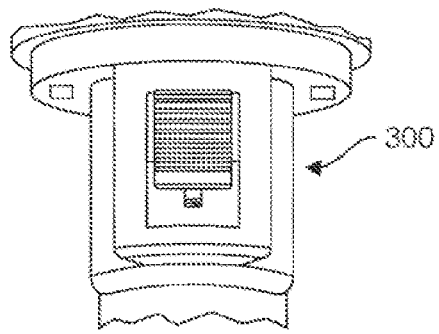
FIG. 6A illustrates a side elevation view of an example of an embodiment of a precise adjustment mechanism that may be used in combination with the external fixation strut shown in FIG. 1A, the precise adjustment mechanism including a plunger positioned in a locked position.
Figure 6B:
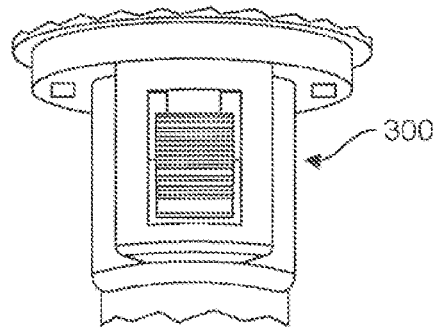
FIG. 6B illustrates a side elevation view of the precise adjustment mechanism shown in FIG. 6A, the precise adjustment mechanism including the plunger positioned in an unlocked position.
Figure 6C:
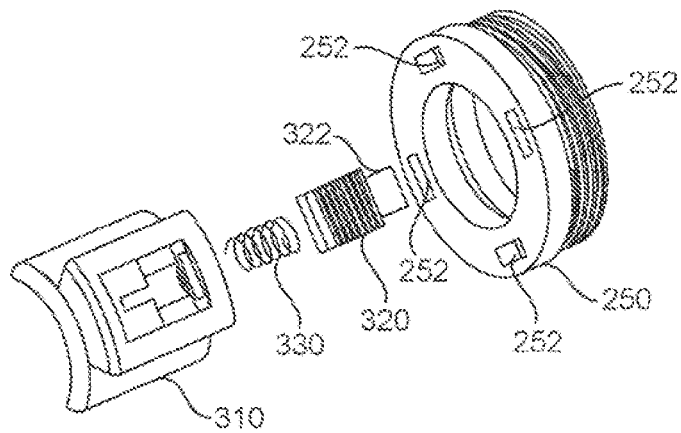
FIG. 6C illustrates an exploded, perspective view of the precise adjustment mechanism shown in FIG. 6A and a portion of the acute adjustment mechanism shown in FIG. 5B.
Figure 7A:
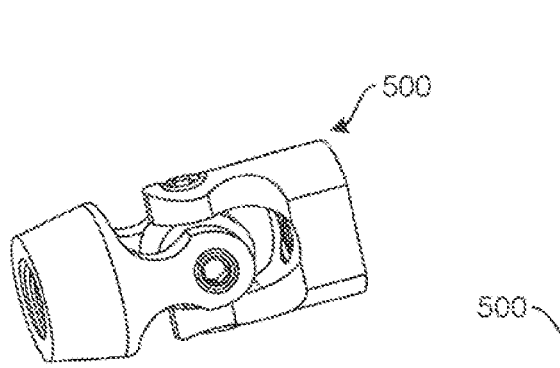
FIG. 7A illustrates a perspective view of an example of an embodiment of a universal joint that may be used in combination with an external fixation strut.
Figure 7B:
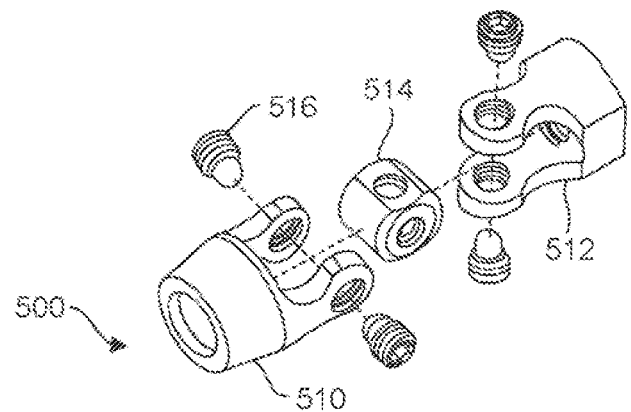
FIG. 7B illustrates an exploded, perspective view of the universal joint shown in FIG. 7A.

Referring to FIGS. 6A-6C, the precise adjustment mechanism 300 will be described in greater detail. As will be described in greater detail, the precise adjustment mechanism 300 enables the strut length of the external fixation struts 100 to be adjusted. For example, as previously mentioned, the precise adjustment mechanism 300 may be used by patients during daily adjustments. As shown, in one example of an embodiment, the precise adjustment mechanism 300 includes a body 310, a plunger 320, and a spring 330. The precise adjustment mechanism 300 may be fixed to the strut body 110 in a position that does not interfere with the adjustment scale and, in one embodiment, may be positioned underneath the threaded collar 250 as generally shown in FIGS. 1A-1C. In use, the spring 330 biases the plunger 320 so that the plunger 320 extends beyond an outer edge of the body 310 and into the cavity 252 of the threaded collar 250. Thus arranged, the precise adjustment mechanism 300 cannot turn as long as the plunger 320 is positioned within the cavity 252 of the threaded collar 250. Moving the plunger 320 from its first position to a second position so that the plunger 320 no longer engages the threaded collar 250 allows the precise adjustment mechanism 300 to be turned, advancing or retrieving the threaded rod 120 relative to the strut body 110 and hence adjusting the length of the external fixation strut 100. The number and spacing of cavities 252 in the base of the threaded collar 250 defines the resolution of precise adjustment. For example, four equally spaced cavities 252 with an assembly that advances one millimeter per full turn provides tactile feel and hard stops every quarter of a turn of adjustment, which are one-quarter millimeter linear adjustment increments. When fully assembled, the threaded collar 250 turns with the actuator body 210 as one assembly. In other embodiments, the body 310, or a similar component, may be coupled to the strut body and notches, openings, or other mechanisms may be located on the actuator body.

In one example of an embodiment, as will be described in greater detail, the external fixation struts 100 may be coupled to first and second rings, bases, etc. (used interchangeably without the intent to limit), as will be appreciated by one of ordinary skill in the art. The external fixation struts 100 may be coupled to the bases by any suitable connectors, mechanisms, or the like now known or hereafter developed. For example, referring to FIGS. 7A and 7B, U-joints 500 may be used. Alternatively however, as previously mentioned, any other now known or hereafter developed connector can be used such as, for example, ball joints, threaded ends, etc. In one example of an embodiment, each of the U-joints 500 may be constructed of two joint devises 510, 512, a central body 514, and set screws 516. The set screws 516 connect the central body 514 to the joint devises 510, 512 and reduce the slope of the joints. That is, one or more of the U-joints for coupling the external fixator struts may include first and second clevis components 510, 512, each clevis component 510, 512 having a threaded bore for receiving a fastener for coupling the first and second clevis components 510, 512 to, for example, the external fixator strut and the base, ring, etc. In addition, the one or more of the U-joints may include a central body or bushing 514 having a plurality of openings such as, for example, threaded openings for receiving a plurality of screws such as, for example, set screws, ball end screws, etc. for coupling the central body or bushing 514 to the first and second clevis components 510, 512.

Figure 8A:
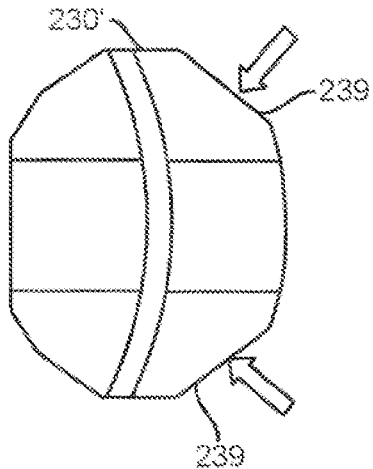
FIG. 8A illustrates a top plane view of an example of an embodiment of an angled button that may be in combination with the external fixation strut shown in FIG. 1A.
Figure 8B:
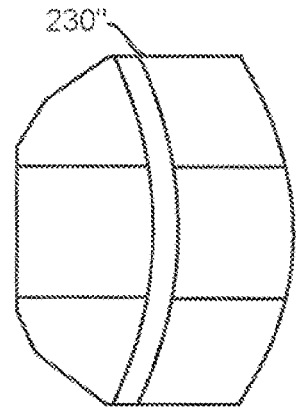
FIG. 8B illustrates a top plane view of an example of an embodiment of a rounded button that may be in combination with the external fixation strut shown in FIG. 1A.

Alternative embodiments of the disengagement members, labelled 230' and 230", are depicted in FIGS. 8A and 8B. The disengagement member 230' shown in FIG. 8A has angled exterior surfaces 239 so that both disengagement members 230' may be depressed by portions of the rotating sleeve 240 as the rotating sleeve 240 is rotated relative to the actuator body 210. As seen in FIG. 8B, the disengagement member 230" may be designed without the angled exterior surfaces, thus requiring the disengagement members be depressed before the sleeve 240 can be rotated relative to the actuator body 210.

Figure 9A:
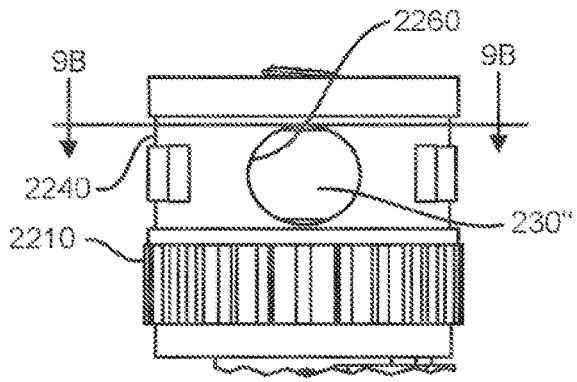
FIGS. 9A and 9B illustrate an example of an embodiment of an external fixation strut with the rounded button of FIG. 8B, the rounded button illustrated in a non-activated or non-pushed position, and consequently the acute adjustment mechanism is engaged with the threaded rod.
Figure 9B:
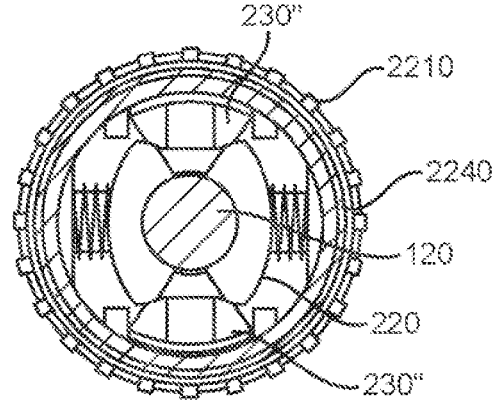
Figure 9C:
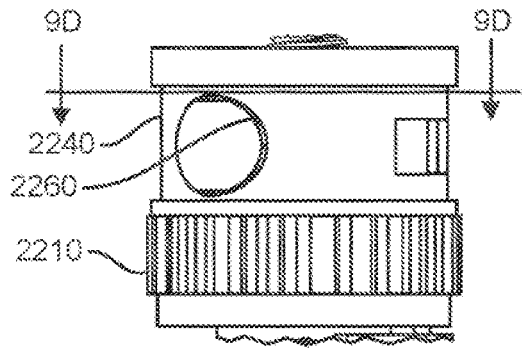
FIGS. 9C and 9D illustrate an example of an embodiment of an external fixation strut with the rounded button of FIG. 8B, the rounded button illustrated in an activated or pushed position, and consequently, the acute adjustment mechanism is disengage with the threaded rod, and additionally the rotating sleeve has been rotated.
Figure 9D:
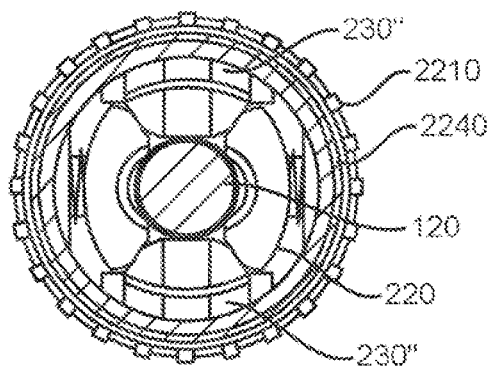

As shown in FIGS. 9A-9D, an alternative embodiment of the acute adjustment mechanism may have an alternative actuator body 2210 with a different gripping surface and an alternative rotating sleeve 2240 with round openings 2260 rather than rectangular openings. The alternative actuator body 2210 is shown in use with disengagement members 230". In FIGS. 9A and 9B, the rotating sleeve 2240 is shown with its openings 2260 aligned with disengagement members 230" to allow the mobile jaws 220 to be pushed against the spring bias and engaged with the threaded rod 120. As shown in FIGS. 9C and 9D, the rotating sleeve 2240 is moved rotationally to block outward travel of the disengagement members 230" and hold the disengagement members 230" in a pushed state that disengages the mobile jaws 220 from the threaded rod 120.

Figure 10:
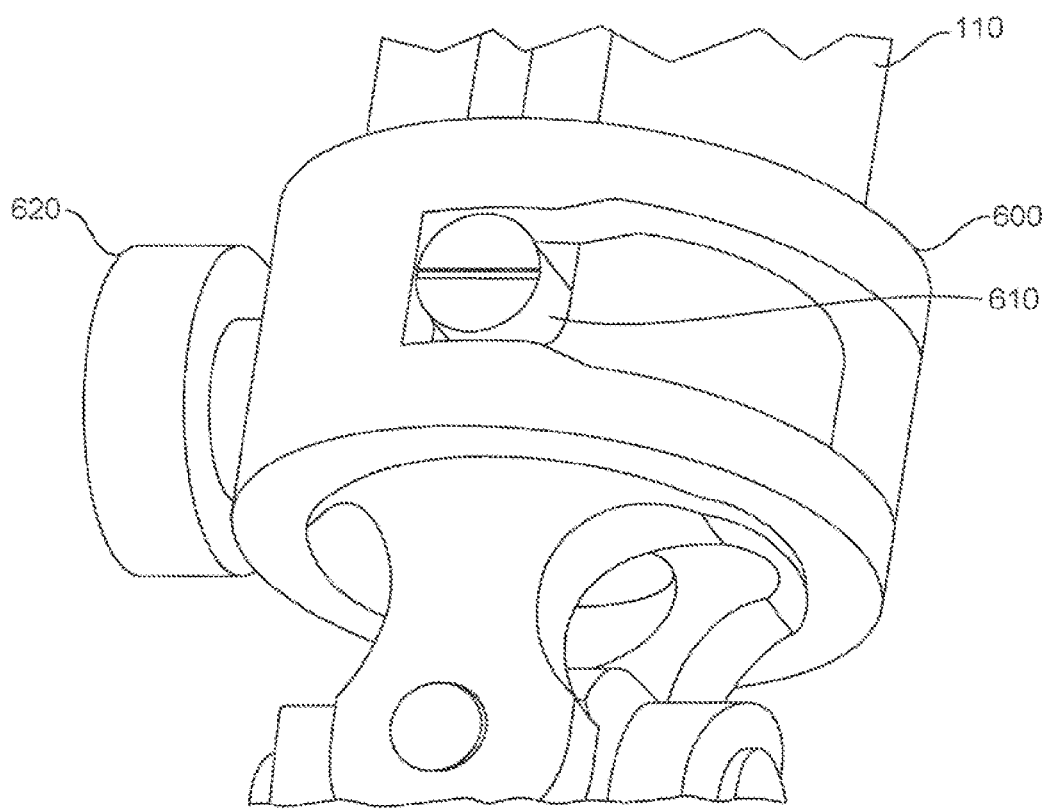
FIG. 10 illustrates a perspective view of an example of an embodiment of a locking sleeve coupled to the external fixation strut shown in FIG. 1A.
Figure 11A:
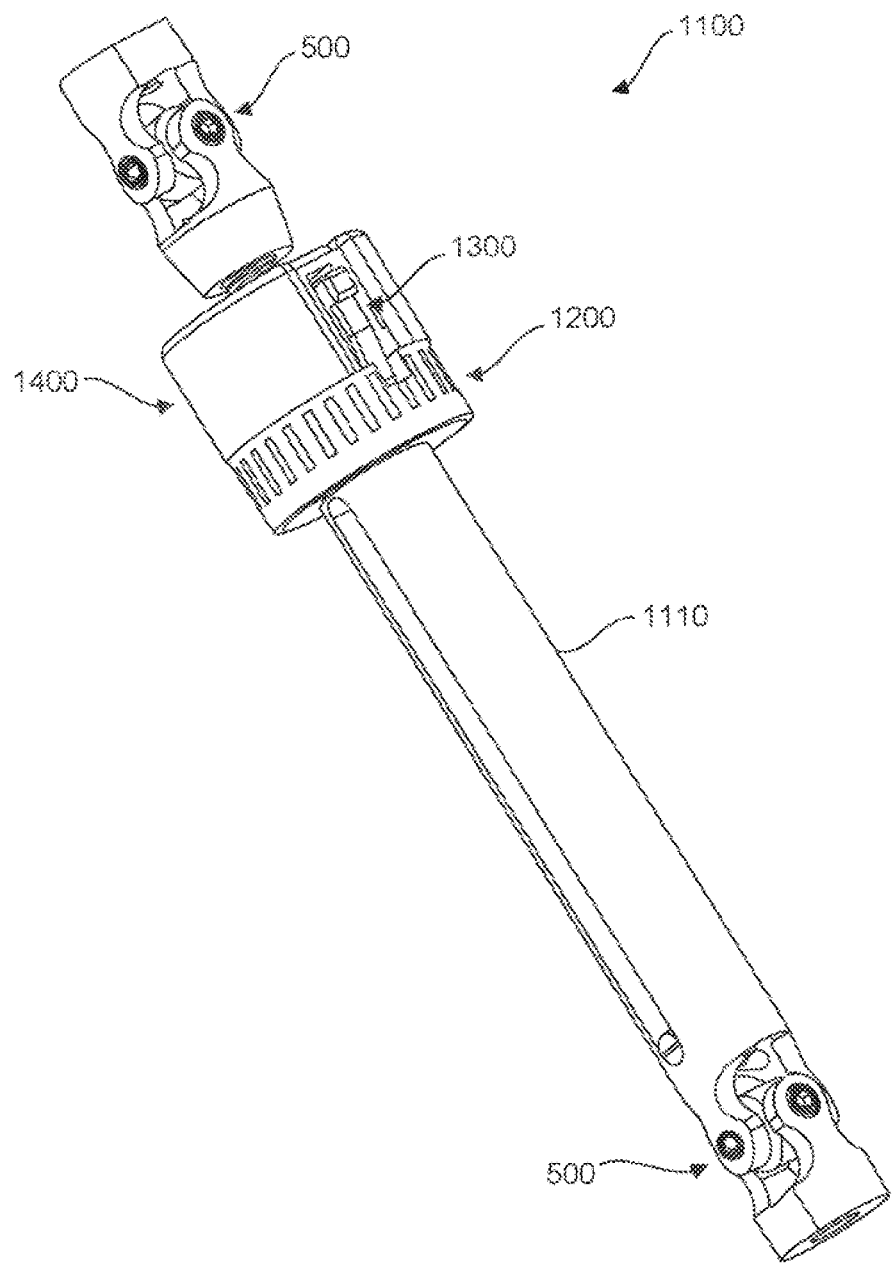
FIG. 11A illustrates a perspective view of an alternate example of an external fixation strut in accordance with principles of the present disclosure.
Figure 11B:
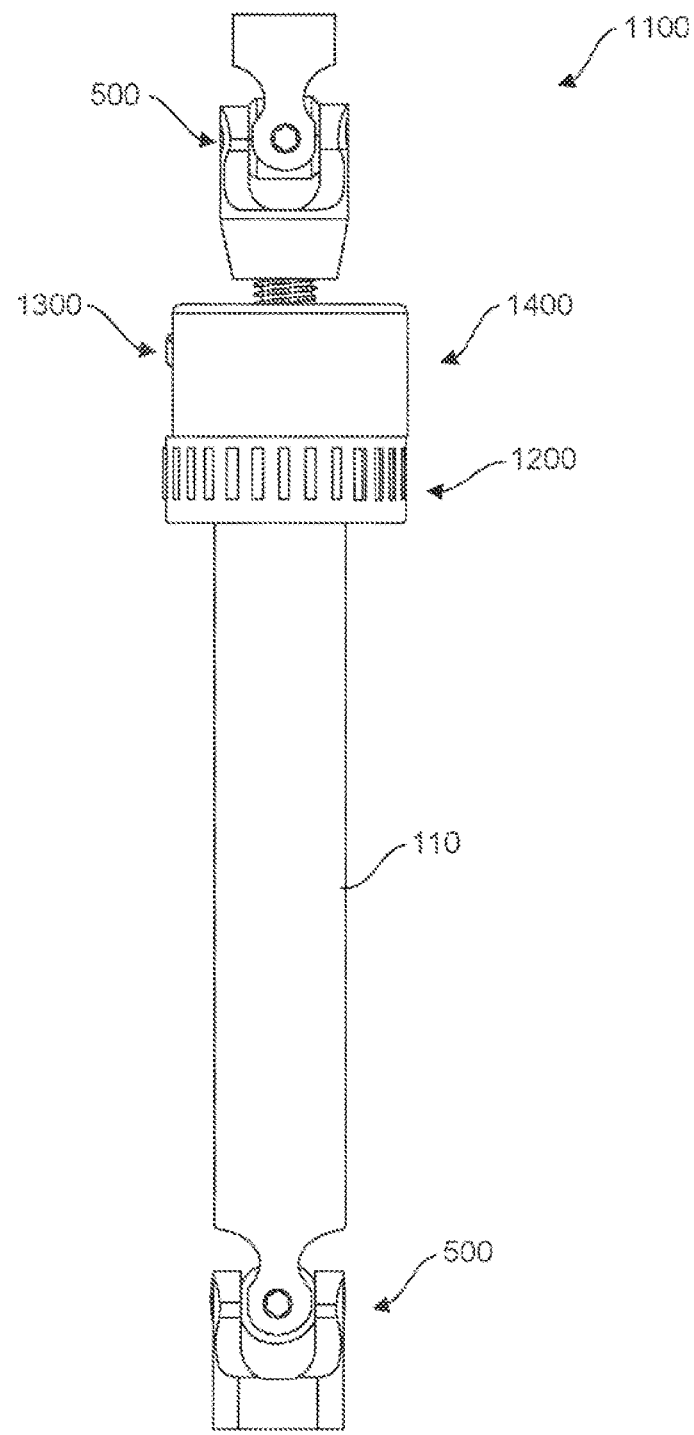
FIG. 11B illustrates a back elevation view of the external fixation strut shown in FIG. 11A.
Figure 11C:
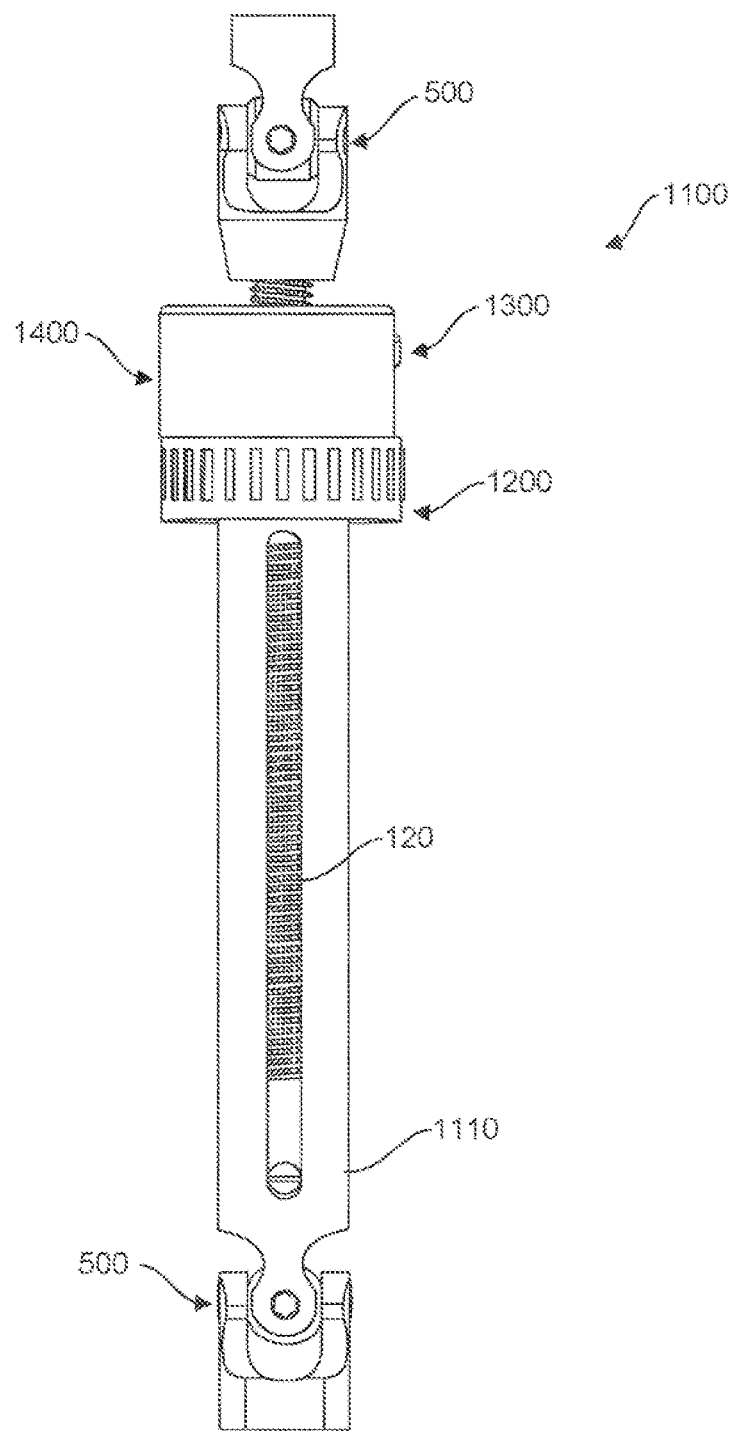
FIG. 11C illustrates a front elevation view of the external fixation strut shown in FIG. 11A.

Referring to FIG. 10, in one example of an embodiment, the external fixation strut 100 may also include a locking sleeve 600. In use, incorporation of the locking sleeve 600 may assist with preventing accidental adjustment for any of the fixation strut embodiments disclosed herein. In this embodiment of the locking sleeve, adjustment would be limited to motion of a tracer pin 610 with the locking sleeve 600 coupled around the strut body 110. The locking sleeve 600 may be held in place at the desired level with a bolt 620 that may be engaged with the side of the strut body 110. This prevents the strut 100 from adjusting but does not take up any adjustment range of the threaded rod 120. That is, in one example of an embodiment, the a tracer pin 610 may be operatively coupled to the threaded rod 120. The tracer pin 610 can be coupled to the threaded rod 120 by any now known or hereafter developed mechanism including, for example, adhesive, welding, fasteners, integrally formed, etc. The locking sleeve 600 may be operatively and selectively coupled to the strut body 110 by any now known or hereafter developed mechanism such as, for example, bolt 620. The locking sleeve 600 includes an opening, cavity, or the like, arranged and configured to receive the tracer pin 610. In use, the locking sleeve 600 is arranged and configured to prevent movement of the track pin 610 and thus to prevent adjustment of the external fixation strut.

As previously mentioned, in use, the external fixation strut 100 may be a part of an external fixation system that includes an upper base, a lower base, and multiple struts between the upper base and the lower base. At least one of the struts may be the external fixation strut 100 or one of the other fixation struts disclosed herein. In some embodiments, the system includes six struts coupled between the upper base and the lower base and at least one of the six struts is the external fixation strut 100, but in other embodiments may include systems with fewer or more struts than six. Any of the struts described herein may also include one or more telescoping bodies that translate relative to one another to change the overall length of the strut. The system may also include connectors for coupling with one or both of the upper base and the lower base. For example, the connectors may include the universal joints 500 and further may include fasteners between the universal joints 500 and the bases. System embodiments may also include bone fixation mechanisms for coupling between the connectors or the bases and tissue of a patient. Such bone fixation mechanisms may be any now known or hereafter developed bone fixation members including, for example, wires (threaded and unthreaded), k-wires, pins, and screws.

Referring to FIGS. 11A-16, an alternate example of an embodiment of an external fixation strut 1100 is disclosed. As will be described herein, external fixation strut 1100 may be substantially similar to external fixation strut 100 except as noted herein. As shown in the example embodiment, the external fixation strut 1100 includes a strut body 1110, a threaded rod 120 substantially rotationally fixed relative to the strut body 1110 so that movement of the threaded rod 120 axially translates or moves the threaded rod 120 relative to the strut body 1110, an acute adjustment mechanism 1200 selectively disengageable from threads of the threaded rod 120, and a precise adjustment mechanism 1300.

In one example of an embodiment, the acute adjustment mechanism 1200 includes an actuator body 1210 that includes a threaded collar 1250 (FIGS. 12 and 14B), a spring-loaded mobile jaw 1220 including associated biasing springs 1214, and one or more disengagement members 1230 that are configured to interact with the mobile jaw 1220. The actuator body 1210 includes one or more apertures 1216 (FIGS. 13C and 14A) to receive at least a portion of the one or more disengagement members 1230, respectively (e.g., as shown, the acute adjustment mechanism 1200 may include one disengagement member 1230 and one aperture 1216). The disengagement member 1230 may be in the form of shown is a button capable of translation toward the center of the device and rotation about its axis, but other embodiments are envisioned including, for example, one or more wedges, screws, cams, or any other mechanism now known or hereafter developed.

In the illustrated embodiment, the threaded collar 1250 is arranged and configured to couple the actuator body 1210 to the strut body 1110. In one example of an embodiment, the actuator body 1210 may include one or more channels 1212 (FIG. 16) to guide the path of the mobile jaws 1220 and the associated springs 1214. In use, the associated springs 1214 bias the mobile jaws 1220 against the threaded rod 120 and toward the disengagement member 1230. For example, the mobile jaws 1220 may include faces 1222 that interact with surfaces 1232 of the disengagement member 1230 so that when the disengagement member 1230 is pressed inward, the mobile jaws 1220 move (e.g., separate and disengage) from the threaded rod 120 so that the strut length of the external fixation strut 1100 can be adjusted acutely.

In one example of an embodiment, as shown, the precise adjustment mechanism 1300 includes a body 1310, a pivot pin 1340, and a spring 1330. The spring 1330 biases the body 1310 about the pivot pin 1340 to an engaged position toward a notch 1180 (FIG. 15C) in the strut body 1110. In use, the actuator body 1210 is inhibited from moving (e.g., turning) relative to the strut body 1110 as long as a portion of the body 1310 is seated in the notch 1180.

In one example of an embodiment, as shown, the external fixation strut 1100 may also include bands 1400, as described herein. In addition, and/or alternatively, the external fixation strut 1100 may also include and one or more connectors 500 to couple the external fixation strut 1100 to one or more bases. As shown, and as previously mentioned, the connectors 500 may be in the form of a U-joint, alternatively however any other now known or hereafter developed connector can be used such as, for example, ball joints, threaded ends, etc.

In the illustrated embodiment, the mobile jaws 1220 are biased to couple with the threads of the threaded rod 120 by the springs 1214. The mobile jaws 1220 shown include threaded portions that interact with the threaded rod 120, but in other embodiments, mobile jaws may include other structure for interacting with the threaded rod including, for example, knurling, a softer material, or any other structure or material that is capable of interacting with the threads of the threaded rod 120. In use, the mobile jaws 1220 are arranged and configured to interact with the disengagement members 1230. For example, the mobile jaws 1220 may include faces 1222 that interact with surfaces 1232 of the disengagement member 1230. Aperture 1216 formed in the side of the actuator body 1210 may constrain the disengagement member 1230. In use, the disengagement member 1230 is designed so that it can be pressed from outside of the actuator body 1210 toward the threaded rod 120 so that when the disengagement member 1230 is pressed inwards, the mobile jaws 1220 disengage from the threaded rod 120 enabling the strut length of the external fixation strut 100 to be adjusted acutely. For example, in one embodiment, the geometry of the disengagement member 1230 inside of the actuator body 1210 may be shaped like a wedge, although other suitable configurations are envisioned. The faces 1232 of this wedge interact with the faces 1222 of the mobile jaws 1220 so that when the disengagement member 1230 is pressed inward, the mobile jaws 1220 move (e.g., separate and disengage) from the threaded rod 120 (FIGS. 13E-14B) enabling the threads to be disengaged and hence the strut length to be adjusted acutely. As shown in the progression between FIGS. 13D and 13E and with the action arrows in FIG. 13E, the mobile jaws 1220 are configured to pivot away from the threaded rod 120 when sufficiently interacted with by the disengagement member 1230.

The mobile jaws 1220 may be constrained within the actuator body 1210 by the channels 1212 (FIG. 16) so that pivoting toward and away from the threaded rod 120 is accomplished along a designated path. As shown in the progression between FIG. 13E and FIGS. 14A-14B, the disengagement member 1230 is configured to be rotated about its longitudinal axis to engage tabs 1233 behind a portion of the actuator body 1210 when the disengagement member 1230 has been pressed toward the threaded rod 120. By rotating multiple disengagement members on multiple external fixation struts in this manner, multiple external fixation struts can be adjusted acutely at once because the user is not required to keep the disengagement member 1230 depressed by hand.

Figure 12:
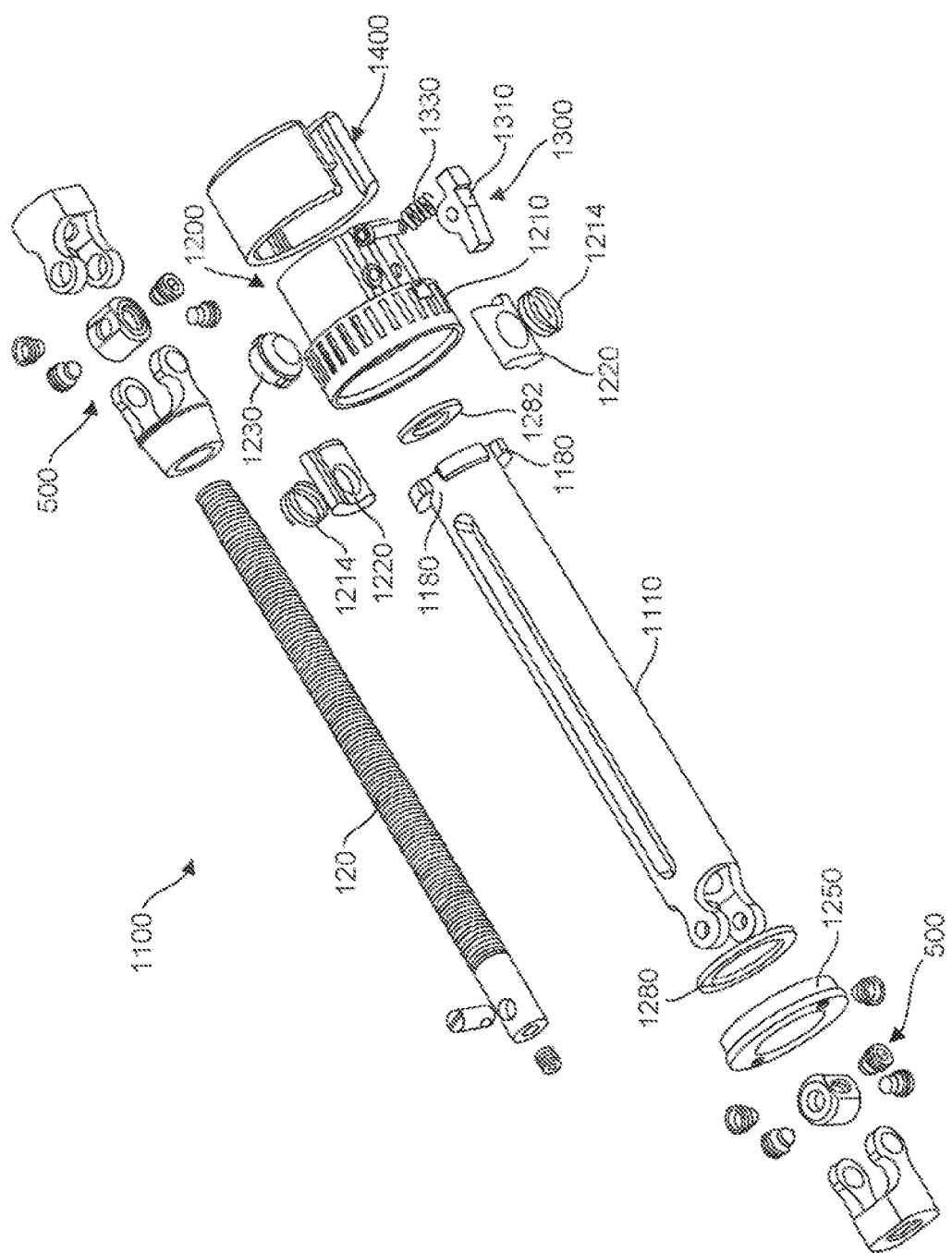
FIG. 12 illustrates an exploded, perspective view of the external fixation strut shown in FIG. 11A.
Figure 14A:
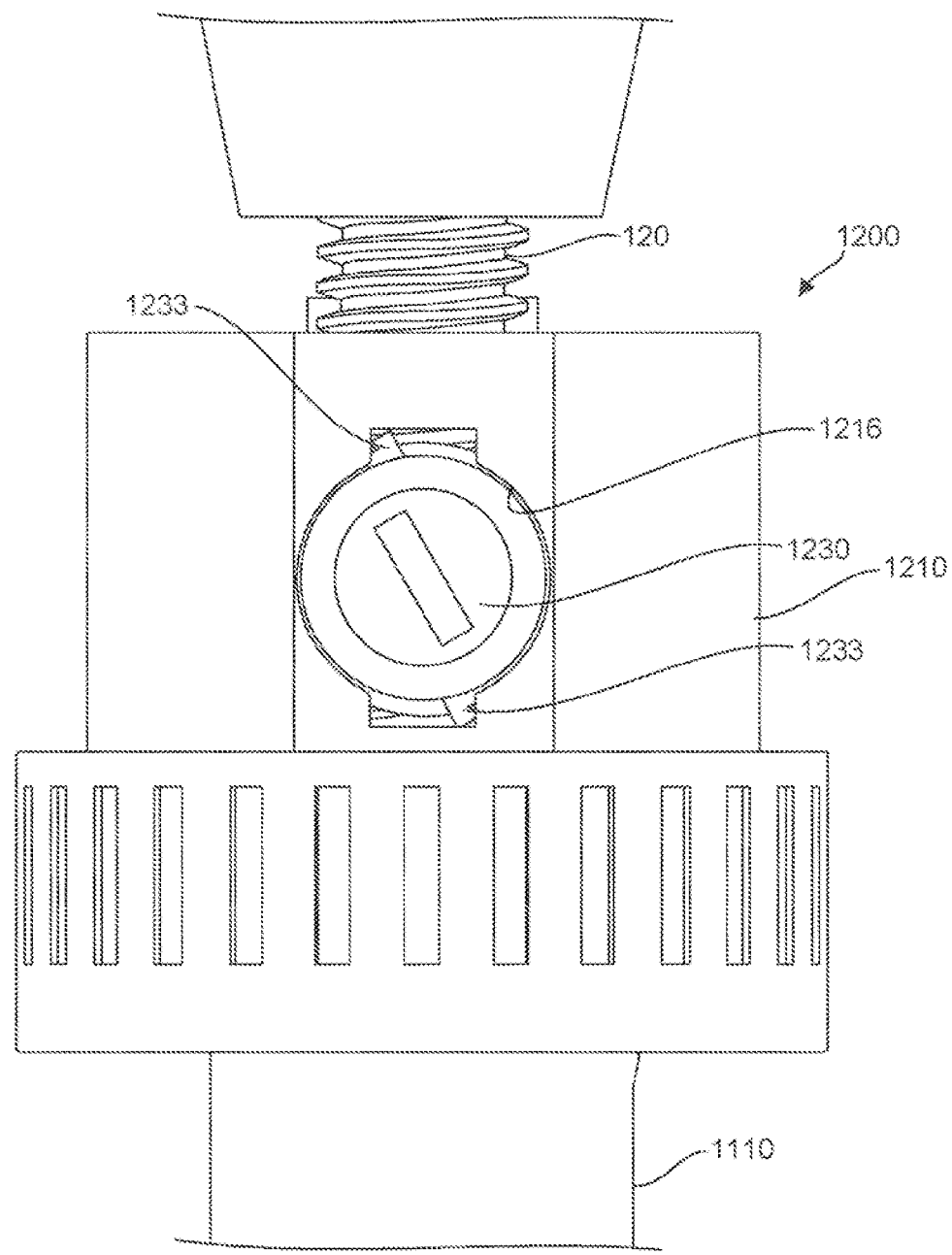
FIG. 14A is a side elevation view of the acute adjustment mechanism shown in FIG. 13E with the button rotated counterclockwise, as well as pushed.
Figure 14B:
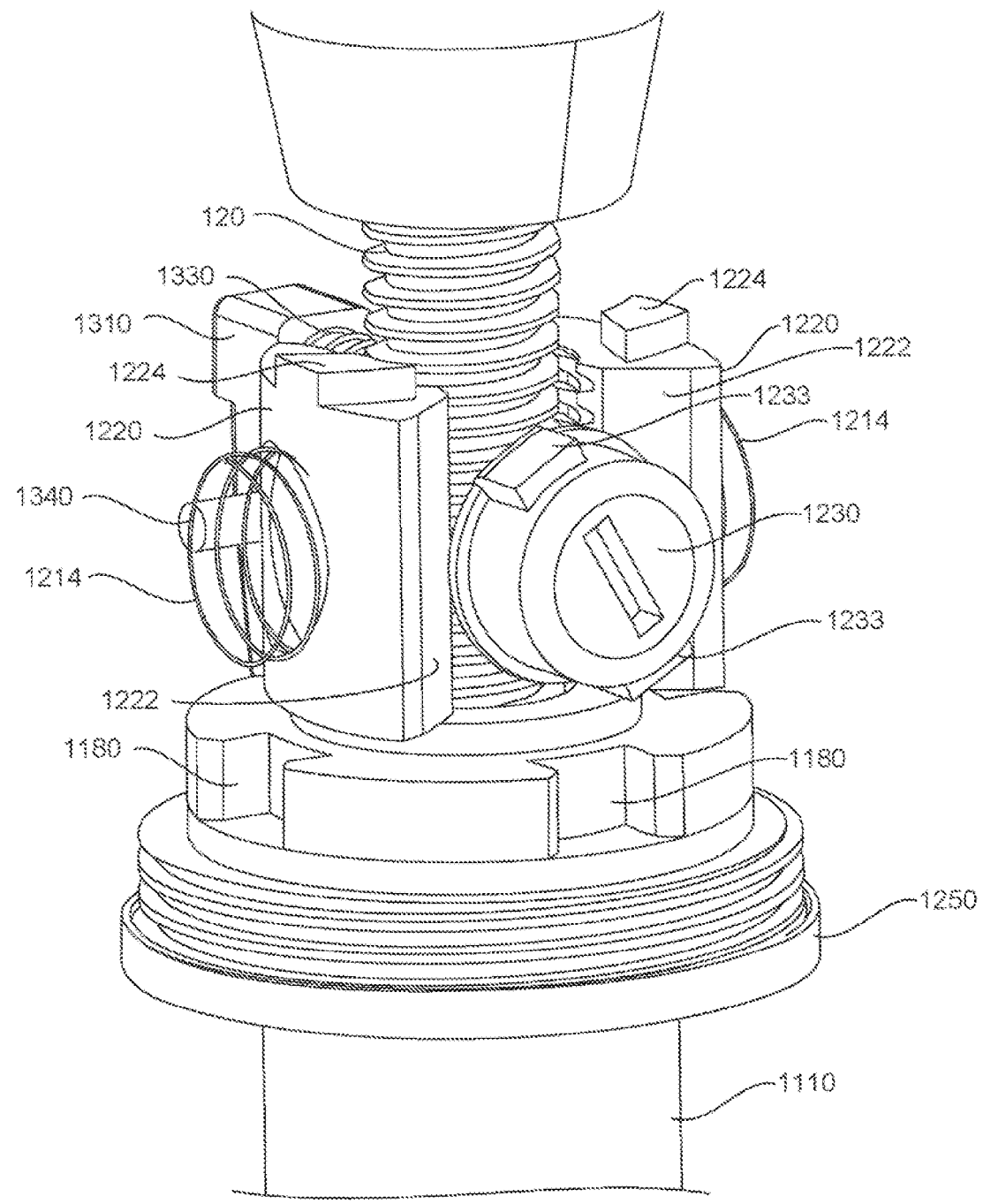
FIG. 14B is a perspective view of the acute adjustment mechanism shown in FIG. 14A with the actuator body of the device removed to view internal components of the mechanism.
Figure 16:
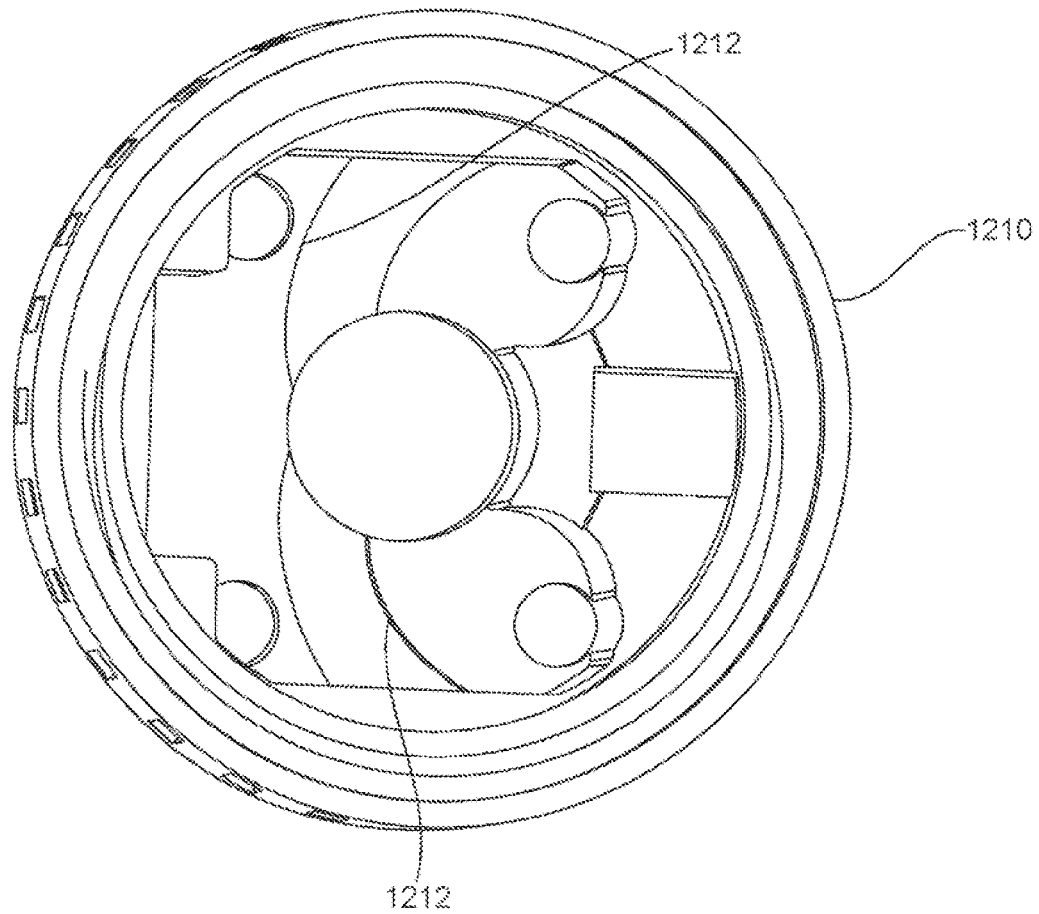
FIG. 16 is a perspective view of an interior portion of the acute adjustment mechanism shown in FIG. 15A.

As previously mentioned, the external fixation strut 1100 may also include a threaded collar 1250 (FIGS. 12 and 14B). In use, the threaded collar 1250 connects the actuator body 1210 to the strut body 1110. The threaded collar 1250 may be slid up the base of the strut body 1110 and threaded into the base of the actuator body 1210. As shown, the acute adjustment mechanism 1200 may also include a first washer 1280 and a second washer 1282 (FIG. 12). Washers 1280, 1282 (FIG. 12) may be positioned between the threaded collar 1250 and the strut body 1110, and between the strut body 1110 and the actuator body 1210. The washers 1280, 1282 act as spacers and reduce friction. The washer 1282 between the strut body 1110 and the actuator body 1210 may also further constrain the mobile jaws 1220 and disengagement member 1230. In the illustrated embodiment, the mobile jaws 1220 may be constrained within the acute adjustment mechanism 1200 by the channels 1212 (FIG. 16). Each of the channels 1212 inside the actuator body 1210 may correspond to (e.g., match) a protrusion 1224 (FIGS. 14B, 15C, and 15E) on the top of the mobile jaws 1220. Thus arranged, rotation of the mobile jaws 1220 is guided toward and away from the threaded rod 120 and prevents the mobile jaws 1220 from moving out of position. Alternatively, jaws of some embodiments may have posts on the jaws that align with holes on the actuator body and the rotating sleeve.

Figure 13A:
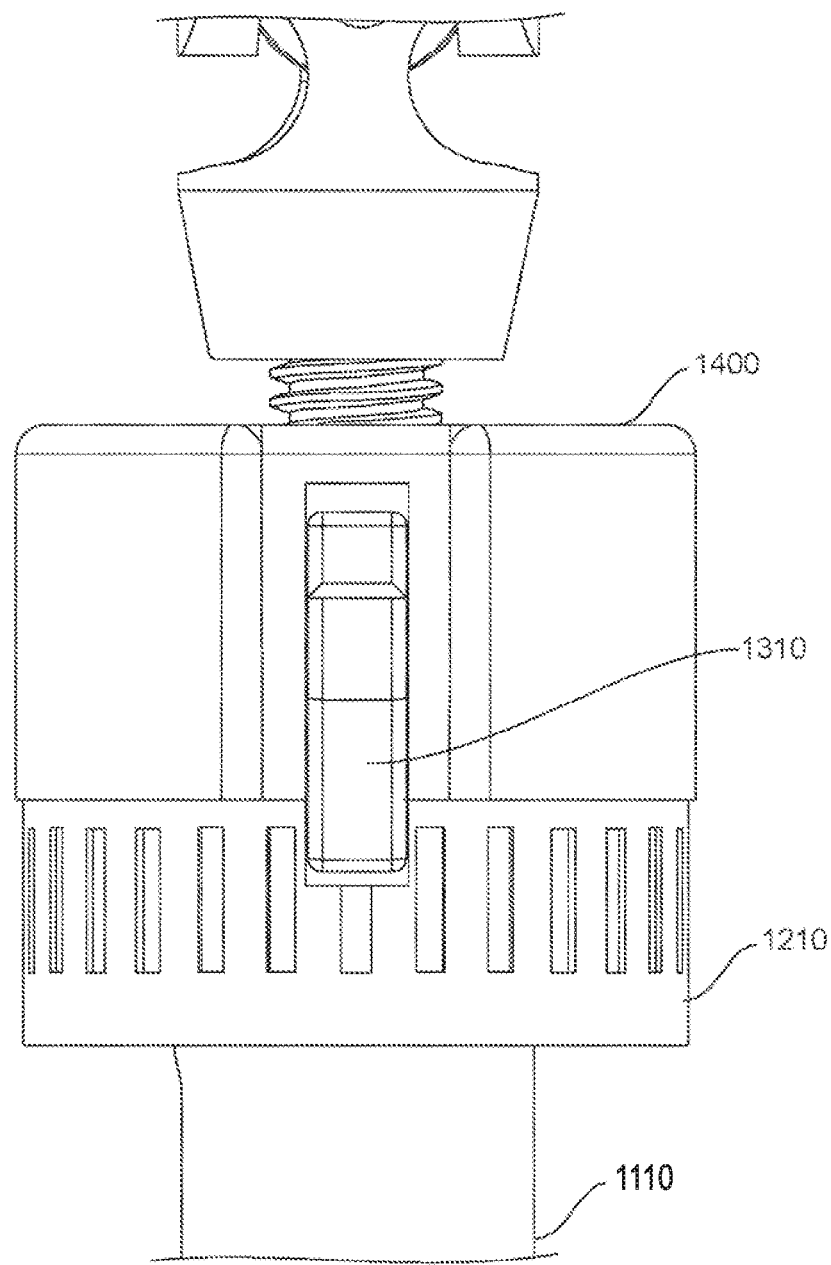
FIG. 13A illustrates a side elevation view of an example of an embodiment of an acute adjustment mechanism that can be used in combination with the external fixation strut shown in FIG. 11A.
Figure 13B:
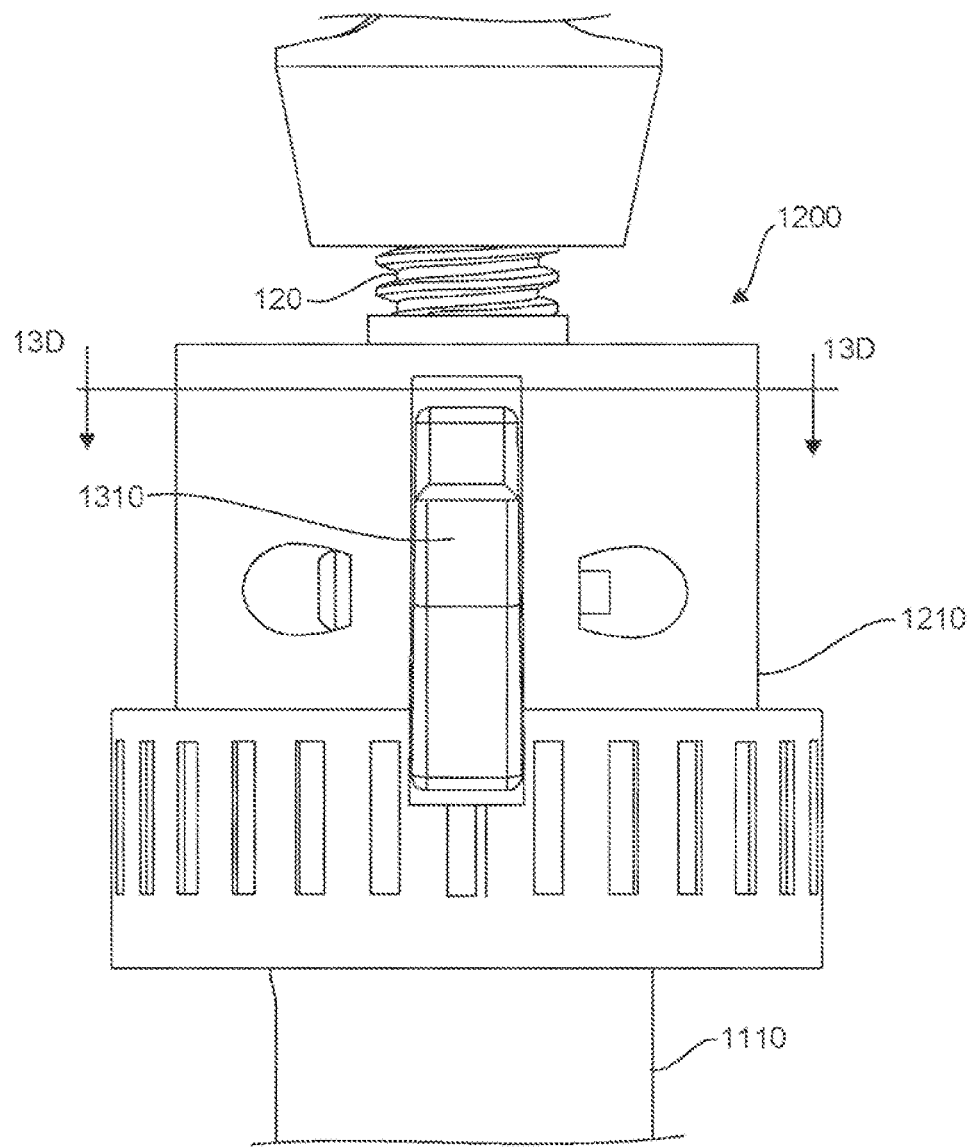
FIG. 13B illustrates a side elevation view of the acute adjustment mechanism shown in FIG. 13A with a band removed.
Figure 13C:
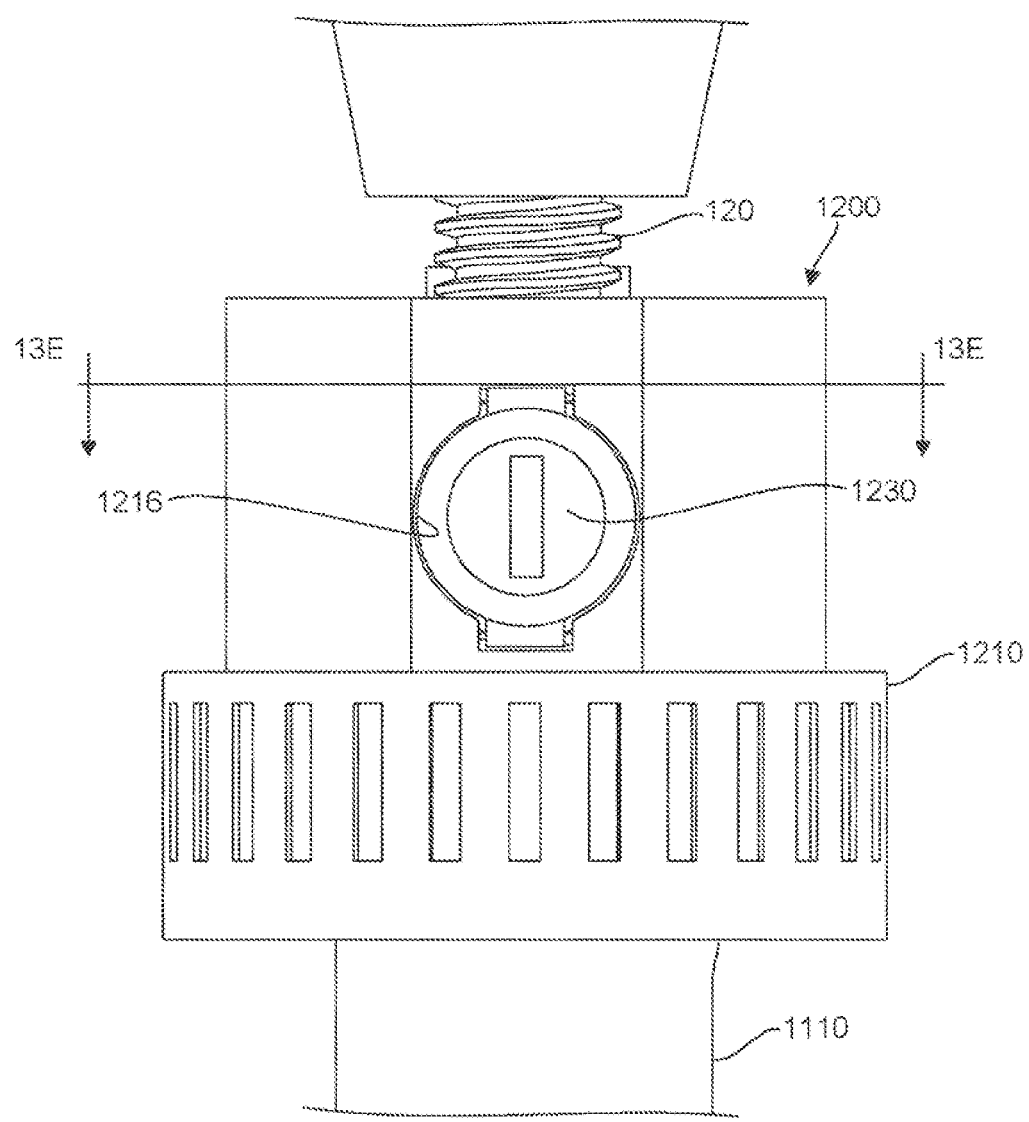
FIG. 13C illustrate an opposite side elevation view of the acute adjustment mechanism shown in FIG. 13B with a button pushed.
Figure 13D:
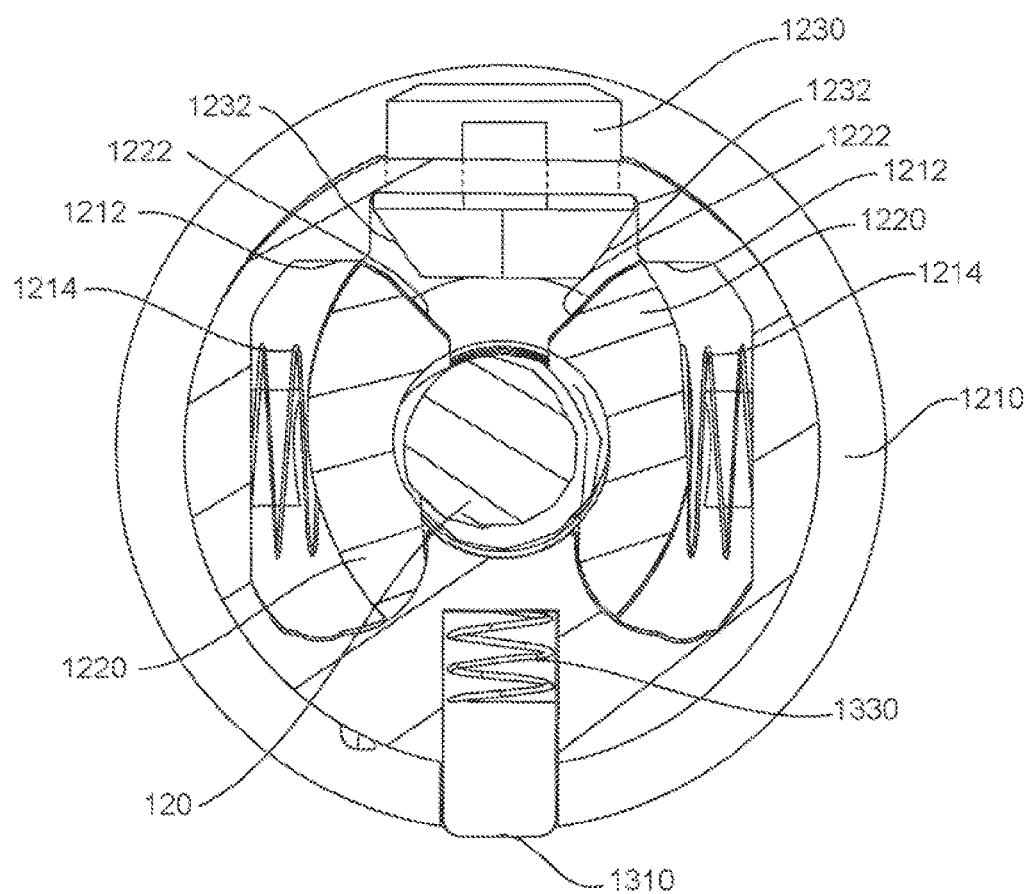
FIG. 13D is a cross-sectional view of the acute adjustment mechanism shown in FIG. 13B.
Figure 13E:
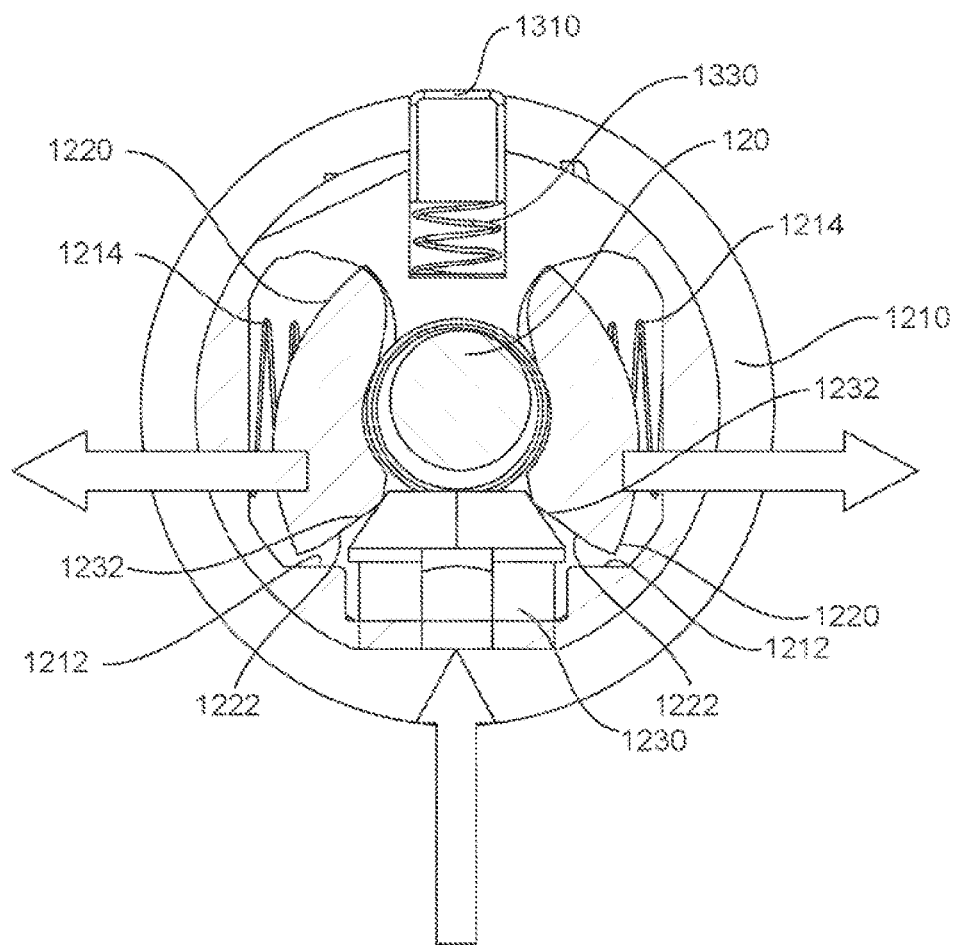
FIG. 13E is a cross-sectional view of the acute adjustment mechanism shown in FIG. 13C.
Figure 15A:
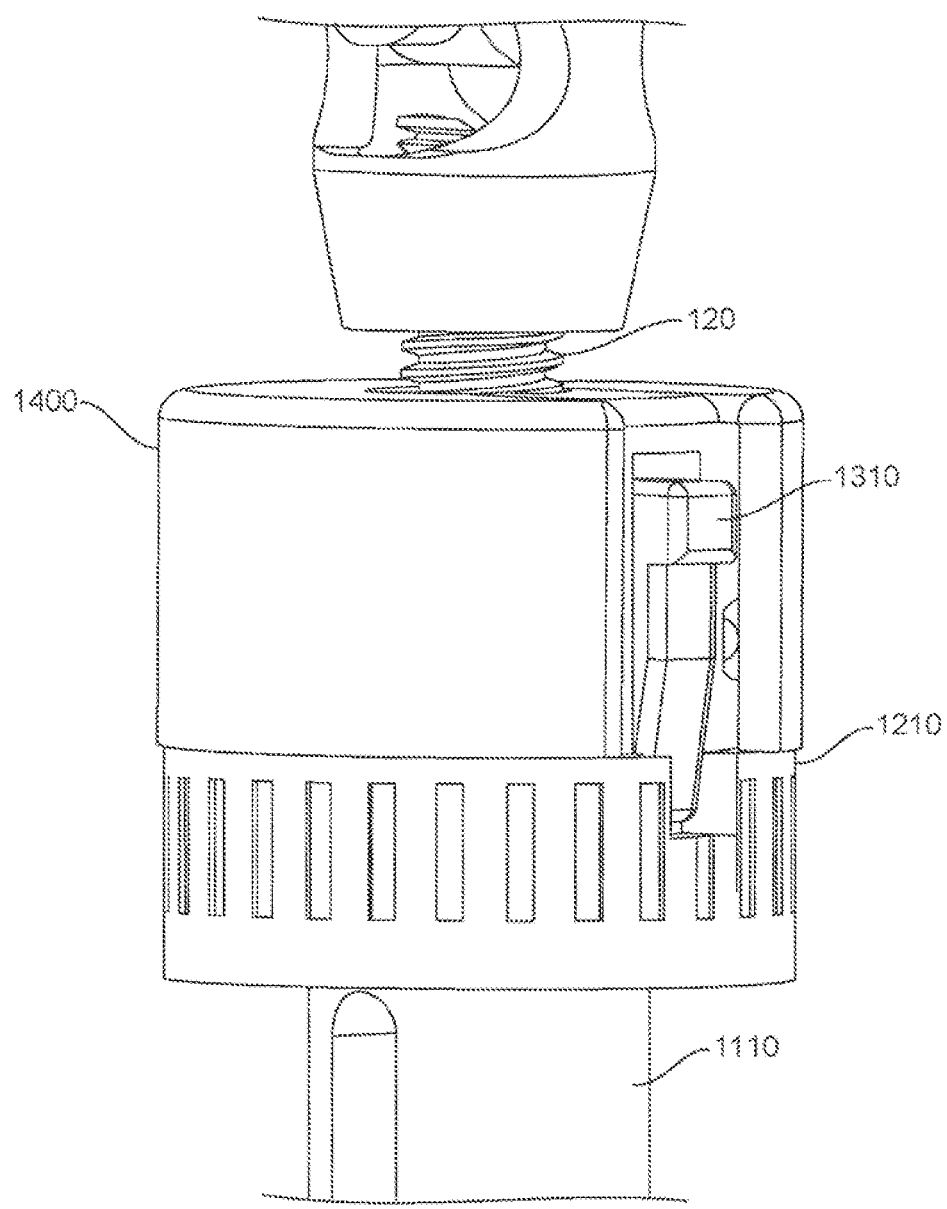
FIG. 15A is a perspective view of the acute adjustment mechanism shown in FIG. 14A showing a portion of an example of an embodiment of a precise adjustment mechanism.
Figure 15B:
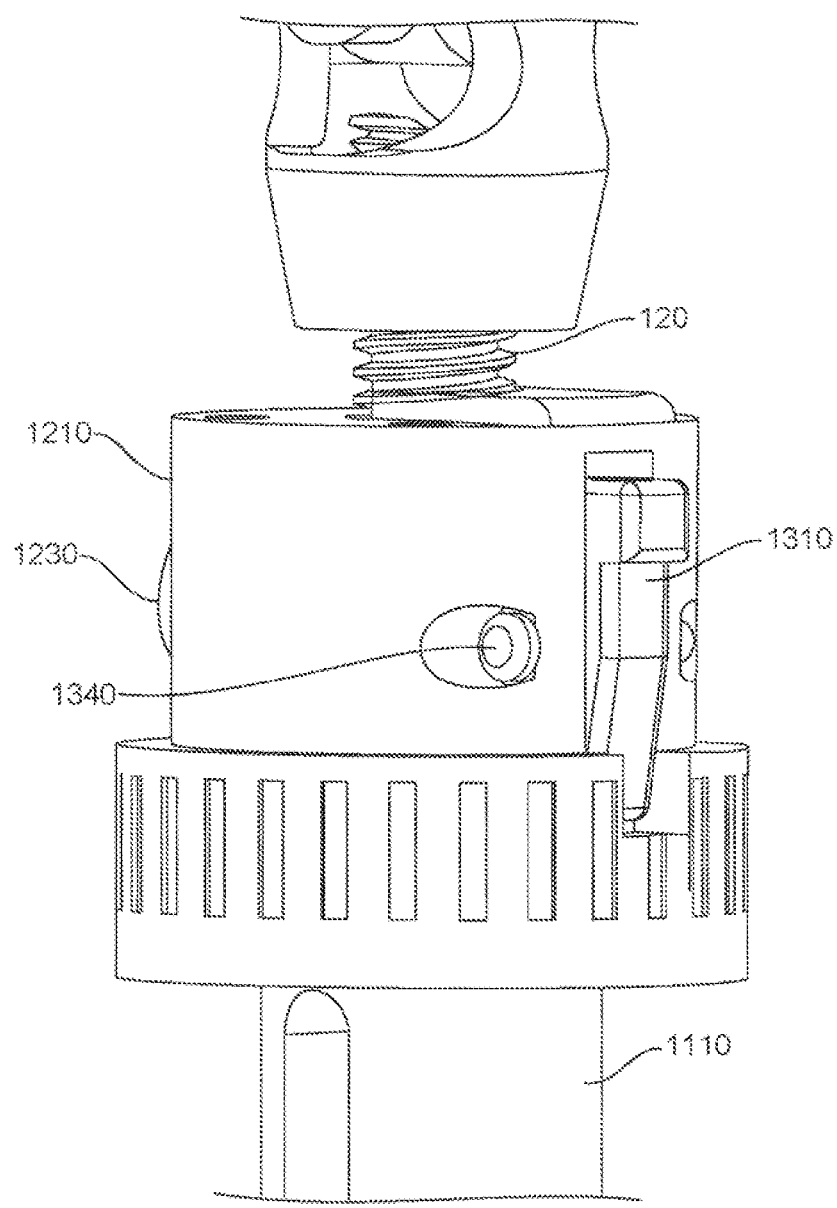
FIG. 15B is a perspective view of the acute adjustment mechanism shown in FIG. 15A with the band removed.
Figure 15C:
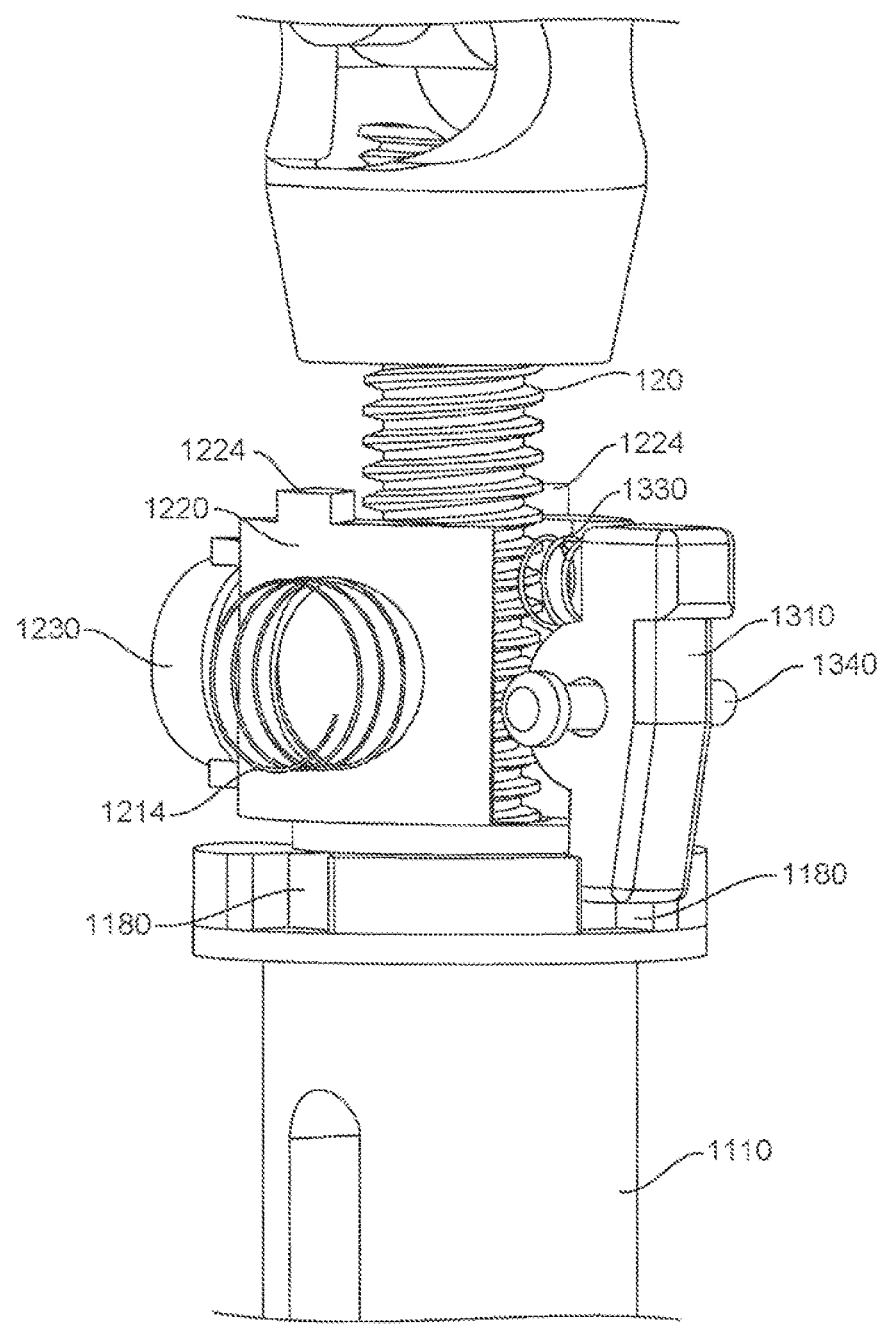
FIG. 15C is a perspective view of the acute adjustment mechanism shown in FIG. 15B with the actuator body of the device removed to view internal components of the mechanism.
Figure 15D:
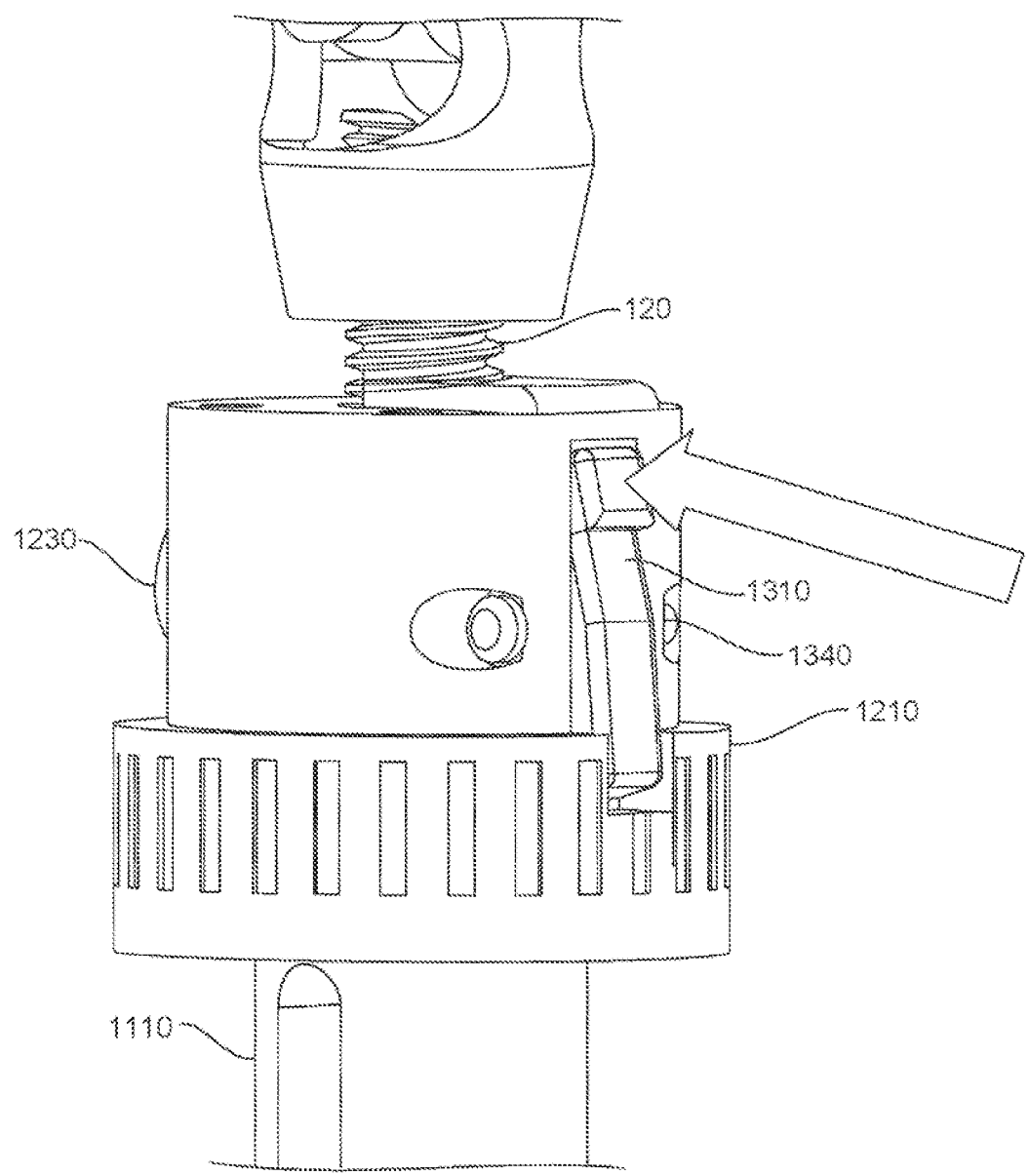
FIG. 15D is a perspective view of the acute adjustment mechanism shown in FIG. 15B with the precise adjustment mechanism in an unlocked position.
Figure 15E:
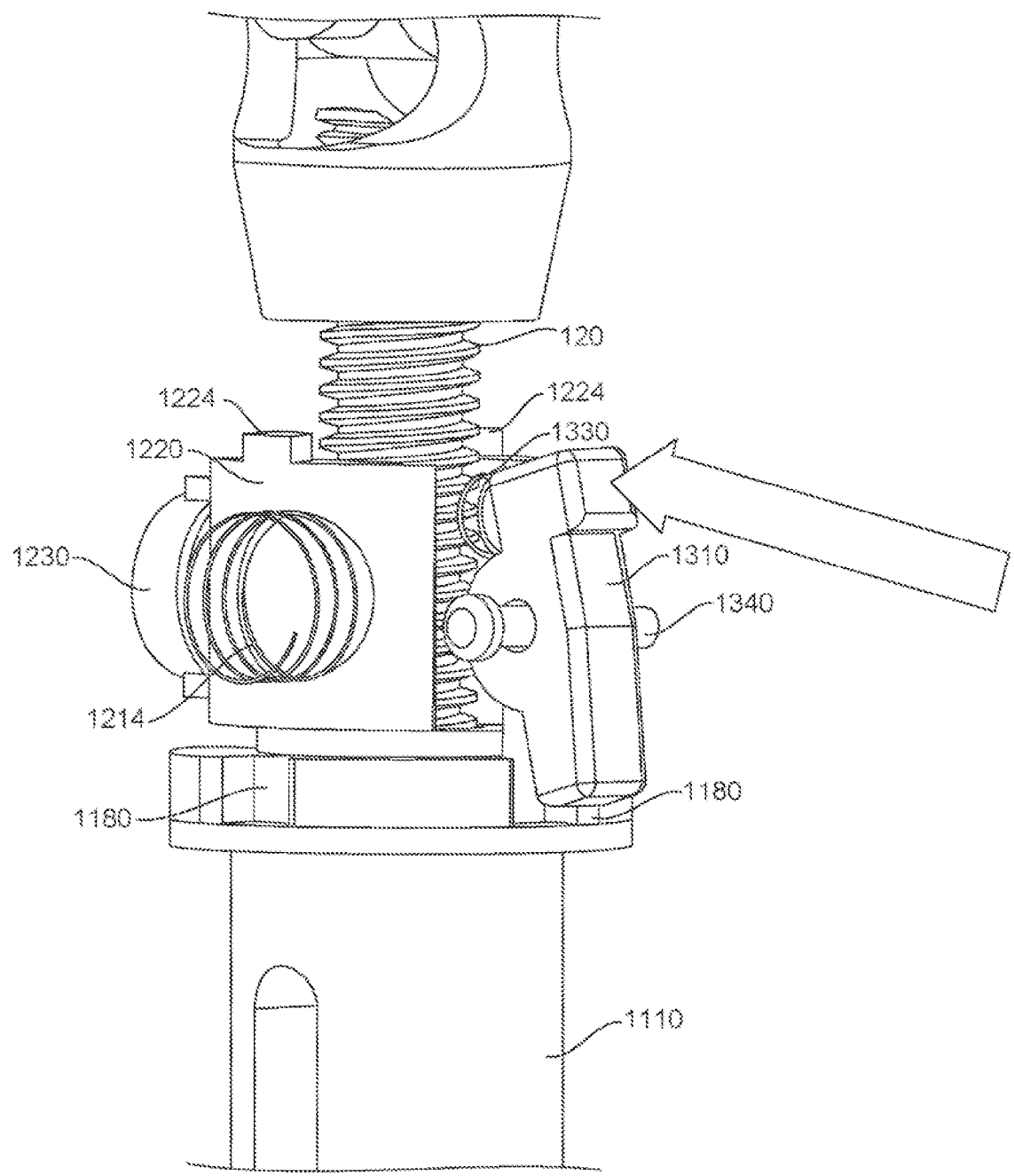
FIG. 15E is a perspective view of the acute adjustment mechanism shown in FIG. 15D with the actuator body of the device removed to view internal components of the mechanism.

Referring to FIGS. 12, 13A, and 15A, as previously mentioned, the external fixation strut 1100 may also include a band 1400. In some embodiments, bands 1400 may be arranged and configured as identification (ID) bands for identifying each particular strut in the external fixation system. As such, the bands 1400 may be provided to numerically identify strut assemblies so that each strut assembly may be distinguished for a prescription. In use, the bands 1400 are coupled to the external fixation struts 1100. For example as shown, in one example of an embodiment, the bands 1400 may be slid down over the top of the actuator body 1210. Some embodiments of the band 1400 include pegs, projections, or other connection devices that are sized and configured to be received by holes in an associated actuator body to couple the components. The band 1400 provides a safety feature and reduces the risk of inadvertent acute adjustment of the strut assembly by limiting access to the disengagement member 1230, making it more difficult to inadvertently depress. Acute adjustment generally takes place clinically during application of the external fixation frame or during strut change-outs. The bands 1400 may be helpful to avoid inadvertent acute adjustment when a patient is adjusting struts using precise adjustment mechanisms to comply with an adjustment prescription such as, for example, when adjusting the struts at home utilizing the precise adjustment mechanism to comply with the prescription.

Referring to FIGS. 15A-15E, the precise adjustment mechanism 1300 will be described in greater detail. As will be described in greater detail, the precise adjustment mechanism 1300 enables the strut length of the external fixation struts 1100 to be adjusted. As noted above, the spring 1330 biases the body 1310 about the pivot pin 1340 to an engaged position toward the notch 1180 (FIGS. 15C and 15E) in the strut body 1110. Thus arranged, the body 1310 cannot turn relative to the strut body 1110 as long as a portion of the body 1310 is seated in the notch 1180. Moving the body 1310 about the pivot pin 1340 in the direction of the action arrows in FIGS. 15D and 15E from a first position to a second position so that the body 1310 is no longer positioned in the notice 1180 allows for the precise adjustment mechanism 1300 to be turned with the acute adjustment mechanism 1200, advancing or retrieving the threaded rod 120 (e.g., the acute and precise adjustment mechanisms 1200, 1300 are fixed within the actuator body 1210. As such, when the actuator body turns to adjust small increments (e.g., via the precise adjustment mechanism) the components of both mechanisms turn in unison). The number and spacing of the notches 1180 defines the resolution of precise adjustment. For example, four equally spaced notches 1180 with an assembly that advances one millimeter per full turn provides tactile feel and hard stops every quarter of a turn of adjustment, which are one-quarter millimeter linear adjustment increments. When fully assembled, the threaded collar 1250 (FIG. 14B) turns with the actuator body 1210 as one assembly. In other embodiments, the body 1310, or a similar component, may be coupled to the strut body and notches, openings, or other mechanisms may be located on the actuator body.

Although not shown, the external fixation strut 1100 may also include a locking sleeve such as, for example, the locking sleeve 600 described above in association with FIG. 10. In use, incorporation of the locking sleeve 600 may assist with preventing accidental adjustment. In this embodiment, and as previously mentioned, adjustment would be limited to motion of the tracer pin 610 with the locking sleeve 600 coupled around the strut body 1110. The locking sleeve 600 may be held in place at the desired level with the bolt 620 that may be engage with the side of the strut body 1110. This prevents the strut from adjusting but does not take up any adjustment range of the threaded rod 120.

The external fixation strut 1100 may be a part of an external fixation system that includes an upper base, a lower base, and multiple struts between the upper base and the lower base. At least one of the struts may be the external fixation strut 1100 or one of the other fixation struts disclosed herein. In some embodiments, the system includes six struts coupled between the upper base and the lower base and at least one of the six struts is the external fixation strut 1100, but in other embodiments may include systems with fewer or more struts than six. Any of the struts described herein may also include one or more telescoping bodies that translate relative to one another to change the overall length of the strut. The system may also include connectors for coupling with one or both of the upper base and the lower base. For example, the connectors may include the universal joints 500 and further may include fasteners between the universal joints 500 and the bases. System embodiments may also include bone fixation mechanisms for coupling between the connectors or the bases and tissue of a patient. Such bone fixation mechanisms may include wires (threaded and unthreaded), k-wires, pins, and screws, for example.

Figure 17:
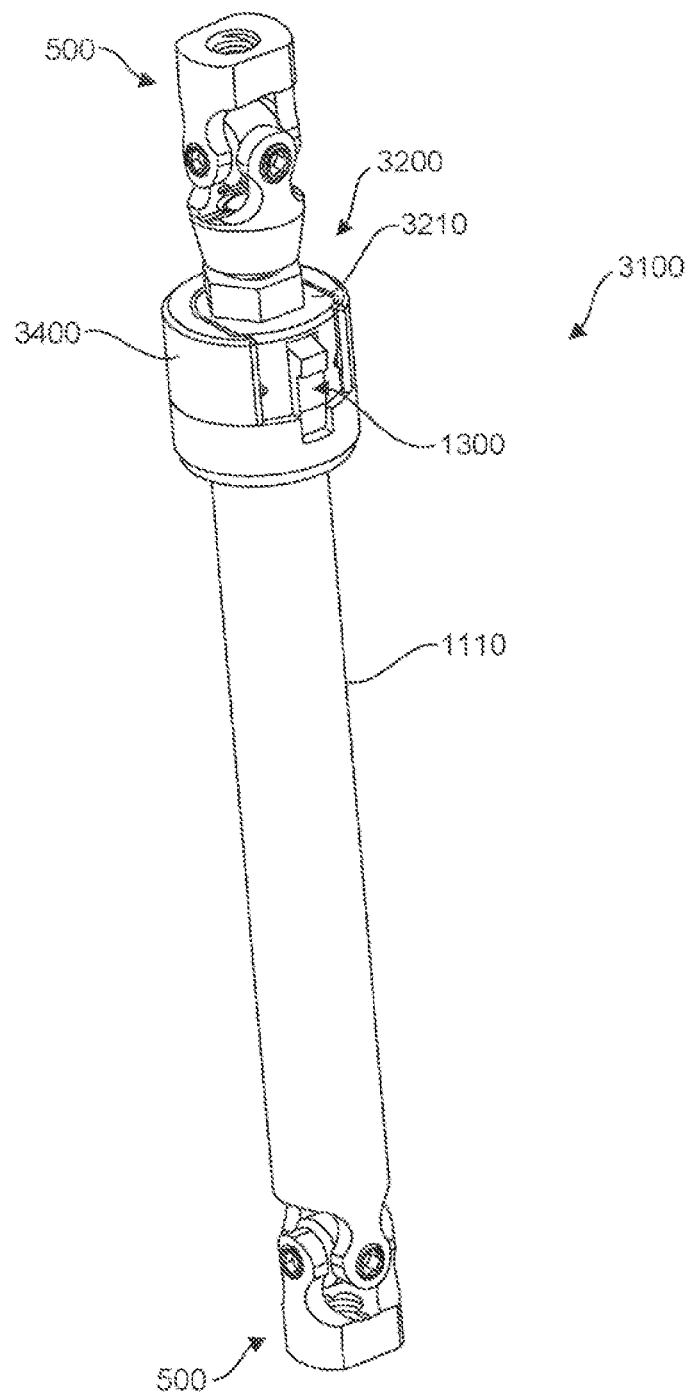
FIG. 17 is a perspective view of an alternate example of an embodiment of an external fixation strut in accordance with principles of the present disclosure.
Figure 18A:
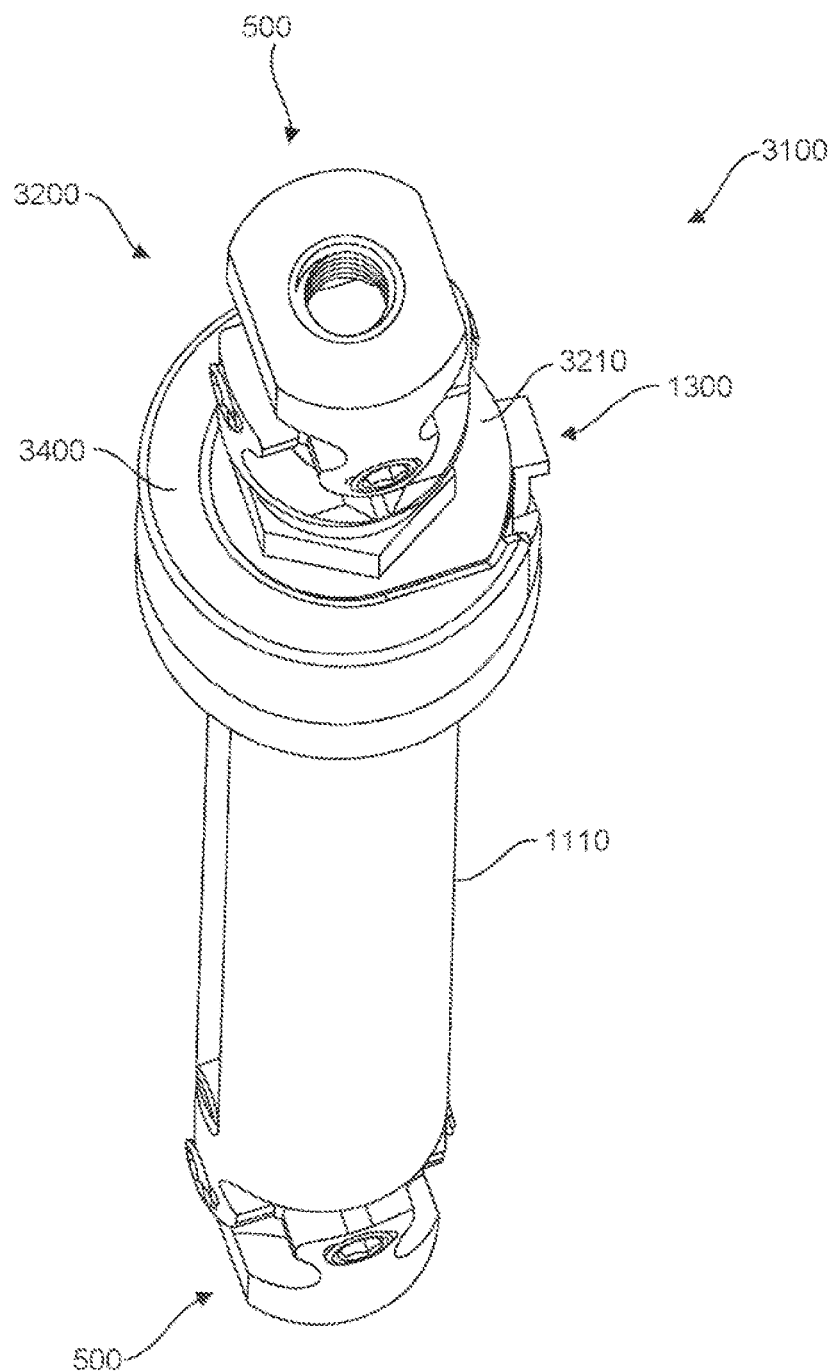
FIG. 18A is a top, perspective view of the external fixation strut shown in FIG. 17, the view illustrating an example of an embodiment of an acute adjustment mechanism and band.
Figure 18B:
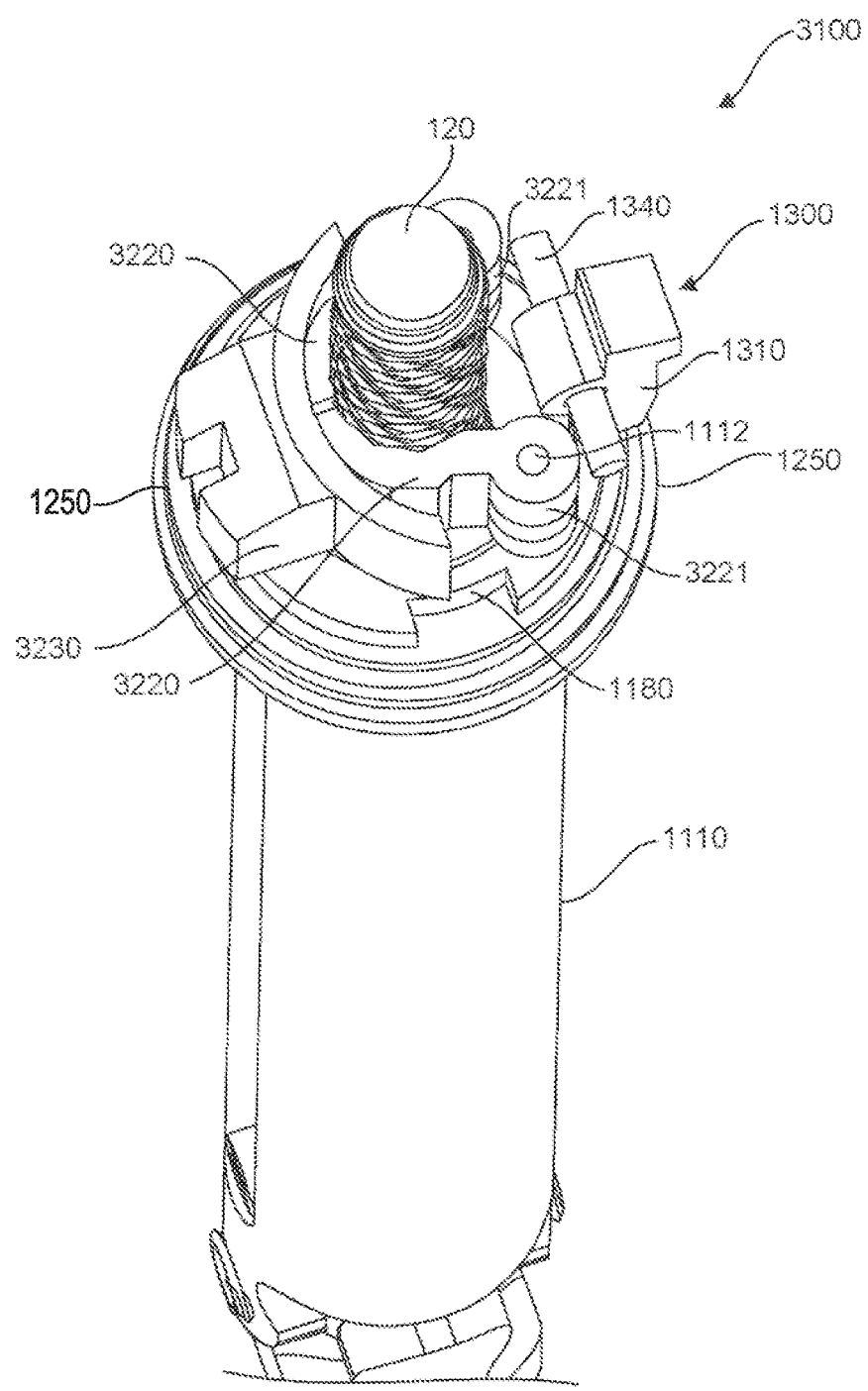
FIG. 18B is a perspective view of the acute adjustment mechanism shown in FIG. 18A with the actuator body of the device removed to view internal components of the mechanism.
Figure 18C:
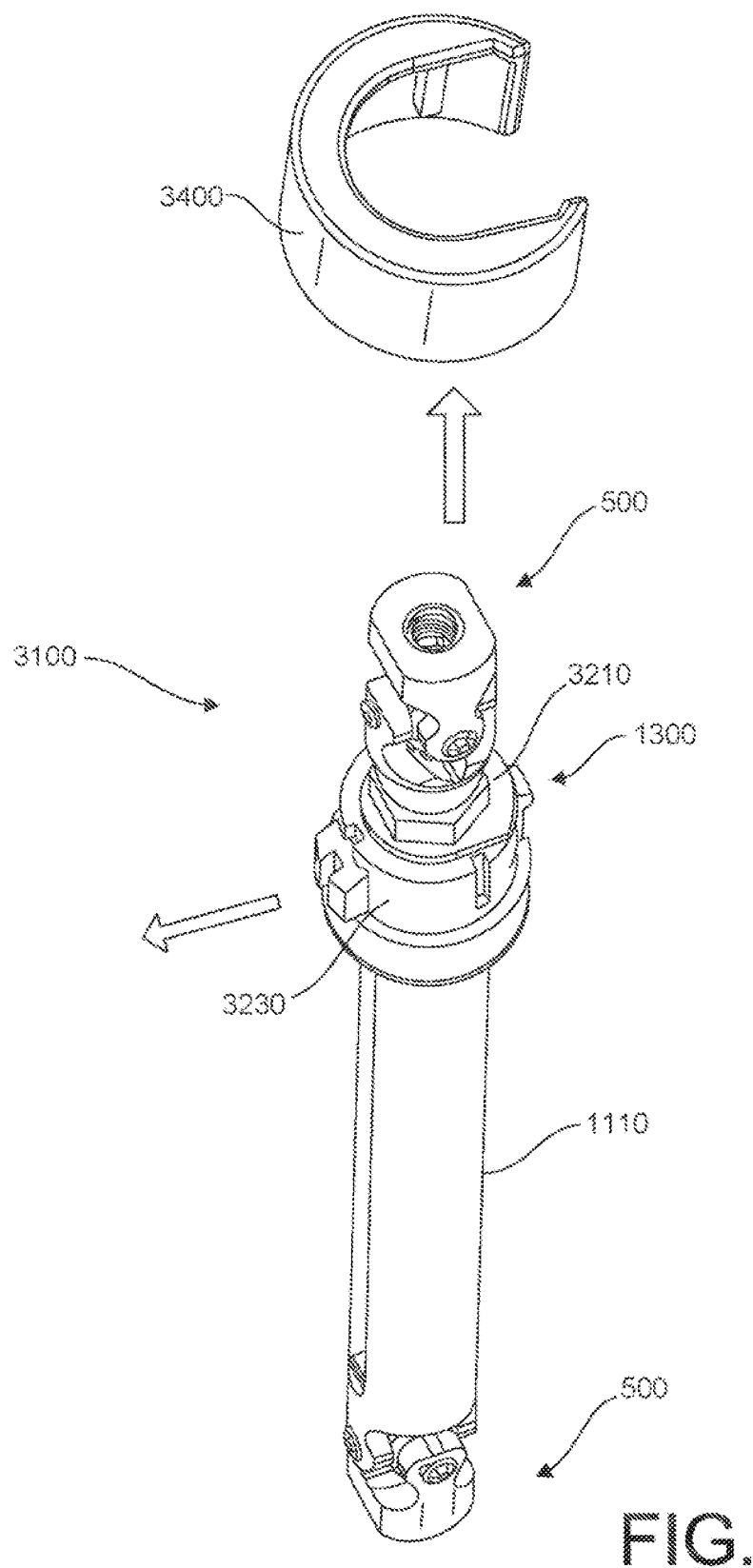
FIG. 18C is a perspective view of the acute adjustment mechanism shown in FIG. 18A with the band removed.
Figure 18D:
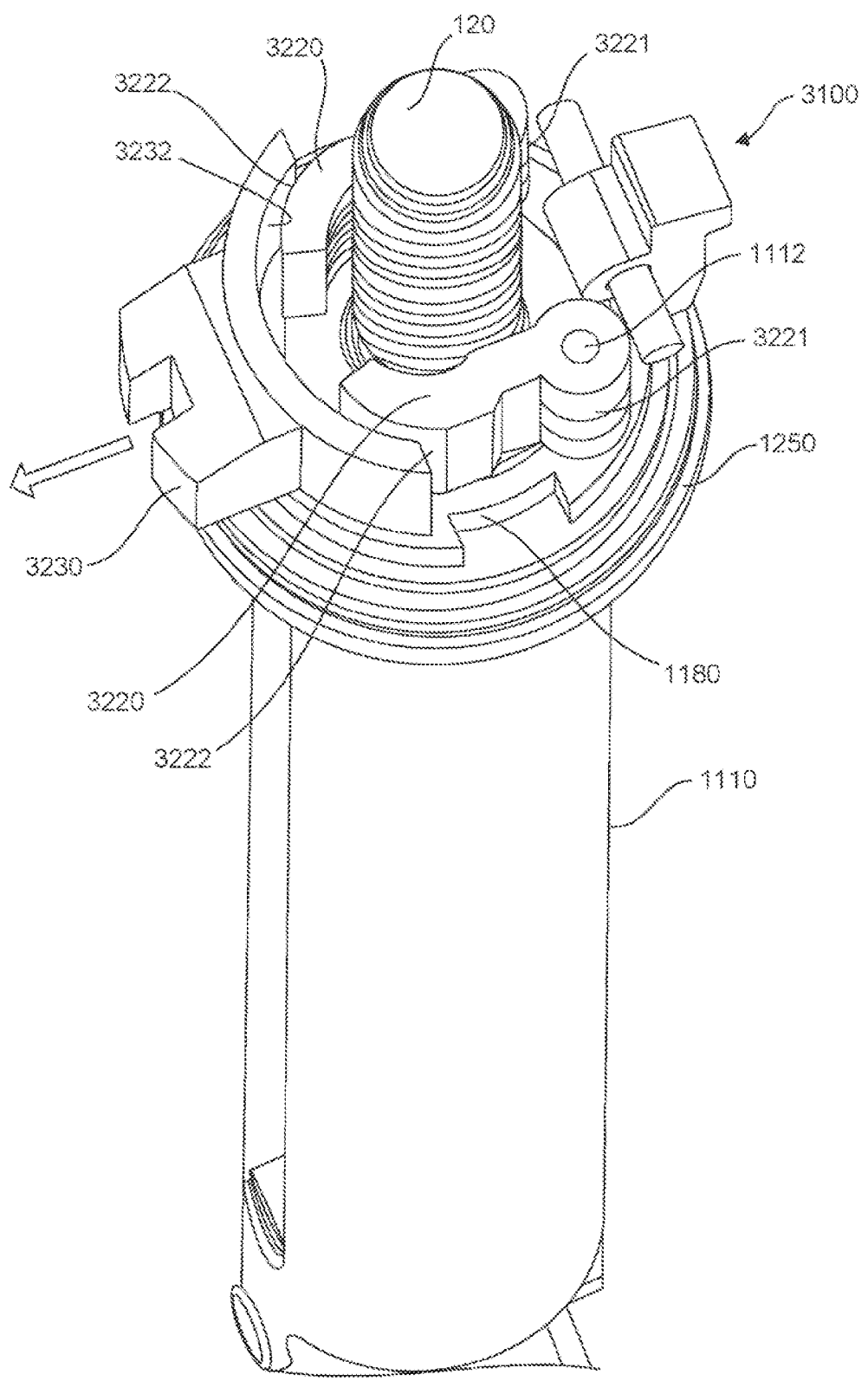
FIG. 18D is a perspective view of the acute adjustment mechanism shown in FIG. 18C with a portion of the device removed to view internal components of the mechanism.

Referring to FIGS. 17-18D, an alternate example of an embodiment of an external fixation strut 3100 is disclosed. As will be described herein, external fixation strut 3100 may be substantially similar to external fixation struts 100, 1100 except as noted herein. As shown, the external fixation strut 3100 includes a strut body 1110, a threaded rod 120 substantially rotationally fixed relative to the strut body 1110 so that movement of the threaded rod 120 axially translates or moves the threaded rod 120 relative to the strut body 1110, an acute adjustment mechanism 3200 selectively disengageable from threads of the threaded rod 120, and a precise adjustment mechanism such as, for example, the precise adjustment mechanism 1300.

In one example of an embodiment, the acute adjustment mechanism 3200 includes an actuator body 3210 that includes the threaded collar 1250 (FIGS. 18B and 18D), a spring-loaded mobile jaw 3220, and one or more disengagement members 3230 that are configured to interact with the mobile jaw 3220. The disengagement member 3230 includes structure arranged and configured to interact with the mobile jaws 3220. For example, the disengagement members 3230 may include a structure with an arcuate surface 3232 (FIG. 18D) facing the mobile jaws 3220 configured to move away from and toward the center of the device, but other embodiments are envisioned including, for example, a disengagement member including one or more wedges, screws, cams, or any other mechanism now known or hereafter developed.

In the illustrated embodiment, the external fixation strut 3100 may include a threaded collar such as, for example, the threaded collar 1250, to connect the actuator body 3210 to the strut body 1110. In one example of an embodiment, the actuator body 3210 may include one or more channels to guide the path of the mobile jaws 3220. In the embodiment depicted, each of the mobile jaws 3220 is hinged about a pin 1112 (FIGS. 18B and 18D). The illustrated mobile jaws 3220 include torsion springs 3221 (FIGS. 18B and 18D) that bias the mobile jaws 3220 away from the threaded rod 120 and toward the disengagement member 3230. The mobile jaws 3220 have faces 3222 (FIG. 18D) that interact with the arcuate surface 3232 of the disengagement member 3230 so that when the disengagement member 3230 is allowed to move away from the center of the device (e.g., when the disengagement member is allowed to move the first position to the second position), the faces 3222 of the mobile jaws press against the arcuate surface 3232 and the mobile jaws 3220 move (e.g., separate and disengage) from the threaded rod 120 (FIGS. 18C and 18D) so that the strut length of the external fixation strut 3100 can be adjusted acutely.

In one example of an embodiment, the precise adjustment mechanism may be the precise adjustment mechanism 1300 previously described. As previously described, the precise adjustment mechanism 1300 includes a body 1310, a pivot pin 1340, and a spring. The spring biases the body 1310 about the pivot pin 1340 to an engaged position toward a notch 1180 (FIGS. 18B and 18D) in the strut body 1110. The body 1310 cannot turn relative to the strut body 1110 as long as a portion of the body 1310 is seated in the notch 1180.

In one example of an embodiment, the external fixation strut 3100 may also include bands 3400 (FIGS. 17, 18A, and 18C) as described herein. In addition, and/or alternatively the external fixation strut 3100 may include and one or more connectors 500 to couple the external fixation strut 3100 to one or more bases. As shown, and as previously mentioned, the connectors 500 may be in the form of a U-joint, alternatively however any other now known or hereafter developed connector can be used such as, for example, ball joints, threaded ends, etc. In some embodiments, the band 3400 may be considered a containment device that is a component of the disengagement member that works in conjunction with the disengagement member 3230 to hold the disengagement member 3230 toward the center of the device to cause the mobile jaws 3220 to engage with the threaded rod 120 (e.g., the band/containment device are arranged and configured to hold the disengagement member in the first position so that the mobile jaws engage the threaded rod).

In use, the mobile jaws 3220 of this embodiment are both biased to decouple from the threads of the threaded rod 120 by the torsion springs 3221. The mobile jaws 3220 shown include threaded portions that interact with the threaded rod 120, but in other embodiments, mobile jaws may include other structure for interacting with the threaded rod including, for example, knurling, a softer material, or any other structure or material that is capable of interacting with the threads of the threaded rod 120. In use, the mobile jaws 3220 are arranged and configured to interact with the disengagement member 3230. For example, the mobile jaws 3220 may include faces 3222 that interact with the arcuate surface 3232 of the disengagement member 3230. In use, the disengagement member 3230 is designed so that it can be pressed toward the center of the device and toward the threaded rod 120 when the band 3400 is removed. The band 3400 may then be returned to position on the device, as shown in FIGS. 17 and 18A to keep the mobile jaws 3220 engaged with the threaded rod 120 (e.g., to hold the disengagement member in the first position so that the mobile jaws engage the threaded rod).

As shown in the progression between FIGS. 18A and 18C and with the action arrows in FIG. 18C, the mobile jaws 3220 are configured to pivot away from the threaded rod 120 when the band 3400 is removed from the device and the disengagement member 3230 is allowed to move away from the center of the device (e.g., the mobile jaws 3220 are arranged and configured to move from a first position to a second position wherein the mobile jaws move away (e.g., disengage) from the threaded rod 120 when the band 3400 is removed from the device and the disengagement member 3230 is allowed to move). Once the threads are disengaged, the strut length can be adjusted acutely. As shown in the progression between FIGS. 18A-18B and FIGS. 18C-18D, the disengagement member 3230 is biased to a disengaged state in the absence of the band 3400. By removing multiple bands 3400 on multiple external fixation struts, multiple external fixation struts can be adjusted acutely at once on an external fixation system.

Band 3400 placement is depicted in FIGS. 17 and 18A. In some embodiments, bands 3400 may be arranged and configured as identification (ID) bands for identifying each particular strut in the external fixation system. As such, the bands 3400 may be provided to numerically identify strut assemblies so that each strut assembly may be distinguished for a prescription. The bands 3400 shown slide down over the top of the actuator body 3210. In use, the bands 3400 are coupled to the external fixation struts 3100. For example, as shown, in one example of an embodiment, the band 3400 include pegs, projections, or other connection devices that fit in holes in an associated actuator body to couple the components. The band 3400 provides a safety feature and reduces the risk of inadvertent acute adjustment of the strut assembly by limiting movement of the disengagement member 3230. As previously mentioned, acute adjustment generally takes place clinically during application of the external fixation frame or during strut change-outs. The bands 3400 may be helpful to avoid inadvertent acute adjustment when a patient is adjusting struts using precise adjustment mechanisms to comply with an adjustment prescription.

Although not shown, the external fixation strut 3100 may also include a locking sleeve such as, for example, the locking sleeve 600 described above in association with FIG. 10. Use of such a device is an option for preventing accidental adjustment.

The external fixation strut 3100 may be a part of an external fixation system that includes an upper base, a lower base, and multiple struts between the upper base and the lower base. At least one of the struts may be the external fixation strut 3100 or one of the other fixation struts disclosed herein. In some embodiments, the system includes six struts coupled between the upper base and the lower base and at least one of the six struts is the external fixation strut 3100, but in other embodiments may include systems with fewer or more struts than six. Any of the struts described herein may also include one or more telescoping bodies that translate relative to one another to change the overall length of the strut. The system may also include connectors for coupling with one or both of the upper base and the lower base. For example, the connectors may include the universal joints 500 and further may include fasteners between the universal joints 500 and the bases. System embodiments may also include bone fixation mechanisms for coupling between the connectors or the bases and tissue of a patient. Such bone fixation mechanisms may include wires (threaded and unthreaded), k-wires, pins, and screws, for example.

Referring to FIGS. 19-21B, an alternate example of an embodiment of an external fixation strut 4100 is disclosed. As will be described herein, external fixation strut 4100 may be substantially similar to external fixation strut 100, 1100, 3100 except as noted herein. As shown, the external fixation strut 4100 includes a strut body 1110, a threaded rod 120 substantially rotationally fixed relative to the strut body 1110 so that movement of the threaded rod 120 axially translates or moves the threaded rod 120 relative to the strut body 1110, an acute adjustment mechanism 4200 selectively disengageable from threads of the threaded rod 120, and a precise adjustment mechanism such as, for example, the precise adjustment mechanism 1300.

In one example of an embodiment, the acute adjustment mechanism 4200 includes an actuator body 4210 that includes a threaded collar 1250 (FIGS. 20D, 20E, and 20G), a spring-loaded mobile jaw 4220, and one or more disengagement members 4230 that are configured to interact with the mobile jaw 4220. The disengagement member 4230 may be in the form of a button capable of translation toward the center of the device, but other embodiments are envisioned including, for example, one or more wedges, screws, cams, or any other mechanism now known or hereafter developed.

In use, the threaded collar 1250 is arranged and configured to couple the actuator body 4210 to the strut body 1110. In one example of an embodiment, the actuator body 4210 may include one or more channels to guide the path of the mobile jaws 4220. The device may include springs configured to bias the mobile jaws 4220 against the threaded rod 120 and toward the disengagement member 4230. As shown in FIGS. 20E and 20G, the mobile jaws 4220 may include faces 4222 that interact with surfaces 4232 of the disengagement member 4230 so that when the disengagement member 4230 is pressed inward, the mobile jaws 4220 move (e.g., are separate and disengage) from the threaded rod 120 so that the strut length of the external fixation strut 4100 can be adjusted acutely.

In one example of an embodiment, the precise adjustment mechanism may be the precise adjustment 1300 previously described. As previously described, the precise adjustment mechanism 1300 includes a body 1310, a pivot pin 1340, and a spring. The spring biases the body 1310 about the pivot pin 1340 to an engaged position toward a notch 1180 (FIGS. 20D, 20E, and 20G) in the strut body 1110. In use, the body 1310 is inhibited from moving (e.g., turning) relative to the strut body 1110 as long as a portion of the body 1310 is seated in the notch 1180.

In one example of an embodiment, the external fixation strut 4100 may also include bands 4400 as described herein. In addition, and/or alternatively, the external fixation strut 4100 may include one or more connector 500 to couple the external fixation strut 4100 to one or more bases. As shown, and as previously mentioned, the connectors 500 may be in the form of a U-joint, alternatively however any other now known or hereafter developed connector can be used such as, for example, ball joints, threaded ends, etc.

In use, in the illustrated embodiment, the mobile jaws 4220 are both biased to couple with the threads of the threaded rod 120 by the springs or other biasing mechanisms. For example, in one embodiment, the springs could be torsion springs that fit over either or both of the pins 1112, as shown in FIG. 18B, or any other effective biasing force member. The mobile jaws 4220 shown include threaded portions that interact with the threaded rod 120, but other embodiments are envisioned including, for example, knurling, a softer material, or any other structure or material that is capable of interacting with the threads of the threaded rod 120. In use, the mobile jaws 4220 are arranged and configured to interact with the disengagement member 4230. For example, the mobile jaws 4220 may include faces 4222 that interact with surfaces 4232 of the disengagement member 4230. Aperture 4216 (FIGS. 20B and 20F) formed in the side of the actuator body 4210 may constrain the disengagement member 4230. In use, the disengagement member 4230 is designed so that it can be pressed from outside of the actuator body 4210 toward the threaded rod 120 (action arrow in FIG. 20F) so that when the disengagement member 4230 is pressed inward (e.g., when the disengagement member 4230 is moved from a first position to a second position), the mobile jaws 4220 disengage from the threaded rod 120 enabling the strut length of the external fixation strut 4100 to be adjusted acutely. For example, in one embodiment, the geometry of the disengagement member 4230 inside of the actuator body 4210 may be shaped like a wedge, although other suitable configurations are envisioned. The faces of the wedge interact with the faces 4222 of the mobile jaws 4220 so that when the disengagement member 4230 is pressed inward, the mobile jaws 4220 move (e.g., separate and disengage) from the threaded rod 120 (FIGS. 20F and 20G) enabling the threads to disengage, and the strut length to be adjusted acutely. In the embodiment shown, the mobile jaws 4220 are configured to pivot away from the threaded rod 120 when sufficiently interacted with by the disengagement member 4230.

The mobile jaws 4220 may be constrained within the actuator body 4210 by channels so that pivoting toward and away from the threaded rod 120 is accomplished along a designated path. Control of the pivoting path may also or alternatively be directed by pivoting about respective pins 1112 (FIGS. 20D, 20E, and 20G). As shown in FIG. 21A, and as will be described in greater detail below, after the disengagement member 4230 has been pressed toward the threaded rod 120, the disengagement member 4230 may be held in this position by a temporary or acute band 4499 positionable on the external fixation struts. By installing multiple temporary or acute bands 4499 on multiple external fixation struts in this manner, multiple external fixation struts can be adjusted acutely at once because the user is not required to keep the disengagement members 4230 depressed by hand, as will be described in greater detail below.

Figure 19:
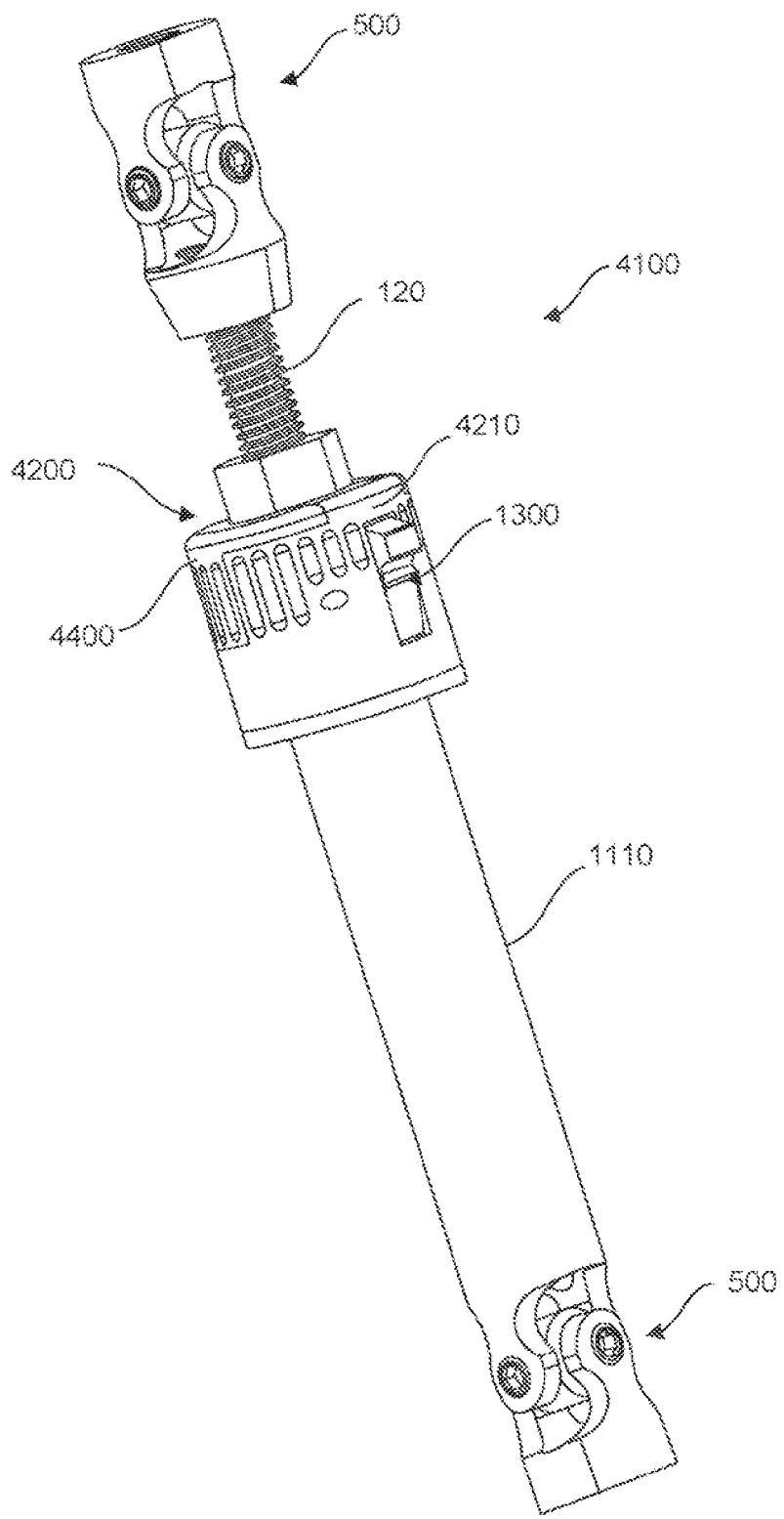
FIG. 19 is a perspective view of an alternate example of an embodiment of an external fixation strut in accordance with principles of the present disclosure.
Figure 20A:
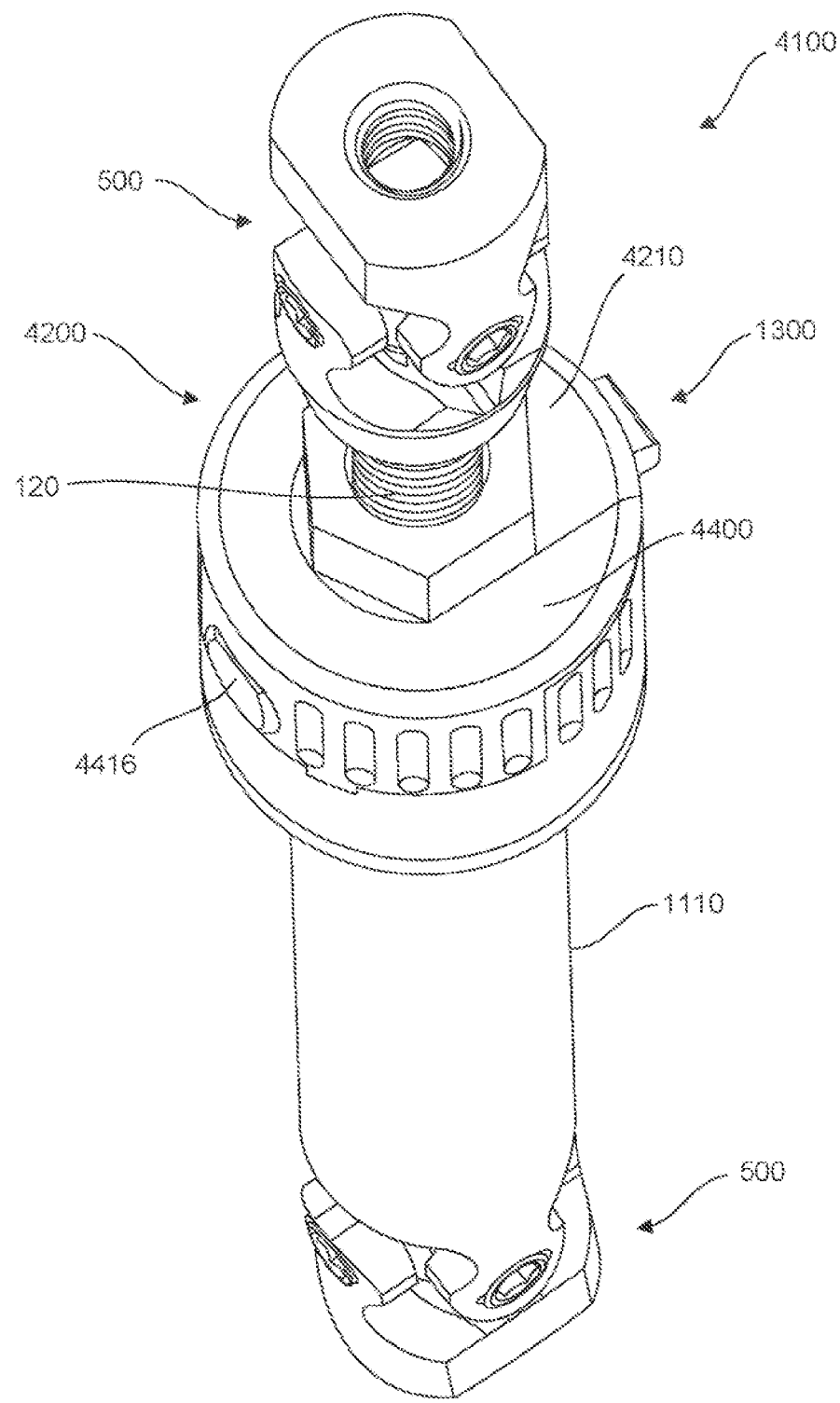
FIG. 20A is a top, perspective view of the external fixation strut shown in FIG. 19, the view illustrating an example of an embodiment of an acute adjustment mechanism and band.
Figure 20B:
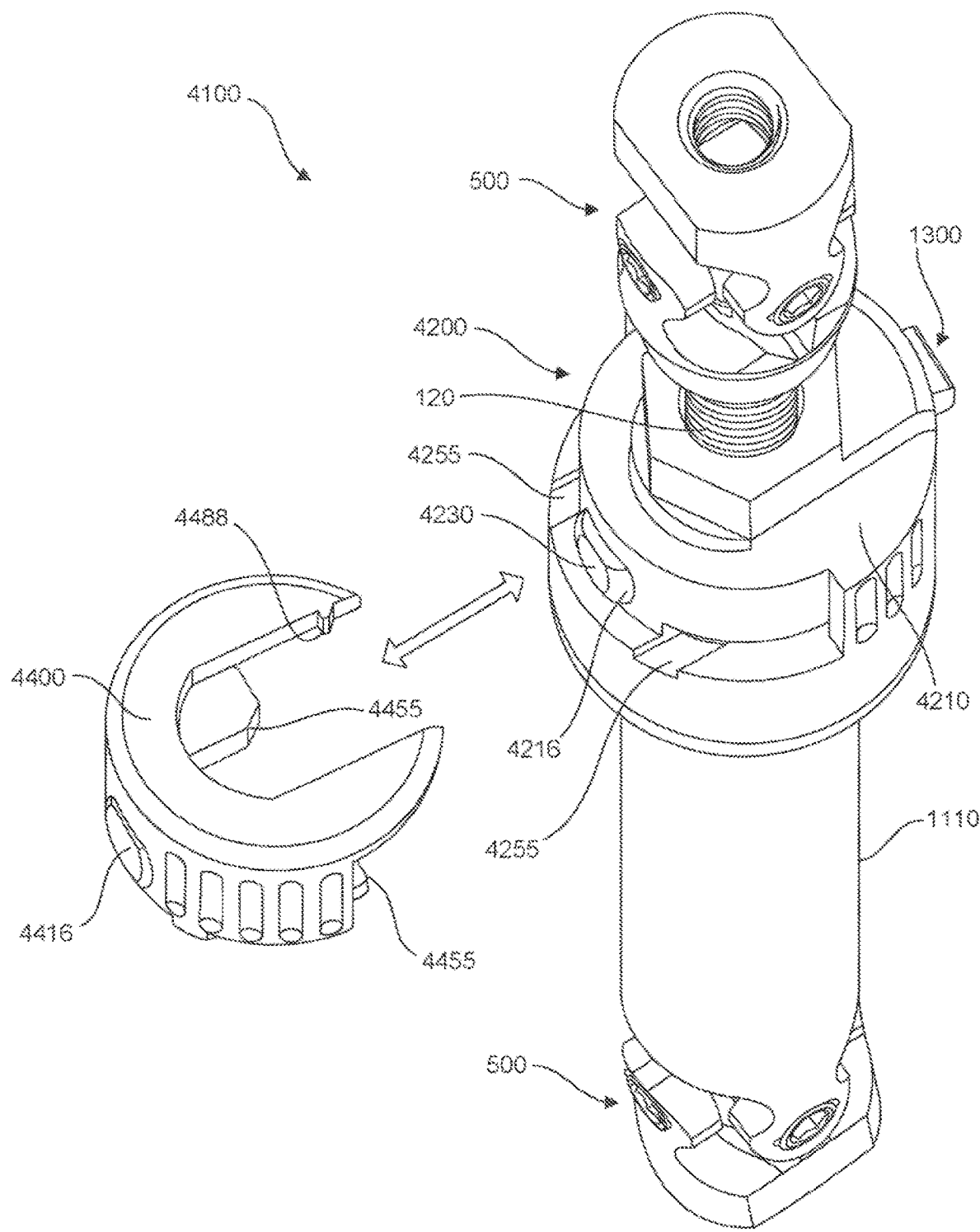
FIG. 20B is a perspective view of the acute adjustment mechanism shown in FIG. 20A with the band removed.
Figure 20C:
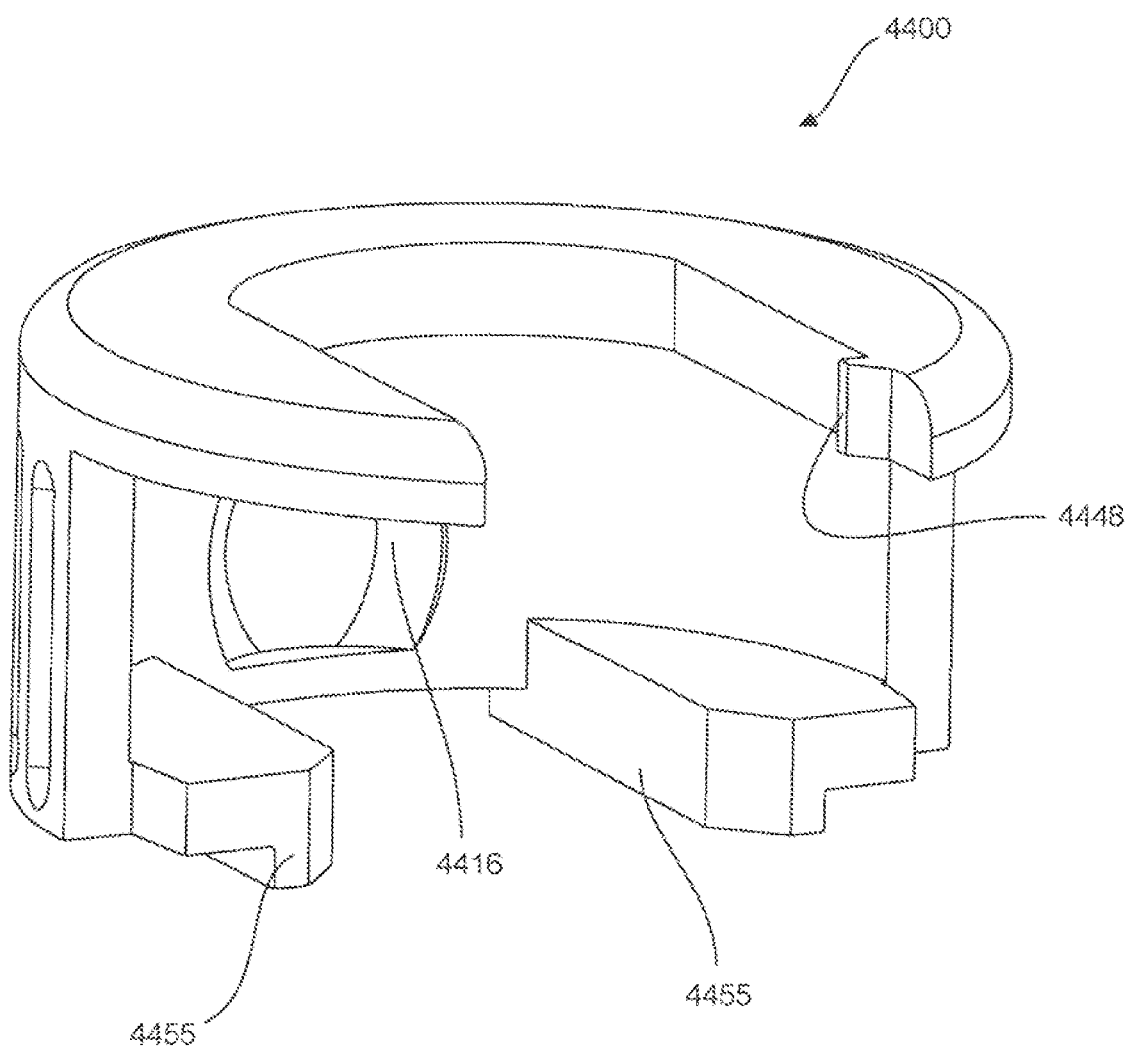
FIG. 20C is a perspective view of the band shown in FIGS. 20A and 20B.
Figure 20D:
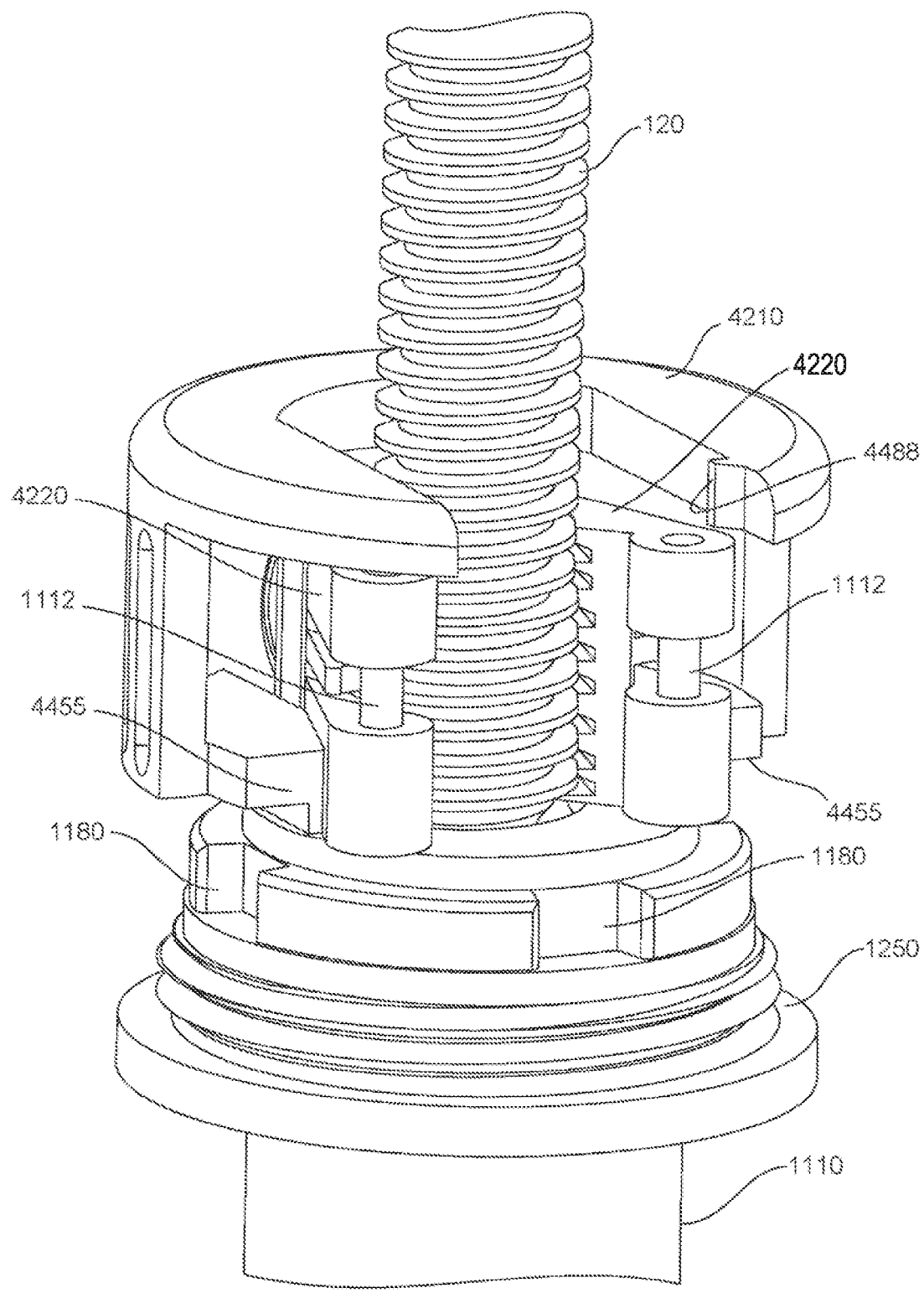
FIG. 20D is a perspective view of the acute adjustment mechanism shown in FIGS. 20A and 20B with the actuator body of the device removed to view internal components of the mechanism.
Figure 20E:
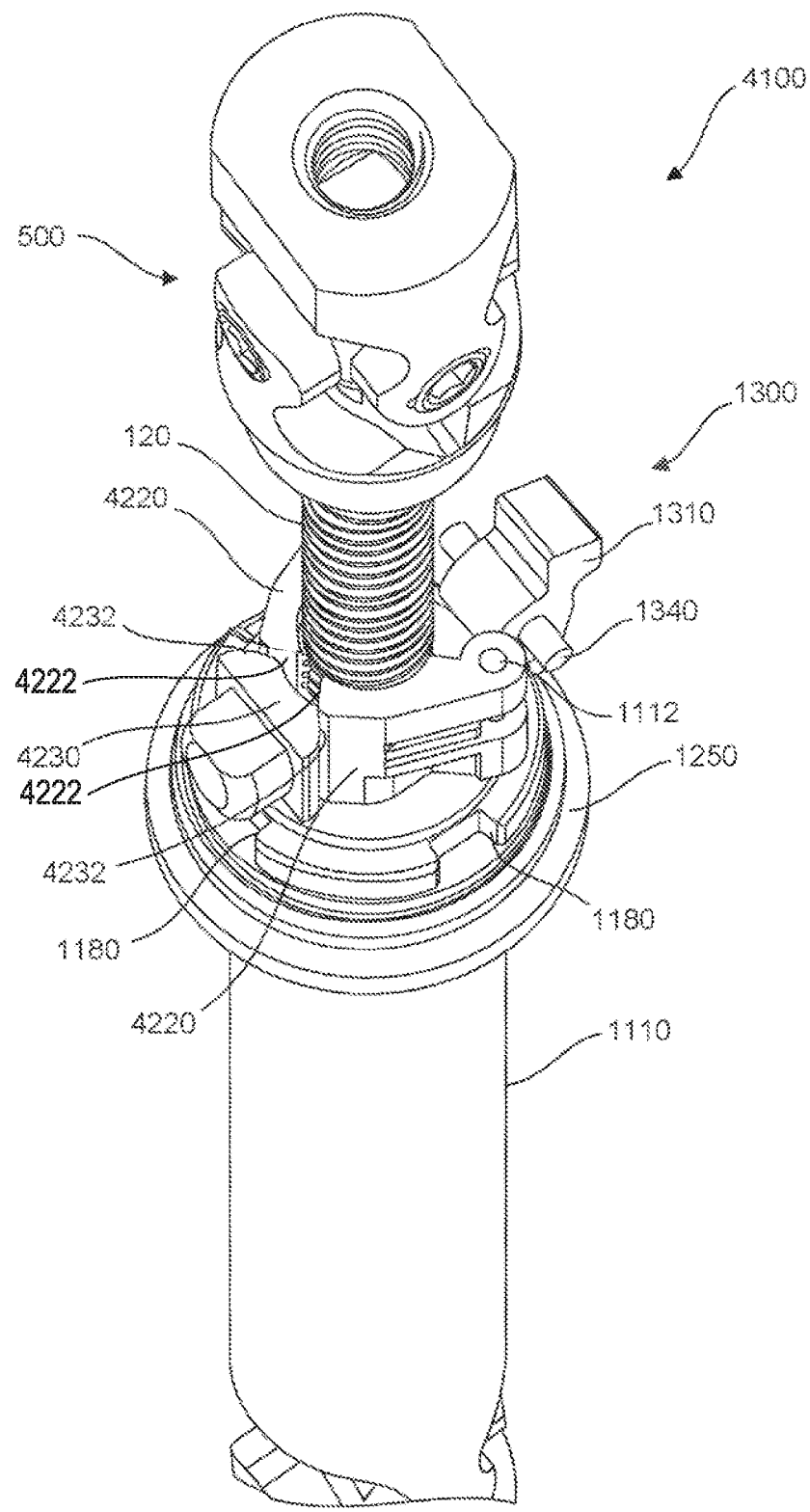
FIG. 20E is a perspective view of the acute adjustment mechanism shown in FIGS. 20A and 20B with a portion of the device removed to view internal components of the mechanism.
Figure 20F:
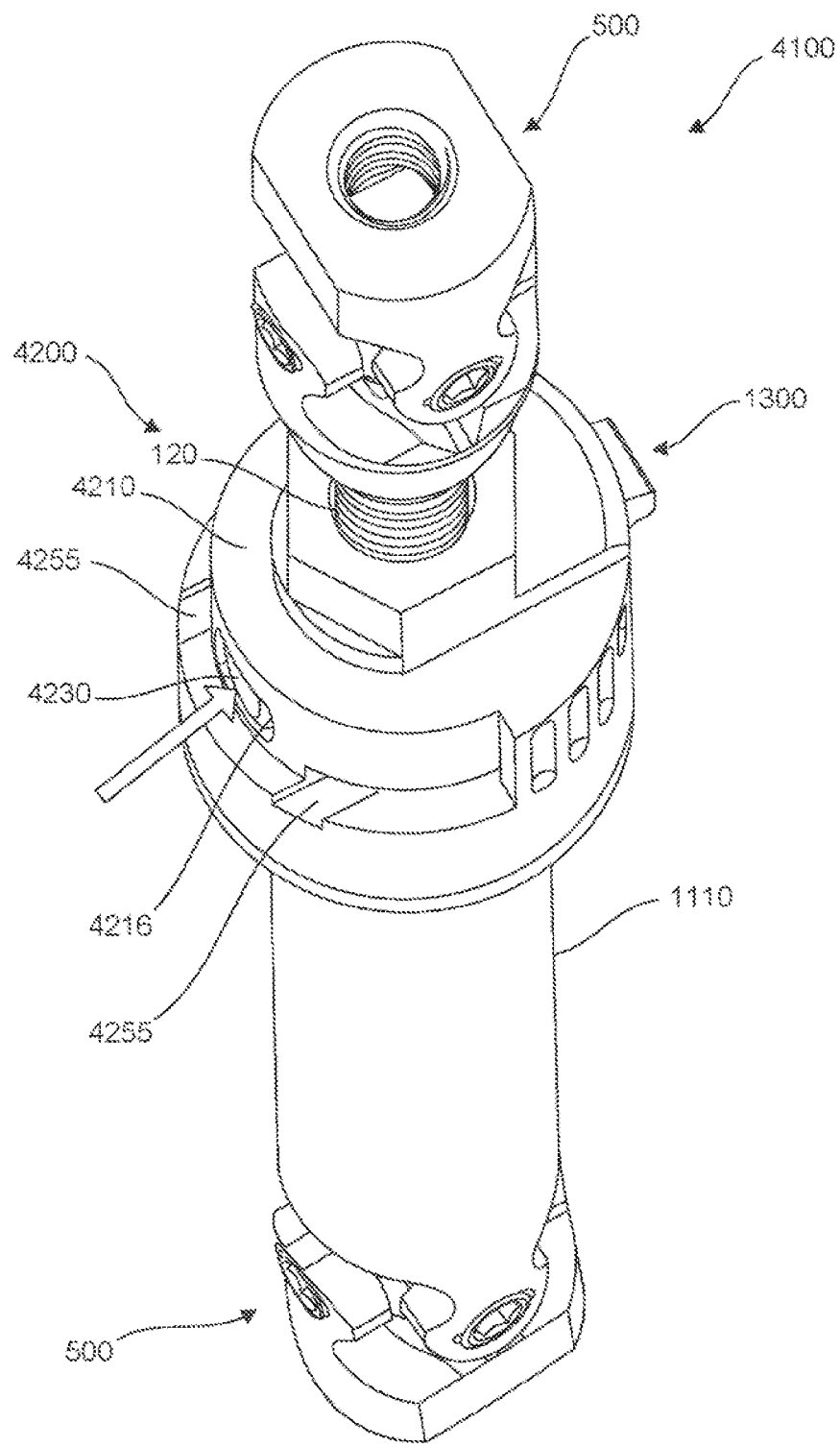
FIG. 20F is a top, perspective view of the external fixation strut shown in FIG. 19, the view illustrating the acute adjustment mechanism and showing the disengagement member in an activated position.
Figure 20G:
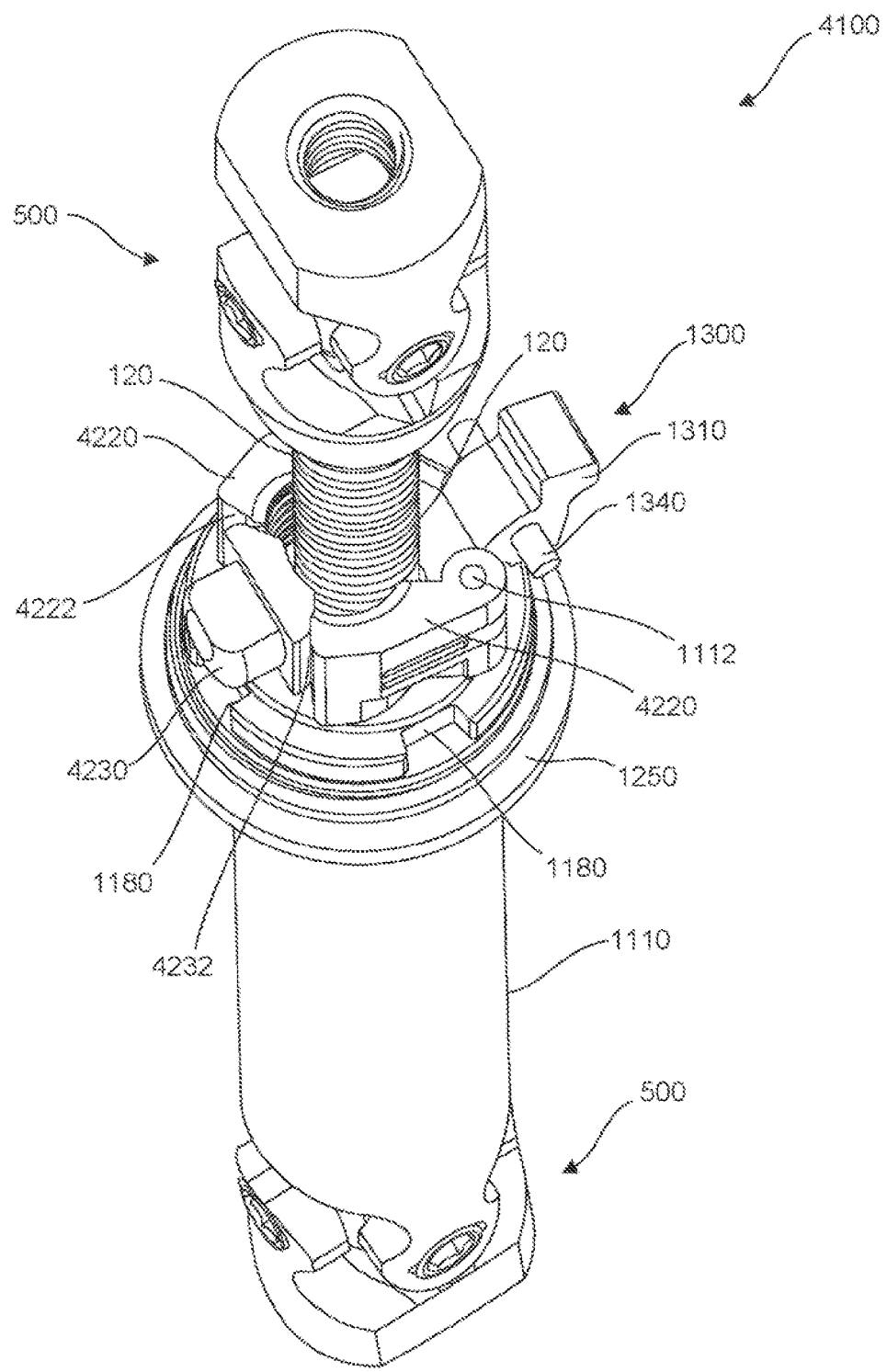
FIG. 20G is a perspective view of the acute adjustment mechanism shown in FIG. 20F with the actuator body of the device removed to view internal components of the mechanism.
Figure 21A:
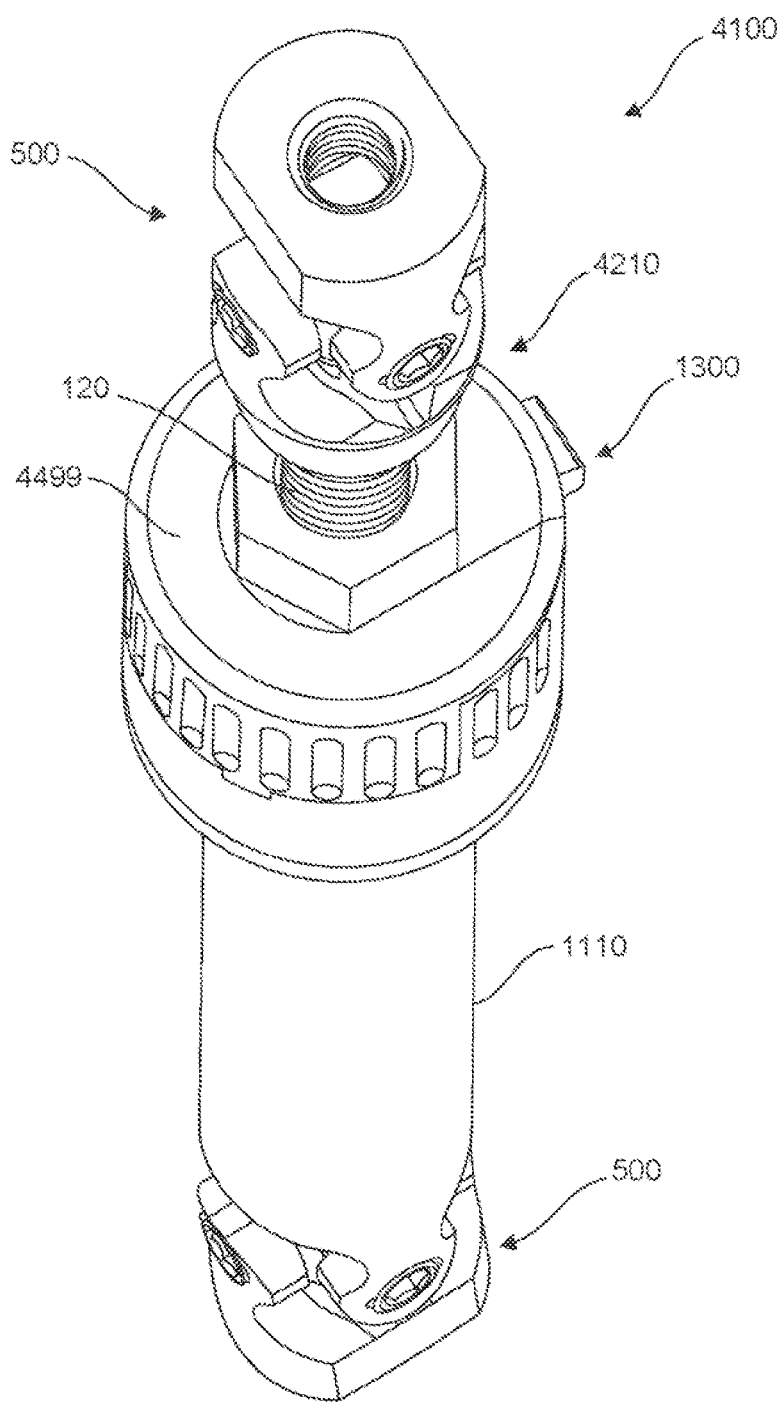
FIG. 21A is a perspective view of most components of the acute adjustment mechanism shown in FIG. 20F with a temporary or acute band installed to hold the disengagement member in an activated position.

Band 4400 placement is depicted in FIGS. 19, 20A, and 20D. In some embodiments, bands 4400 may be arranged and configured as identification (ID) bands for identifying each particular strut in the external fixation system. As such, the bands 4400 may be provided to numerically identify strut assemblies so that each strut assembly may be distinguished for a prescription. The bands 4400 shown slide in and out from a side of the actuator body 4210, as shown in FIG. 20B, although other configurations are envisioned. In use, the bands 4400 are coupled to the external fixation struts 4100. For example, as shown, in one example of an embodiment, the band include pegs, projections, or other connection devices that fit in holes in an associated actuator body to couple the components. For example, the illustrated band 4400 includes arms 4455 (FIGS. 20B, 20C, and 20D) configured to pass through slots 4255 (FIGS. 20B and 20F) and engage with the mobile jaws 4220 within the actuator body to hold the mobile jaws 4220 against the threaded rod 120.

The band 4400 may also act as a safety feature by reducing the risk of inadvertent acute adjustment of the strut assembly by limiting access to the disengagement member 4230. For example, in the illustrated embodiment, the band 4400 is arranged and configured to fit over the actuator body 4210 without pushing, moving, activating, etc. the disengagement member 4230. As such, the band 4400 is arranged and configured to engage the actuator body 4210 without activating the disengagement member 4230 and thus preventing a patient from disengaging the mobile jaws 4220 from the threaded rod 120. As shown, in the illustrated embodiment, the band 4400 includes a recess 4416 arranged and configured to align with and receive the disengagement member 4230 so that the disengagement member 4230 is received within the recess 4416 when the band 4400 is coupled to the actuator body 4210 (e.g., the recess 4416 formed in the band 4400 allows the band 4400 to be fully seated on the actuator body 4210 without pushing the disengagement member (e.g., button) 4230). In use, the arms 4455 of the band 4400 contact and fix the position of the mobile jaws 4220 thereby prohibiting, or at least minimizing, patient access to the disengagement member (e.g., button) 4230 while band 4400 is coupled to the actuator body 4210. Thus arranged, the band 4400 makes it more difficult to inadvertently depress the disengagement member 4230. As previously mentioned, acute adjustment generally takes place clinically during installation of the external fixation frame or during strut change-outs. The bands 4400 may be helpful to avoid inadvertent acute adjustment when a patient is adjusting struts using precise adjustment mechanisms to comply with an adjustment prescription.

Figure 21B:
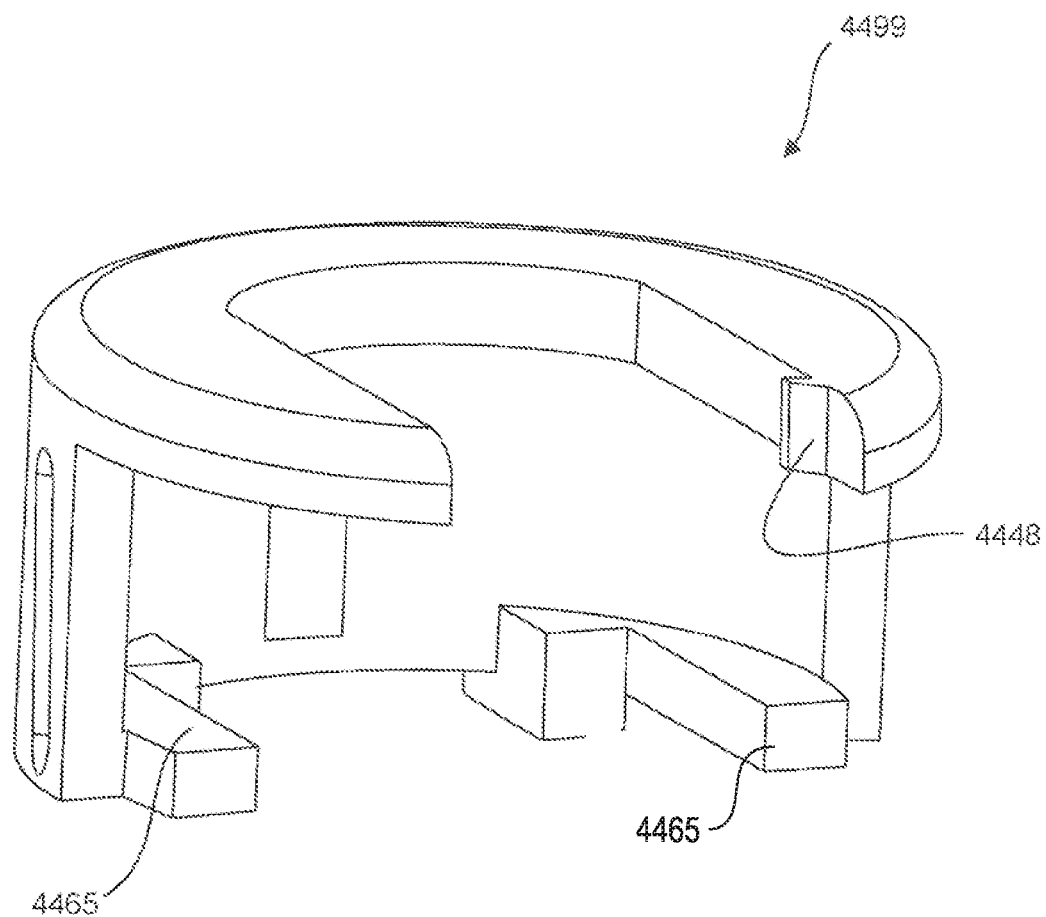
FIG. 21B is a perspective view of the temporary or acute shown in FIG. 21A.
Figure 22A:
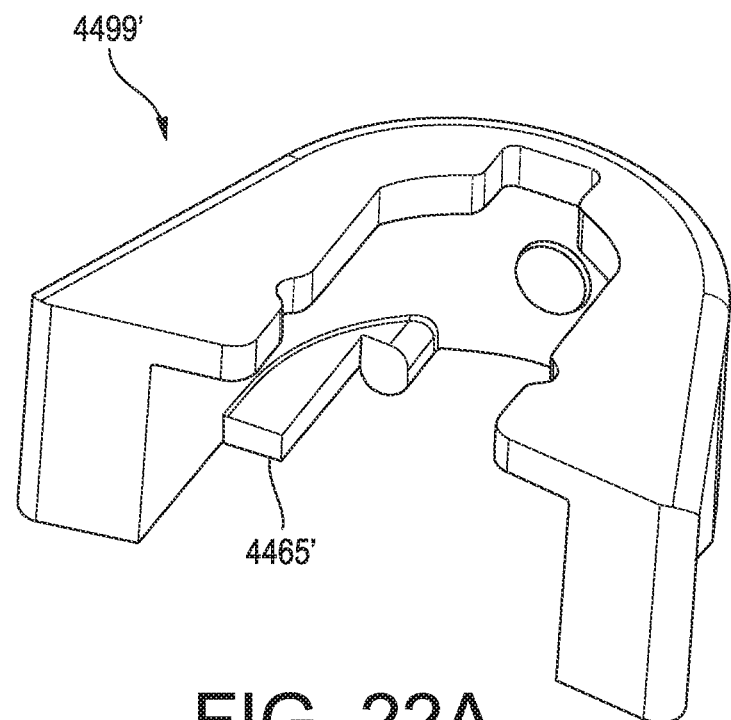
FIG. 22A is a perspective view of an alternate example of an embodiment of a temporary or acute band that may be used with the eternal fixation strut.
Figure 22B:
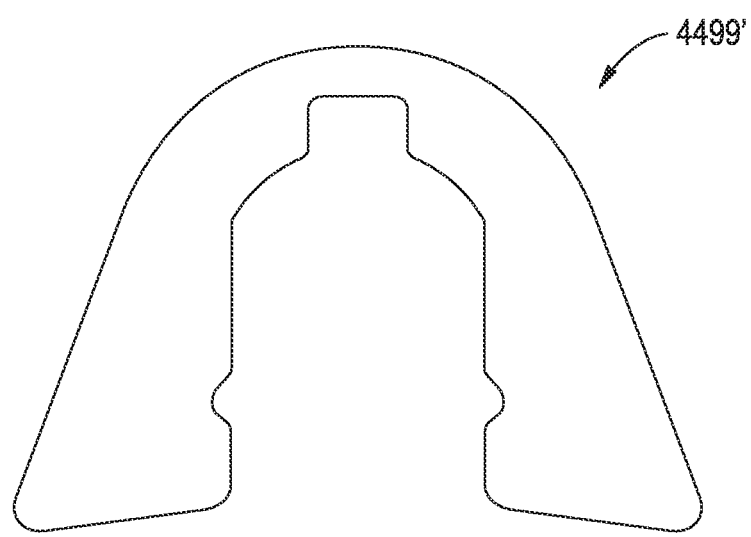
FIG. 22B is a top view of the temporary or acute band shown in FIG. 22A.
Figure 22C:
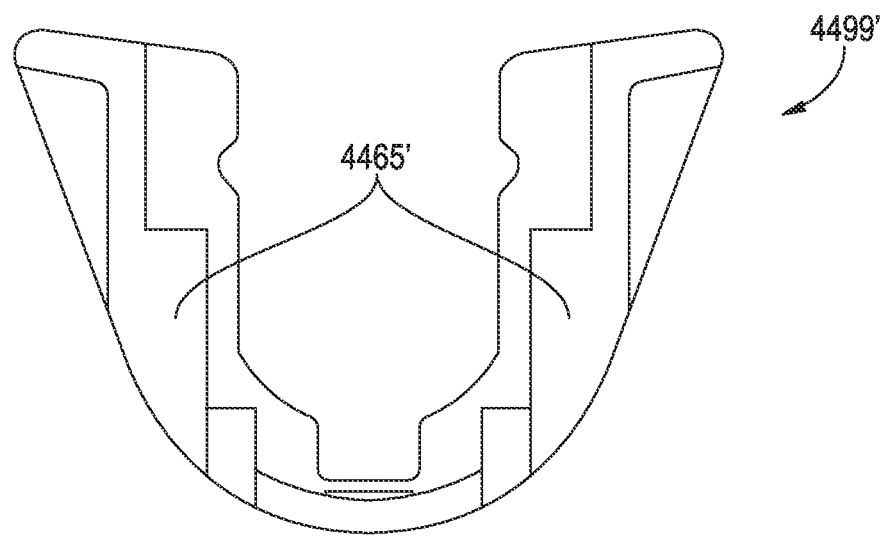
FIG. 22C is a bottom view of the temporary or acute band shown in FIG. 22A.
Figure 22D:
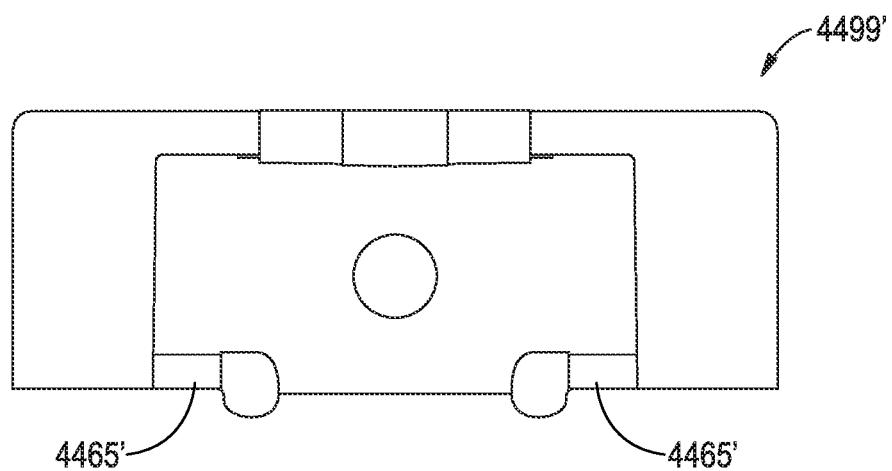
FIG. 22D is a side view of the temporary or acute band shown in FIG. 22A.

As noted above, temporary or acute bands 4499 may be used to hold the disengagement member 4230 in place during acute adjustment of a strut. That is, in contrast to the bands such as, for example, band 4400 described above, the temporary or acute band 4499 shown in FIGS. 21A and 21B are arranged and configured to ensure that the disengagement member (e.g., button) 4230 is activated, pressed, etc. Thus arranged, in use, surgeons can place, engage, etc. a temporary or acute band 4499 on each strut to change the length of a strut freely without having to push in each disengagement member. In this way, surgeons can, for example, have all six struts unlocked at once to adjust a frame acutely. In one example of an embodiment, this can be accomplished by providing a temporary or acute band 4499 without a recess. That is, by eliminating the recess 4416 from band 4400 that is sized and shaped to allow the disengagement member 4230 to not be depressed when the band 4400 is in place on the device, temporary or acute band 4499 contacts and activates the disengagement member 4230 when the temporary or acute band 4499 is coupled to the actuator body. Respective temporary or acute bands 4499 may have an essentially similar geometric configuration as compared to the bands 4400, except for elimination of the recess 4416 and changes to the arms 4455, and may have similar or the same respective size markings or colorings as the bands 4400. Regarding changes to the arms, see temporary arms 4465 in FIG. 21B that are shorter and more lateral and do not contact the mobile jaws 4220 sufficiently to press the mobile jaws 4220 against the threaded rod 120. A lack of the recess 4416 is also evident in the view presented in FIG. 21B, as well as FIG. 21A. Embodiments of the temporary or acute bands 4499 may also include a retention structure, such as a tab 4488 shown in FIGS. 20C, 20D, and 21B, useful in resisting inadvertent disengagement of the temporary or acute bands 4499 from an actuator body.

As previously mentioned, once the disengagement member 4230 has been pressed toward the threaded rod 120, the disengagement member 4230 may be held in this position by a temporary or acute band 4499. By installing multiple temporary or acute bands 4499 on multiple external fixation struts in this manner, multiple external fixation struts can be adjusted acutely at once because the user (e.g., surgeon during initial installation, strut change-out, etc.) is not required to individually press and hold each disengagement member 4230 in the pressed or activated position. Referring to FIGS. 22A-22D, an alternate example embodiment of a temporary or acute band 4499' is disclosed. Temporary or acute band 4499' is substantially similar to temporary or acute band 4499. In use, temporary or acute band 4499' may be used in connection with an external fixator strut disclosed herein. In use, temporary or acute band 4499' is arranged and configured to hold the disengagement member such as, for example, disengagement member 4230 in place during acute adjustment of the strut. In the illustrated embodiment, this can be accomplished by eliminating the recess 4416 that is sized and shaped to allow band 4400 to be coupled to the external fixation strut without depressing the disengagement member 4230 when the band is placed on the device. Respective temporary or acute bands 4499' may have an essentially similar geometric configuration, except for elimination of the recess 4416 and changes to the arms 4455, and may have similar or the same respective size markings or colorings as the bands 4400. Regarding changes to the arms, see temporary arms 4465' that are shorter and more lateral and do not contact the mobile jaws 4220 sufficiently to press the mobile jaws 4220 against the threaded rod 120. A lack of the recess 4416 is also evident in the view presented in FIG. 22A. Embodiments of temporary or acute bands may also include a retention structure, such as a tab, useful in resisting inadvertent disengagement of the temporary or acute band from the actuator body.

Although not shown, the external fixation strut 4100 may also include a locking sleeve such as, for example, the locking sleeve 600 described above in association with FIG. 10. Use of such a device is an option for preventing accidental adjustment.

The external fixation strut 4100 may be a part of an external fixation system that includes an upper base, a lower base, and multiple struts between the upper base and the lower base. At least one of the struts may be the external fixation strut 4100 or one of the other fixation struts disclosed herein. In some embodiments, the system includes six struts coupled between the upper base and the lower base and at least one of the six struts is the external fixation strut 4100, but in other embodiments may include systems with fewer or more struts than six. Any of the struts described herein may also include one or more telescoping bodies that translate relative to one another to change the overall length of the strut. The system may also include connectors for coupling with one or both of the upper base and the lower base. For example, the connectors may include the universal joints 500 and further may include fasteners between the universal joints 500 and the bases. System embodiments may also include bone fixation mechanisms for coupling between the connectors or the bases and tissue of a patient. Such bone fixation mechanisms may include wires (threaded and unthreaded), k-wires, pins, and screws, for example.

An embodiment of the invention is a method of adjusting an external fixation strut, such as the external fixation struts 100, 1100, 4100. Such a method may include disengaging an acute adjustment mechanism 200, 1200, 4200 of the external fixation strut 100, 1100, 4100 from threads formed on a threaded rod 120 of the external fixation strut 100, 1100, 4100. The acute adjustment mechanism 200, 1200, 4200 may be biased toward an engaged state in some illustrated embodiments. The threaded rod 120 may be substantially rotationally fixed relative to a strut body 110, 1110 of the external fixation strut 100, 1100, 4100 so that movement of the threaded rod 120 axially translates or moves the threaded rod 120 relative to the strut body 110, 1110. In some embodiment, the threaded rod 120 may be substantially rotationally fixed relative to a strut body 110, 1110 of the external fixation strut 100, 1100, 4100 by, for example, the tracer pin 610 shown in FIG. 10. In the illustrated embodiments, disengaging the acute adjustment mechanism 200, 1200, 4200 of the external fixation strut 100, 1100 from threads formed on the threaded rod 120 includes moving mobile jaws 220, 1220, 4220 from the threaded rod 120. For example, disengaging the acute adjustment mechanism 200, 1200, 4200 may include separating two substantially oppositely positioned mobile jaws 220, 1220, 4220 from one another. Referring to FIGS. 1A-10, in the embodiment shown with mobile jaws 220, separating the two substantially oppositely positioned mobile jaws 220 includes moving (e.g., translating) the mobile jaws 220 away from the threaded rod 120. In this embodiment, the two substantially oppositely positioned mobile jaws 220 are moved by forcing the disengagement members 230 into contact with both of the mobile jaws 220, as shown by the action arrows in FIG. 3F.

Referring to FIGS. 11A-16 and 19-21B, in the embodiments shown with mobile jaws 1220 and 4220 respectively, separating the two substantially oppositely positioned mobile jaws 1220, 4220 includes moving (e.g., rotating) the mobile jaws 1220, 4220 away from the threaded rod 120. In these embodiments, the two substantially oppositely positioned mobile jaws 1220, 4220 are moved by forcing the disengagement member 1230, 4230 into contact with both of the mobile jaws 1220, 4220, as shown by the action arrows in FIG. 13E and FIG. 20F. The opposite ends of the mobile jaws 1220 from the ends where the mobile jaws 1220 are contacted by the disengagement member 1230 are configured to contact respective surfaces of the actuator body 1210 and pivot against those surfaces. The mobile jaws 4220 pivot about pins 1112 at their opposite ends from the ends where the mobile jaws 4220 are contacted by the disengagement member 4230.

Methods of adjusting the external fixation strut 100, 1100, 4100 may also include moving the acute adjustment mechanism 200, 1200, 4200 relative to the threaded rod 120 to a position closer to a final adjustment position while the acute adjustment mechanism 200, 1200, 4200 is disengaged from the threaded rod 120. The movement may be accomplished manually or by a force created by a motorized drive, pneumatics, hydraulics, or other effective force. The acute adjustment mechanism 200, 1200, 4200 of the external fixation strut 100, 1100, 4100 may then be engaged to the threads of the threaded rod 120 by removing force against the bias toward an engaged state. For example, removing user force may include removing force from the disengagement member 230, 1230, 4230 as biased by their respective springs to the state illustrated in FIGS. 9B, 13D, and 20E.

An embodiment of the invention is a method of adjusting an external fixation strut, such as the external fixation strut 3100. Such a method may include disengaging an acute adjustment mechanism 3200 of the external fixation strut 3100 from threads of a threaded rod 120 of the external fixation strut 3100. The acute adjustment mechanism 3200 may be biased toward a disengaged state. The threaded rod 120 shown is substantially rotationally fixed relative to a strut body 1110 of the external fixation strut 3100 so that movement of the threaded rod 120 axially translates or moves the threaded rod 120 relative to the strut body 1110. In some embodiment, the threaded rod 120 may be substantially rotationally fixed relative to a strut body 1110 of the external fixation strut 3100 by, for example, the tracer pin 610 shown in FIG. 10. In the illustrated embodiment, disengaging the acute adjustment mechanism 3200 of the external fixation strut 3100 from threads of a threaded rod 120 includes allowing the two substantially oppositely positioned mobile jaws 3220 to separate. This may include allowing the disengagement member 3230 to translate away from the threaded rod 120. Specifically, as shown in FIG. 18C, the disengagement member 3230 is allowed to translate away from the threaded rod 120 by removing the band 3400 from the device.

In this state, the acute adjustment mechanism 3200 may be moved relative to the threaded rod to a position closer to a final adjustment position. The movement may be accomplished manually or by a force created by a motorized drive, pneumatics, hydraulics, or other effective force. The acute adjustment mechanism 3200 of the external fixation strut 1100 may then be engaged to the threads of the threaded rod 120 by applying force against the bias toward a disengaged state. For example, user force may be applied against the disengagement member 3230.

In the embodiment illustrated in FIGS. 17-18D, engaging the acute adjustment mechanism 3200 of the external fixation strut 3100 to the threads of the threaded rod 120 includes applying force to the disengagement member 3230 against the bias toward a disengaged state. The band 3400 may be placed over the actuator body 3210 of the acute adjustment mechanism 3200 to keep the acute adjustment mechanism engaged with the threads of the threaded rod 120.

Methods of adjusting the external fixation strut 100, 1100, 3100, 4100 may also include releasing a lock of a precise adjustment mechanism 300, 1300 that is configured to lock between the strut body 110, 1110 and the acute adjustment mechanism 200, 1200, 3200, 4200. For example, in the embodiment shown in FIGS. 1A-9D, the lock includes the plunger 320 coupled to the strut body 110 through the body 310 of the precise adjustment mechanism, and the plunger 320 is releasable from the cavities 252 in the threaded collar

250 that is part of the acute adjustment mechanism 200 by translating the plunger 320 away from its locked state in the cavity 252. Movement of the plunger 320 illustrated away from its locked state includes overcoming the spring bias of the spring 330.

In the embodiments shown in FIGS. 11A-16, FIGS. 17-18D, and FIGS. 19-21B, the lock includes the notches 1180 that are part of the strut body 1110, and the body 1310 of the precise adjustment mechanism 1300 coupled to the acute adjustment mechanism 1200, 3200, 4200 is releasable from the notches 1180 by pivoting the body 1310 of the precise adjustment mechanism 1300 away from its locked state in the notch 1180. Movement of the body 1310 of the precise adjustment mechanism 1300 away from its locked state includes overcoming the spring bias of the spring 1330.

With the lock of the precise adjustment mechanism 300, 1300 in a released state, another act of the method of adjusting the external fixation strut 100, 1100, 3100, 4100 includes rotating the acute adjustment mechanism 200, 1200, 3200, 4200 relative to the strut body 110, 1110 to move the threaded rod 120 longitudinally relative to the strut body 110, 1110. A result of such rotation is a lengthening or shortening of the external fixation strut 100, 1100, 3100, 4100 as may be prescribed to achieve external fixation goals.

In some implementations, one end of the external fixation strut 100, 1100, 3100, 4100 may be coupled to an upper base, and an opposite send of the external fixation strut 100, 1100, 3100, 4100 may be coupled to a lower base. In such a configuration, the act of rotating the acute adjustment mechanism 200, 1200, 3200, 4200 relative to the strut body 110, 1110, as detailed above, moves the upper base relative to the lower base. In some embodiments, implementation may include coupling one end of each of six external fixation struts 100, 1100, 3100, 4100 to an upper base and an opposite end of each of the six external fixation struts 100, 1100, 3100, 4100 to a lower base. In such embodiments, rotating the acute adjustment mechanism 200, 1200, 3200, 4200 of each of the six external fixation struts 100, 1100, 3100, 4100 relative to its respective strut body 110, 1110 moves the upper base relative to the lower base.

Various embodiments of a system wholly or its components individually may be made from any biocompatible material. Instruments that will not be implanted and remain in a patient may not necessarily be biocompatible. For example and without limitation, materials may include in whole or in part: non-reinforced polymers, reinforced polymers, metals, ceramics, adhesives, reinforced adhesives, and combinations of these materials. Reinforcing of polymers may be accomplished with carbon, metal, or glass or any other effective material. Examples of biocompatible polymer materials include polyamide base resins, polyethylene, Ultra High Molecular Weight (UHMW) polyethylene, low density polyethylene, polymethylmethacrylate (PMMA), polyetheretherketone (PEEK), polyetherketoneketone (PEKK), a polymeric hydroxyethylmethacrylate (PHEMA), and polyurethane, any of which may be reinforced. Example biocompatible metals include stainless steel and other steel alloys, cobalt chrome alloys, zirconium, oxidized zirconium, tantalum, titanium, titanium alloys, titanium-nickel alloys such as Nitinol, and other superelastic or shape-memory metal alloys.

In one example of an embodiment, an external fixation strut is disclosed, the external fixation strut comprising: a strut body; a threaded rod substantially rotationally fixed relative to the strut body; an acute adjustment mechanism selectively disengageable from threads of the threaded rod, the acute adjustment mechanism comprising: an actuator body, a mobile jaw that is engageable with threads of the threaded rod, and a disengagement member configured to interact with the mobile jaw to disengage the mobile jaw from the threads of the threaded rod.

In another example of an embodiment, an external fixation system is disclosed. The external fixation system comprising: an upper base; a lower base; and at least two struts coupled between the upper base and the lower base, at least one of the struts comprising: a strut body; a threaded rod substantially rotationally fixed relative to the strut body; an acute adjustment mechanism selectively disengageable from threads of the threaded rod, the acute adjustment mechanism comprising: an actuator body, a mobile jaw that is engageable with threads of the threaded rod, and a disengagement member configured to interact with the mobile jaw to disengage the mobile jaw from the threads of the threaded rod.

In these and other embodiments, the external fixation strut may further comprise a precise adjustment mechanism comprising a lock between the strut body and the actuator body; wherein the lock is biased to fix the strut body with the actuator body rotationally, but may be activated to allow for rotation of the actuator body relative to the strut body to move the threaded rod longitudinally relative to the strut body.

In these and other embodiments, the lock of the precise adjustment mechanism includes a base coupled to the strut body, a plunger biased away from the base, and a cavity in the actuator body sized to receive the plunger to restrict rotational movement of the strut body relative to the actuator body.

In these and other embodiments, the lock of the precise adjustment mechanism includes a pivot coupled to the actuator body with a portion biased toward the strut body configured to fit in a notch in the strut body to restrict rotational movement of the strut body relative to the actuator body when the portion is in the notch in the strut body.

In these and other embodiments, the mobile jaw may include a threaded surface configured to engage with threads of the threaded rod.

In these and other embodiments, the acute adjustment mechanism may include two substantially oppositely positioned mobile jaws configured to engage with threads of the threaded rod on substantially opposite sides of the threaded rod.

In these and other embodiments, the substantially oppositely positioned mobile jaws each include a threaded surface configured to engage with threads of the threaded rod.

In these and other embodiments, the mobile jaw is biased to engage with the threaded rod.

In these and other embodiments, the mobile jaw is biased to disengage from the threaded rod.

In these and other embodiments, the disengagement member is a button configured to interact with the mobile jaw to disengage the mobile jaw from the threads of the threaded rod when the button is moved by a user.

In these and other embodiments, the button includes an angled face configured to interact with one or more faces of the mobile jaw to disengage the mobile jaw from the teeth of the threaded rod.

In these and other embodiments, the button includes a rounded face configured to interact with one or more faces of the mobile jaw to disengage the mobile jaw away from the threaded rod.

In these and other embodiments, the disengagement member is configured to translate toward the mobile jaw to disengage the mobile jaw from the threaded rod and to be rotated about the disengagement member's axis of translation to lock the acute adjustment mechanism in a state of free movement where the mobile jaw is disengaged from the threaded rod.

In these and other embodiments, the disengagement member is configured to translate away from the mobile jaw to enable the mobile jaw to disengage from the threaded rod.

In these and other embodiments, the disengagement member includes a containment device configured to prevent the mobile jaw from moving away from the threads of the threaded rod when the containment device is coupled to the acute adjustment mechanism.

In these and other embodiments, the containment device is arranged and configured as an ID band.

In these and other embodiments, the mobile jaw is configured to translate away from the threaded rod when interacted with by the disengagement member.

In these and other embodiments, the mobile jaw is configured to pivot away from the threaded rod when interacted with by the disengagement member.

In these and other embodiments, the actuator body includes a threaded collar that couples the actuator body with the strut body.

In these and other embodiments, the actuator body includes channels configured to guide the movement of the mobile jaw when the mobile jaw is interacted with the disengagement member.

In these and other embodiments, the actuator body includes channels configured to constrain the movement of protrusions on the mobile jaw when the mobile jaw is interacted on by the disengagement member.

In these and other embodiments, the mobile jaw has one or more angled faces configured to interact with the disengagement member to move the mobile jaw away from the threaded rod.

In these and other embodiments, the external fixation strut may also include a rotatable sleeve that is sized to fit over the outside of the actuator body with one or more openings for access to the disengagement member.

In these and other embodiments, when the rotatable sleeve is rotated relative to the actuator body, access to the disengagement member is blocked.

In these and other embodiments, when the rotatable sleeve is rotated relative to the actuator body a portion of opening interacts with the disengagement member to disengage the mobile jaw from the threaded rod.

In these and other embodiments, the actuator body includes openings for projections of a band to prevent disengagement of the mobile jaw from the threaded rod.

In these and other embodiments, a band covers the disengagement member when the band is positioned on the acute adjustment mechanism to prevent access to the disengagement member.

In these and other embodiments, the external fixation strut may also include connectors for coupling with one or both of the upper base and the lower base.

In these and other embodiments, the external fixation strut may also include bone fixation mechanisms for coupling between the connectors and tissue of a patient.

In another example of an embodiment, a method of adjusting an external fixation strut is disclosed. The method comprising: disengaging an acute adjustment mechanism of the external fixation strut from threads of a threaded rod of the external fixation strut, wherein the acute adjustment mechanism is biased toward an engaged state, and wherein the threaded rod is substantially rotationally fixed relative to a strut body of the external fixation strut; moving the acute adjustment mechanism relative to the threaded rod to a position closer to a final adjustment position; and engaging the acute adjustment mechanism of the external fixation strut to the threads of the threaded rod by removing force against the bias toward an engaged state.

In another example of an embodiment, a method of adjusting an external fixation strut is disclosed. The method comprising: disengaging an acute adjustment mechanism of the external fixation strut from threads of a threaded rod of the external fixation strut, wherein the acute adjustment mechanism is biased toward a disengaged state, and wherein the threaded rod is substantially rotationally fixed relative to a strut body of the external fixation strut; moving the acute adjustment mechanism relative to the threaded rod to a position closer to a final adjustment position; and engaging the acute adjustment mechanism of the external fixation strut to the threads of the threaded rod by applying force against the bias toward a disengaged state.

In these and other embodiments, the method may further comprise releasing a lock of a precise adjustment mechanism that is configured to lock between the strut body and the acute adjustment mechanism; wherein with the lock of the precise adjustment mechanism in a released state, rotating the acute adjustment mechanism relative to the strut body to move the threaded rod longitudinally relative to the strut body.

In these and other embodiments, releasing the lock of the precise adjustment mechanism includes overcoming a spring bias of the lock toward a locked state.

In these and other embodiments, releasing the lock of the precise adjustment mechanism includes translating a lock component away from a locked state.

In these and other embodiments, releasing the lock of the precise adjustment mechanism includes rotating a lock component away from a locked state.

In these and other embodiments, disengaging an acute adjustment mechanism of the external fixation strut from threads of the threaded rod of the external fixation strut includes separating two substantially oppositely positioned mobile jaws.

In these and other embodiments, separating the two substantially oppositely positioned mobile jaws includes moving a disengagement member into contact with both of the mobile jaws.

In these and other embodiments, separating the two substantially oppositely positioned mobile jaws includes translating the two substantially oppositely positioned mobile jaws away from the threaded rod.

In these and other embodiments, separating the two substantially oppositely positioned mobile jaws includes pivoting the two substantially oppositely positioned mobile jaws away from the threaded rod.

In these and other embodiments, disengaging an acute adjustment mechanism of the external fixation strut from threads of the threaded rod of the external fixation strut includes allowing two substantially oppositely positioned mobile jaws to separate.

In these and other embodiments, allowing the two substantially oppositely positioned mobile jaws to separate includes allowing a disengagement member to translate away from the threaded rod.

In these and other embodiments, allowing the two substantially oppositely positioned mobile jaws to separate includes removing a band from the disengagement member.

In these and other embodiments, the method may further comprise coupling one end of the external fixation strut to an upper base and an opposite end of the external fixation strut to a lower base, and wherein rotating the acute adjustment mechanism relative to the strut body moves the upper base relative to the lower base.

In these and other embodiments, the method may further comprise coupling one end of each of six external fixation struts to an upper base and an opposite end of each of the six external fixation struts to a lower base, and wherein rotating the acute adjustment mechanism of each of the six external fixation struts relative to its respective strut body moves the upper base relative to the lower base.

Terms such as closer, underneath, over, around, medial, lateral, inside, outside and the like have been used relatively herein. However, such terms are not limited to specific coordinate orientations, distances, or sizes, but are used to describe relative positions referencing particular embodiments. Such terms are not generally limiting to the scope of the claims made herein. Any embodiment or feature of any section, portion, or any other component shown or particularly described in relation to various embodiments of similar sections, portions, or components herein may be interchangeably applied to any other similar embodiment or feature shown or described herein.

The foregoing description has broad application. While embodiments of the invention have been illustrated and described in detail in the disclosure, the disclosure is to be considered as illustrative and not restrictive in character. All changes and modifications that come within the spirit of the invention are to be considered within the scope of the disclosure. Accordingly, the discussion of any embodiment is meant only to be explanatory and is not intended to suggest that the scope of the disclosure, including the claims, is limited to these examples. In other words, while illustrative embodiments of the disclosure have been described in detail herein, it is to be understood that the inventive concepts may be otherwise variously embodied and employed, and that the appended claims are intended to be construed to include such variations, except as limited by the prior art.

The foregoing discussion has been presented for purposes of illustration and description and is not intended to limit the disclosure to the form or forms disclosed herein. For example, various features of the disclosure are grouped together in one or more aspects, embodiments, or configurations for the purpose of streamlining the disclosure. However, it should be understood that various features of the certain aspects, embodiments, or configurations of the disclosure may be combined in alternate aspects, embodiments, or configurations.

The phrases "at least one", "one or more", and "and/or", as used herein, are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

The term "a" or "an" entity, as used herein, refers to one or more of that entity. As such, the terms "a" (or "an"), "one or more" and "at least one" can be used interchangeably herein. The use of "including," "comprising," or "having" and variations thereof herein is meant to encompass the items listed thereafter and equivalents thereof as well as additional items. Accordingly, the terms "including," "comprising," or "having" and variations thereof are open-ended and can be used interchangeably herein.

All directional references (e.g., proximal, distal, upper, lower, upward, downward, left, right, lateral, longitudinal, front, back, top, bottom, above, below, vertical, horizontal, radial, axial, clockwise, and counterclockwise) are only used for identification purposes to aid the reader's understanding of the present disclosure, and do not create limitations, particularly as to the position, orientation, or use of this disclosure. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. Identification references (e.g., primary, secondary, first, second, third, fourth, etc.) are not intended to connote importance or priority but are used to distinguish one feature from another. The drawings are for purposes of illustration only and the dimensions, positions, order and relative sizes reflected in the drawings attached hereto may vary.

What is claimed is:

1. An external fixation strut comprising:
   a strut body operatively associated with a first connector;
   a threaded rod including external threads formed thereon, the threaded rod being operatively associated with a second connector; and
   an adjustment mechanism including:
      an actuator body;
      a mobile jaw including internal threads engageable with the external threads of the threaded rod so that when the internal threads of the mobile jaw are engaged with the external threads of the threaded rod movement of the threaded rod relative to the strut body moves the first connector relative to the second connector;
      a disengagement member selectively movable from a first position to a second position, in the first position, the disengagement member interacts with the mobile jaw to engage the internal threads of the mobile jaw with the external threads of the threaded rod, in the second position, the disengagement member interacts with the mobile jaw to disengage the internal threads of the mobile jaw from the external threads of the threaded rod to enable the strut body to be slidable adjustable relative to the threaded rod; and
      a band selectively coupled to the actuator body, the band being configured to at least partially encase the actuator body to interact with the disengagement member to prevent access to the disengagement member and to prevent movement of the disengagement member from the first position to the second position when coupled to the actuator body.

2. The external fixation strut of claim 1, wherein the adjustment mechanism includes two oppositely positioned mobile jaws configured to engage with the external threads of the threaded rod on opposite sides of the threaded rod.

3. The external fixation strut of claim 1, wherein the mobile jaw is biased to engage with the threaded rod.

4. The external fixation strut of claim 1, wherein the disengagement member is configured as a button configured to interact with the mobile jaw to disengage the internal threads of the mobile jaw from the external threads of the threaded rod when the button is moved from the first position to the second position.

5. The external fixation strut of claim 1, wherein the disengagement member is configured to translate toward the mobile jaw when moved from the first position to the second position to disengage the internal threads of the mobile jaw from the external threads of the threaded rod.

6. The external fixation strut of claim 5, wherein the disengagement member is also configured to rotate about an axis of translation of the disengagement member to secure the disengagement member in a state of free movement.

7. The external fixation strut of claim 1, wherein the disengagement member is configured to translate away from the mobile jaw when moved from the first position to the second position to disengage the internal threads of the mobile jaw from the external threads of the threaded rod.

8. The external fixation strut of claim 1, wherein the mobile jaw is configured to translate away from the threaded rod when interacted with by the disengagement member.

9. The external fixation strut of claim 1, wherein the actuator body includes a threaded collar that couples the actuator body with the strut body.

10. The external fixation strut of claim 1, wherein the actuator body includes channels configured to guide the movement of the mobile jaw when the mobile jaw is interacted with by the disengagement member.

11. The external fixation strut of claim 1, wherein the actuator body includes channels configured to constrain the movement of protrusions on the mobile jaw when the mobile jaw is interacted on by the disengagement member.

12. The external fixation strut of claim 1, further comprising a rotatable sleeve configured to at least partially encase the actuator body, the rotatable sleeve including one or more openings to access the disengagement member.

13. The external fixation strut of claim 12, wherein when the rotatable sleeve is rotated relative to the actuator body, access to the disengagement member is blocked.

14. The external fixation strut of claim 13, wherein when the rotatable sleeve is rotated relative to the actuator body, a portion of the one or more openings interact with the disengagement member to disengage the internal threads of the mobile jaw from the external threads of the threaded rod.

15. The external fixation strut of claim 1, further comprising a precise adjustment mechanism comprising a lock positioned between the strut body and the actuator body;
wherein the lock is movable between a first position and a second position, in the first position, the lock is arranged and configured to rotationally fix the strut body relative to the actuator body, in the second position, the lock is arranged and configured to enable rotation of the actuator body relative to the strut body to move the threaded rod longitudinally relative to the strut body.

16. The external fixation strut of claim 15, wherein the lock of the precise adjustment mechanism includes:
a base coupled to the strut body;
a plunger biased away from the base; and
a cavity formed in the actuator body, the cavity arranged and configured to receive the plunger to restrict rotational movement of the strut body relative to the actuator body.

17. The external fixation strut of claim 16, wherein the lock of the precise adjustment mechanism includes:
a pivot coupled to the actuator body, the pivot being biased toward the strut body and being arranged and configured to fit in a notch formed in the strut body to restrict rotational movement of the strut body relative to the actuator body when a portion of the pivot is positioned in the notch in the strut body.

18. The external fixation strut of claim 1, wherein the actuator body includes openings for projections of the band to prevent disengagement of the internal threads of the mobile jaw from the external threads of the threaded rod.

19. The external fixation strut of claim 1, wherein the band is configured as an identification (ID) band to identify each particular strut in an external fixation system.

20. An external fixation strut comprising:
a strut body operatively associated with a first connector;
a threaded rod including external threads formed thereon, the threaded rod being operatively associated with a second connector; and
an adjustment mechanism including:
an actuator body;
a mobile jaw including internal threads engageable with the external threads of the threaded rod so that when the internal threads of the mobile jaw are engaged with the external threads of the threaded rod movement of the threaded rod relative to the strut body moves the first connector relative to the second connector;
a disengagement member selectively movable from a first position to a second position, in the first position, the disengagement member interacts with the mobile jaw to engage the internal threads of the mobile jaw with the external threads of the threaded rod, in the second position, the disengagement member interacts with the mobile jaw to disengage the internal threads of the mobile jaw from the external threads of the threaded rod to enable the strut body to be slidable adjustable relative to the threaded rod; and
an identification (ID) band configured to identify each particular strut in an external fixation system, the ID band configured to at least partially encase the actuator body to interact with the disengagement member to prevent movement of the disengagement member from the first position to the second position when coupled to the actuator body.

21. The external fixation strut of claim 20, wherein the disengagement member is configured as a button configured to interact with the mobile jaw to disengage the internal threads of the mobile jaw from the external threads of the threaded rod when the button is moved from the first position to the second position.

* * * * *